US012260944B2

(12) United States Patent
Davies et al.

(10) Patent No.: US 12,260,944 B2
(45) Date of Patent: Mar. 25, 2025

(54) DRUG DOSAGE DETERMINATION DEVICES AND METHODS

(71) Applicant: Hoffmann-La Roche Inc., Little Falls, NJ (US)

(72) Inventors: Geraint Iwan Davies, Basel (CH); David Elfant, Basel (CH); Martin Jenkins, Southampton (GB)

(73) Assignee: HOFFMANN-LA-ROCHE INC., Little Falls, NJ (US)

( * ) Notice: Subject to any disclaimer, the term of this patent is extended or adjusted under 35 U.S.C. 154(b) by 323 days.

(21) Appl. No.: 17/767,842

(22) PCT Filed: Oct. 7, 2020

(86) PCT No.: PCT/EP2020/078139
§ 371 (c)(1),
(2) Date: Apr. 8, 2022

(87) PCT Pub. No.: WO2021/069504
PCT Pub. Date: Apr. 15, 2021

(65) Prior Publication Data
US 2023/0145898 A1    May 11, 2023

(30) Foreign Application Priority Data
Oct. 11, 2019  (AU) ................................ 2019903839
Oct. 11, 2019  (EP) .................................... 19202828

(51) Int. Cl.
G16H 20/10    (2018.01)
(52) U.S. Cl.
CPC .................................. G16H 20/10 (2018.01)
(58) Field of Classification Search
CPC .................................................... G16H 20/10
(Continued)

(56) References Cited

U.S. PATENT DOCUMENTS

2002/0143579 A1* 10/2002 Docherty ............... G16H 40/67
705/2
2015/0085624 A1    3/2015 Zamjahn
(Continued)

FOREIGN PATENT DOCUMENTS

EP          2644698 B1    1/2018
JP       2007172107 A    7/2007
(Continued)

OTHER PUBLICATIONS

Wen, Hong et al. "Drug Delivery Approaches in Addressing Clinical Pharmacology-Related Issues: Opportunities and Challenges." The AAPS journal vol. 17,6 (2015): 1327-40. doi: 10.1208/s12248-015-9814-9 (Year: 2015).*

(Continued)

*Primary Examiner* — Joy Chng
(74) *Attorney, Agent, or Firm* — MORRISON & FOERSTER LLP

(57) ABSTRACT

The application relates to devices and methods for determining an administration regimen of a drug to a subject. Determining an administration regimen for a subject comprises computing the amount of drug to be administered to the subject per elemental period of time, and determining and evaluating combinations of at least two dosage forms that can be used to administered the amount of drug, against at least two different criteria. The methods of the invention find applications in the selection of administration regimen for drugs that are available in multiple dosage forms, and especially drugs that are administered routinely over prolonged periods, such as e.g. in the routine prophylaxis of haemophilia.

14 Claims, 4 Drawing Sheets

(58) Field of Classification Search
USPC .......................................................... 705/2–3
See application file for complete search history.

(56) References Cited

U.S. PATENT DOCUMENTS

2017/0173060 A1    6/2017  Schentag et al.
2018/0280245 A1*  10/2018  Khalid ..................... A61J 7/04

FOREIGN PATENT DOCUMENTS

| JP | 2019514114 A | 5/2019 | |
| WO | WO-2013082573 A1 * | 6/2013 | ........... A61K 31/135 |
| WO | WO-2017180807 A1 * | 10/2017 | ......... A61K 49/0004 |
| WO | 2017210538 A1 | 12/2017 | |

OTHER PUBLICATIONS

International Search Report and Written Opinion mailed on Jan. 13, 2021, for PCT Patent Application No. PCT/EP2020/078139 filed on Oct. 7, 2020, thirteen pages.

* cited by examiner

DRUG DOSAGE DETERMINATION DEVICES AND METHODS

CROSS REFERENCE TO RELATED APPLICATIONS

This application is a U.S. national stage application under 35 U.S.C. § 371 of International Application No. PCT/EP2020/078139, filed internationally on Oct. 7, 2020, which claims the priority benefit of Australian Patent Application No. 2019903839, filed on Oct. 11, 2019, and European Patent Application No. 19202828.0, filed on Oct. 11, 2019, the disclosures of each of which are hereby incorporated by reference in their entireties.

FIELD OF THE INVENTION

The present invention relates to computer-implemented methods for determining an administration regimen of a drug to a subject, as well as computing devices implementing the methods. The methods and devices of the invention find application in the determination of administration regimen for drugs that are available in multiple dosage forms that differ by their amounts of drug and/or drug concentration, and particularly for drugs that are to be administered regularly over prolonged periods of time for prophylactic and/or therapeutic purposes.

BACKGROUND TO THE INVENTION

Many diseases and conditions require regular administration of drugs for therapeutic and/or prophylactic purposes. Through clinical trials, safe and efficient loadings of the drug are typically determined together with amounts of drug and intervals between administrations that can be used to achieve these loadings. These may further depend on one or more parameters associated with the patient such as their weight, age, sex, etc. Different combinations of amounts of drugs and intervals between administrations may exist which may satisfy the conditions set by the clinical trials. Further, drugs can be made available in multiple different dosage forms, in order to increase flexibility of administration.

It is typically left to the health care practitioner to choose an administration regimen that satisfies the conditions set by the clinical trials and is appropriate for a particular patient. This may be a complex task, and the choice of a particular regimen may therefore result in avoidable inconvenience and/or expense for the patient. These may be particularly problematic in the case of high-value products that are administered over long periods of time, and/or where administration is comparatively complex (such as e.g. by injection). Accordingly, there is an unmet need for means to determine an administration regimen for a patient where the choice between multiple possibilities is not trivial. Simple tools exist that calculate the amount of drug to be administered to a patient based on a patient's weight and a relationship between weight and amount of drug to be administered. These tools reduce the risk of error in the calculation of the amount of drug to be administered. Nevertheless, given the high practical impact of a choice of administration regimen for a patient, there remains a need in the art for more efficient and accurate means to determine an administration regimen for a patient.

STATEMENTS OF INVENTION

The inventors have developed a new device and method for determining an administration regimen of a drug to a subject, where the drug is available in at least two different dosage forms and a choice of administration regimen has an impact on at least two different criteria. The method and device stems from the discovery that suboptimal administration regimens may regularly be chosen by healthcare practitioners in such circumstances, and that the complexity of the problem of choosing a suitable administration regimen may far outweigh the mental capability of a healthcare practitioner tasked with this. The present inventors have identified that this can be at least partially explained by the observation that there may be an exponential explosion of the number of possible administration regimens that fall within the boundaries set by clinical trials and that a choice of combinations may have non-intuitive consequences on a set of criteria of relevance to a patient.

A first aspect of the present invention thus provides a computing device comprising a processor and a memory, wherein the computing device is configured to determine an administration regimen of a drug to a subject by: receiving the value of at least one parameter associated with the subject; determining the amount of drug ($A_t$) to be administered to the subject per elemental period of time (t) based at least in part on the value of the at least one parameter associated with the subject, wherein the drug is available in at least two different dosage forms (D1,D2) that differ by the total amount of drug and/or the drug concentration in a dose of the dosage form; computing all minimal combinations ($A_t$ [D1,D2, D1D2]) of the at least two different dosage forms that can be used to achieve the amount of drug ($A_t$) to be administered to the subject, wherein a minimal combination is a combination that reaches or exceeds the amount of drug ($A_t$) by using the minimum number of doses of each dosage form in a combination of dosage forms (D1, D2, D1D2); selecting a subset of the combinations ($A_t$ [D1,D2, D1 D2]) that satisfy at least a first criterion and a second criterion; and outputting the selected subset of combinations as the optimal administration regimen(s) for the subject.

The present inventors have identified that multiple combinations of the at least two dosage forms could often be used to administer an amount of drug, and that not all such combinations would be considered according to the prior art. The present inventors have further identified that computing all possible combinations that are useful to evaluate could be achieved by defining the concept of minimal combinations and computing all such minimal combinations for automatic evaluation and selection.

Computing all minimal combinations ($A_t$ [D1,D2, D1D2]) of the at least two different dosage forms that can be used to achieve the amount of drug ($A_t$) to be administered to the subject may comprise: (a) computing the minimum number of doses of each dosage formulation that achieves the amount of drug ($A_t$) to be administered to the subject (single dosage form combinations); and (b) starting from each dosage form, computing the minimum number of doses of each of the other dosage forms that is required to achieve the amount of drug ($A_t$) to be administered to the subject in combination with increasing numbers of doses of the starting dosage form below the number obtained in (a) for the starting dosage form. Where three or more dosage forms can be used, computing all minimal combinations may further comprise: (c) starting from each dosage form, computing the minimum number of doses of each of the other dosage forms that is required to achieve the amount of drug ($A_t$) to be administered to the subject in combination with: increasing numbers of doses of the starting dosage form and increasing numbers of doses of each of the other dosage forms in turn.

Also provided herein is a computer-implemented method for determining an administration regimen of a drug to a subject, the method comprising: receiving the value of at least one parameter associated with the subject; determining the amount of drug ($A_t$) to be administered to the subject per elemental period of time (t) based at least in part on the value of the at least one parameter associated with the subject, wherein the drug is available in at least two different dosage forms (D1,D2) that differ by the total amount of drug and/or the drug concentration in a dose of the dosage form; computing all minimal combinations ($A_t$ [D1,D2, D1D2]) of the at least two different dosage forms that can be used to achieve the amount of drug ($A_t$) to be administered to the subject, wherein a minimal combination is a combination that reaches or exceeds the amount of drug ($A_t$) to be administered to the subject by using the minimum number of doses of each dosage form in a combination of dosage forms (D1,D2, D1D2); selecting a subset of the combinations ($A_t$ [D1,D2, D1D2]) that satisfy at least a first criterion and a second criterion; and outputting the selected subset of combinations as the optimal administration regimen(s) for the subject.

Any of the features of the methods described herein are equally applicable to the computing devices configured to implement these methods. Similarly, any of the features described herein in relation to computing devices may apply to the methods described herein, which the computing devices are configured to implement.

Within the context of the present disclosure, a drug is an active ingredient or ingredients that is administered to a subject for therapeutic or prophylactic purposes. A dosage form is a pharmaceutical formulation of the drug, each dose of the dosage form including a certain amount of the drug and optionally excipients. Where excipients are included, the dosage forms may differ by the concentration of drug in the dosage form. Regardless of whether excipients are included in a dosage form, dosage forms may differ by the total amount of drug in each dose of the dosage form. A dose of a dosage form may be a single pill, tablet, capsule, vial of solution, or any other individual dose formulated according to the dosage form.

The devices and methods of the present disclosure may be particularly advantageous where at least one of the dosage forms is a single use dosage form. A single use dosage form is a dosage form where each dose can only be used for a single administration. Once a dose of a single use dosage form has been at least partly consumed as part of a single administration, the remaining of the dose is wasted and cannot be used for a subsequent administration. For example, a dose of a single use dosage form may be a vial of solution comprising a sterile solution, or any other dosage form that is sterile prior to consumption and where consumption of part of the dose compromises the sterility of the remaining of the dose. Similarly, a single use dosage form may be any dosage form where consumption of part of a dose of the dosage form compromises a property of the remaining of the dose. The property may be related to safety (e.g. contamination, creation of derivative forms of the drug, etc.) or efficacy (e.g. degradation of the drug). For example, a dosage form may comprise a component that oxidises or otherwise degrades on exposure to air and where any remaining part of a dose could be exposed to air during or following consumption of a part of the dose. When at least one of the dosage forms is a single use dosage form, selection of which combination of dosage forms should be used may be particularly important as different combinations may be associated with different amounts of wastage (remaining part of a dose following partial consumption).

The drug may be a biopharmaceutical. In embodiments, the drug is a polypeptide or protein. For example, the drug may consist of or comprise an antibody. In embodiments, the drug is an antibody as described in EP2644698B1, which is incorporated herein by reference. In embodiments, the drug is emicizumab (commercially available as HEMLIBRA®). The devices and methods of the present disclosure may be particularly advantageous in the context of biopharmaceuticals because biopharmaceuticals can be expensive and difficult to produce. Further, biopharmaceuticals may have relatively short shelf life and/or may be available only as single use dosage forms. As such, optimisation of the parameters of administration can be particularly important for these types of products.

The devices and methods of the present disclosure are particularly advantageous where the drug is available in at least two different dosage forms (D1, D2) that differ by the drug concentration in a dose of the dosage form. Indeed, in such cases it may be particularly difficult to choose combinations of dosage forms that are appropriate without the use of the present invention. Further, the devices and methods of the present disclosure may be particularly advantageous when the drug is administered at regular intervals for prolonged periods of time. Indeed, when a drug is administered over prolonged periods of time, it is particularly important that inconveniences and disadvantages associated with administration of the drug are reduced as far as possible. A prolonged period of time may refer to a period of time over which multiple administrations of a drug are necessary to achieve a therapeutic or prophylactic effect associated with the drug. For example, the therapeutic of prophylactic effect associated with the drug may require a minimum concentration of the drug to be maintained in the patient (e.g. on plasma) over a predetermined period of time, requiring multiple separate administrations of the drug over said period of time. In some cases, the period of time may be the lifetime of the subject. In embodiments, the drug is administered for routine prophylaxis of a disease or condition. In embodiments, the condition is haemophilia and/or bleeding disorders. Further, the subject may be a human or animal subject. Typically, the subject may be a human subject.

The methods and devices of the disclosure are not limited as to the number of different dosage forms that are taken into account in the steps described herein, provided that a plurality of dosage forms (i.e. at least two dosage forms) are used. In particular, the drug may be available in three dosage forms (D1,D2, D3), four dosage forms (D1,D2, D3, D), five dosage forms (D1,D2, D3, D4, D5) or six dosage forms (D1,D2, D3, D4, D5, D6). At least two of the two, three, four, five or six dosage forms may differ from each other by the drug concentration in a dose of the dosage form.

In the context of the present disclosure, a subset may not be a strict (proper) subset, and may instead include all of the combinations in a set. For example, this may occur when all combinations in a set are equivalent when evaluated against a criterion used for selection.

Selecting a subset of the combinations ($A_t$ [D1,D2, D1D2]) that satisfy at least a first criterion and a second criterion may comprise selecting a first subset of the combinations ($A_t$ [D1,D2, D1D2]) according to a first criterion and selecting a second subset of the combinations from the first subset according to a second criterion different from the first criterion. As such, outputting the selected subset of combinations as the optimal administration regimen(s) for the subject may comprise outputting the last selected subset of combinations as the optimal administration regimen(s) for the subject. Further, selecting a subset of combinations according to a criterion may comprise ranking the combinations according to the criterion and selecting all combinations that have the best rank. Implementations based on successive selection of subsets (i.e. hierarchical or nested application of criteria) may be particularly simple and efficient. Further, implementations using ranking to select subsets of combinations may enable to keep track of combinations that are not selected, as the ranked list of combinations produced in a first selection may be used as a starting point for the second selection—for example by ranking the combinations according to a second criterion within ranks according to the first criterion.

The methods and devices of the disclosure are not limited as to the number of further criteria that are used in selecting successive subsets of combinations. Therefore, the selection of a subset of the combinations ($A_t$ [D1,D2, D1 D2]) that satisfy at least a first criterion and a second criterion may comprise the selection of a subset of combinations that satisfy a first, second and third criterion, a first, second, third and fourth criterion, etc. In particular, the computing device may be further configured to select a third (fourth, fifth, etc.) subset of the combinations from the second (third, fourth, etc.) subset according to a third (fourth, firth, etc.) criterion. In such cases, the last selected subset that is output would be the third (respectively fourht, fifth, etc.) subset. Similarly, the methods of the disclsoure may comprise further steps of selecting subsets from the previously selected subset, according to further criteria, and outputting the last of those successively selected subsets. In the context of this disclosure, a second criterion is a criterion that is different from the first criterion, a third criterion is a criterion that is different from the first and second criteria, etc.

In embodiments, amounts of drugs to be administered per elemental period of time (t) as a function of one or more parameters associated with the subject are provided as an input to the methods described herein. These may be stored in memory prior to the onset of the method and retrieved by the processor, or received by the processor as the value of at least one parameter associated with the subject. Further, these can be provided as one or more mathematical relationships linking one or more parameters associated with the subject to the amount of drug to be administered per elemental period of time (t). The at least one parameter may comprise the weight of the subject, and determining the amount of drug ($A_t$) to be administered to the subject per elemental period of time (t) may be based at least in part on the value received for the subject's weight. Relationships between an amount of drug to be administered per elemental period of time (e.g. per day, week or month) and the weight of a subject may be provided as an output of clinical trials, and these relationships may be used by the present method to automatically determine an amount of drug to be administered to a subject. For example, an amount of drug per kg (weight of the patient) per elemental period of time may be provided as an input to the methods described herein. Therefore, determining the amount of drug ($A_t$) to be administered to the subject per elemental period of time (t) based at least in part on the weight of a subject may comprise multiplying the weight of the subject by a preset (i.e. predetermined) amount of drug per elemental period of time (t). Further, multiple such preset amounts of drug per kg per elemental period of time may be provided as an input to the method, where the choice of such an amount depends on the value of another parameter associated with the patient (such as e.g. sex, age, disease severity/stage, etc.). In embodiments, the at least one parameter is the weight of the subject and one or more parameters associated with the subject are further received. These may be selected from the group comprising: the age of the subject, the sex of the subject, a disease-associated parameter, and a treatment associated parameter. A disease associated parameter may be an indication of the disease severity, identity, stage, co-occurrence of another disease or condition, etc. A treatment associated parameter may be an indication of another treatment that the subject is or has been undergoing. Therefore, the computing device may be configured to select a relationship between the weight of the subject and the amount of drug to be administered per elemental period of time (for example, from a set of relationships stored in memory), based on the value of at least one parameter received, and compute the amount of drug to be administered per elemental period of time according to the selected relationship, using the received value of the weight of the subject. For example, determining the amount of drug ($A_t$) to be administered to the subject per elemental period of time (t) based on at least the weight of a subject and a further parameter associated with the subject may comprise the processor retrieving from the memory a selected preset amount of drug per elemental period of time (t) depending on the value of the at least one further parameter associated with the subject, and multiplying the weight of the subject by the selected preset amount of drug per elemental period of time (t).

The inventors have further recognised that in some contexts, suitable administration regimens may be based on one of multiple intervals of time between administrations. In these contexts, more possibilities need to be considered which further increases the complexity of the problem, but also further increases the potential for particularly advantageous administration regimens to be identified. In order to accommodate and take advantage of this possibility, the computing device may further be configured to calculate, for one or more multiples (n) of the elemental period of time (t), the amount of drug ($A_{n1t}$, $A_{n2t}$) to be administered to the subject; and compute all minimal combinations of the at least two different dosage forms that can be used to achieve the amounts of drug ($A_{n1t}$, $A_{n2t}$) to be administered to the subject for each of the multiples (n) of the elemental period of time (t).

In embodiments, one or more suitable intervals between administrations (such as e.g. a maximum suitable interval between administrations) are provided as an input to the methods described herein. These may be stored in memory prior to the onset of the method and retrieved by the processor, or received by the processor as the value of at least one parameter associated with the subject. The one or more suitable intervals may be used to define the one more multiples (n) of the elemental period of time (t) that are suitable for use in the methods disclosed herein. For example, one or more amounts of drug to be administered per kg per week may be provided in combination with a maximum suitable interval of 4 weeks. In embodiments, the computing device is further configured to determine the multiples (n) of the elemental period of time (t) that are submultiples of a specific multiple (n) of the elemental period of time (t), where the specific multiple corresponds to a preset maximum interval between administrations. Advantageously, this means that the computing device may be able to automatically identify alternative dosage regimens that are within preset boundaries (such as e.g. boundaries that may have been previously set by clinical trials).

In embodiments, the computing device is further configured to obtain the one or more multiples (n) of the elemental period of time (t) by receiving them as a further parameter associated with the subject, or by retrieving them from memory. Similarly, the methods described herein may further comprise obtaining the one or more multiples (n) of the elemental period of time (t) by receiving them as a further parameter associated with the subject, or using one or more predetermined multiples (n) of the elemental period of time (t). This may be particularly useful when strict adherence to administration intervals determined from e.g. clinical trials is recommended for any reason (such as e.g. safety, regulatory, practical considerations associated with administration such as e.g. availability of trained staff, etc.).

In some cases, the drug is to be administered to the subject in multiple phases that together form a course of treatment, where the administration regimen may differ between the multiple phases. In such cases, two potentially different administration regimens may need to be determined for each subject, which may further complicate the task of the healthcare practitioner and may increase the risk of errors or suboptimal administration regimens being chosen. The devices and methods of the present disclosure may advantageously be able to handle these cases. For example, the drug may be administered according to a first administration regimen during a first phase that may be referred to as 'loading phase'. Following the loading phase, the drug may be administered according to a second administration regimen that may be referred to as 'maintenance phase'. The preset amount(s) of drug ($A_t$) to be administered to a subject per elemental period of time (t) and/or the one or more suitable intervals between administrations may differ between the different phases. In embodiments, the computing device may be configured to implement each of the steps of the method described herein for one or more of multiple phases that together form a course of treatment. For example, the computing device may be configured to determine the amount of drug ($A_t$) to be administered to a subject per elemental period of time (t) and define the one more multiples (n) of the elemental period of time (t) to be used based on preset values for a first phase (e.g. a loading phase), and based on preset values for a second phase (e.g. a maintenance phase). The computer may further be configured to compute all minimal combinations for the elemental period of time and any multiples (if applicable), and to select subsets of combinations, separately for each of the first and second phases. The selected subsets may be output together or separately for each of the first and second phases. Alternatively, a selection of a phase of treatment may be received as an input, based on which preset values for the amount of drug ($A_t$) to be administered to a subject per elemental period of time (t) and/or values for suitable intervals between administration may be selected.

Some of the steps of the methods of the present disclosure (and corresponding steps that the devices of the disclosure are configured to implement) may be performed prior to receiving the value of at least one parameter associated with the subject. For example, the amount(s) of drugs ($A_t$, $A_{nt}$) to be administered to a subject and optionally the minimal combinations that can be used to achieve these amounts may be pre-computed (e.g. by a processor and stored in memory), for a predefined set of values of parameters associated with a subject. In some such embodiments, the computing device may be configured to compute all minimal combinations of the at least two different dosage forms that can be used to achieve each of a predetermined set of amounts of drug ($A_t$, $A_{nt}$) to be administered to a subject. The computing device may further be configured to, upon receipt of the value of at least one parameter associated with the subject, determine the amount of drug ($A_t$) to be administered to the subject per elemental period of time (t) based at least in part on the value received, identify the closest total amount of drug ($A_t$, $A_{nt}$) in the pre-computed set of amounts of drug ($A_t$, $A_{nt}$) to be administered, and select subsets of combinations from the pre-computed combinations that can be used to achieve the identified closest amount of drug ($A_t$, $A_{nt}$). Alternatively, the computing device may be configured to determine the amount of drug ($A_t$) to be administered to a subject per elemental period of time (t) based at least in part on a predetermined set of values of the at least one parameter (such as e.g. the subject's weight), and compute all minimal combinations of the at least two different dosage forms that can be used to achieve each of the amounts of drug ($A_t$, $A_{nt}$) determined from the predetermined set of values of the at least one parameter. The computing device may further be configured to, upon receipt of the value of at least one parameter associated with the subject, identify the closest value in the predetermined set of values of the at least one parameter, and select subsets of combinations from the pre-computed combinations that can be used to achieve the amount of drug ($A_t$) corresponding to the closest value identified. Similarly, the computing device may further be configured to, upon receipt of the value of at least one parameter associated with the subject, compute the total amount of drug ($A_t$, $A_{nt}$) to be administered, select the closest amount of drug ($A_t$, $A_{nt}$) to be administered in the pre-computed set of amounts of drug ($A_t$, $A_{nt}$) to be administered, and select subsets of combinations from the pre-computed combinations that can be used to achieve the identified closest amount of drug ($A_t$, $A_{nt}$). Pre-computing the combinations may enable extensive checking of the combinations to be performed automatically and/or manually prior to the combinations being used to generate recommendations to a user. Further, pre-computing the combinations may result in an increased speed in providing the output to the user, upon receipt of a request comprising the value of at least one parameter associated with the subject.

As used herein, the term 'user' refers to a user of the methods and devices of the present disclosure. The user may be the subject themselves, or may be a person using the methods and devices of the disclosure in order to determine an administration regimen for a subject. In the latter case, the user may be a healthcare practitioner.

In alternative implementations, the steps of determining the amount of drug ($A_t$) to be administered to the subject per elemental period of time (t) and computing all minimal combinations that can be used to achieve the amount of drug ($A_t$) to be administered are performed upon receipt of the value of at least one parameter associated with the subject. Computing the combinations upon receipt of information about the subject may not require any assumptions to be made about the values of the at least one parameter to be used, and therefore may have increased flexibility and precision. For example, in embodiments where the at least one parameter comprises the subject's weight, precise weights can be used rather than the closest weight value In the set that was used to pre-compute combinations.

The selection of subsets of combinations may be performed separately for the elemental period of time (t) and each of the multiples (n) of the elemental period of time (t), or jointly for the elemental period of time (t) and all of the multiples (n) of the elemental period of time (t). When the selection is performed separately, outputting the (last) selected subset of combinations may comprise outputting the (last) selected subset of combinations for the elemental period of time (t) and for each of the multiples (n) of the elemental period of time (t). In other words, separate optimal administration regimen(s) may be provided for each of the different administration intervals (t, and each of the multiples n of t) that have been considered. This may advantageously present to the user an optimal solution for each of the administration intervals that they may want to use, where the user can then choose an administration interval that is most convenient, with the knowledge that they would be using the optimal regimen for that particular administration interval. In some such embodiments, the computing device is configured to output an indication of which of the selected administration regimen is optimal according to one of the criteria, preferably the first criterion, across the selected subsets for the elemental period (t) and each of the multiples (n) of the elemental period. This may advantageously enable the user to select a convenient administration interval based on their preferences in combination with the knowledge of whether some administration intervals could enable more advantageous administration regimens to be selected. For example, when multiple administration intervals are possible, it may not be immediately apparent that some of these administration intervals cannot be chosen without sacrificing performance against one of the criteria that may be of interest to a user. The methods and devices of the disclosure may be able to tackle such situations by outputting administration regimens that are optimal for each of the administration intervals, while also flagging up whether these "separately optimal" administration regimens (i.e. optimal across regimens for each administration interval separately) are "globally optimal" (i.e. optimal across all regimens considered).

The selection of the criteria to be used for any of the first, second, third, etc. selection may each be received as the value of one or more further parameters associated with the subject. For example, a criterion to be used as a first criterion may be received from a user. The second and optionally subsequent criteria may be selected by the user in a similar way, or default values (e.g. default criteria stored in memory) may be used. Further, the default values used for each of the second and subsequent criteria may be automatically selected based on the selection received for the first criterion. Further, the selection of the criteria may be from a predetermined set of criteria. For example, the method may comprise providing a predetermined set of criteria to a user and receiving a selection of one or more criteria from the predetermined set as the value of a further parameter associated with the subject.

Selecting a subset of combinations that satisfy to a first/second/third/etc. criterion may comprise calculating the value of a parameter associated with each combination and selecting the combination(s) that minimise or maximise the value of the calculated parameter. The combinations that minimise/maximise the value of a calculated parameter may be the combinations which are associated with the lowest/highest value of the calculated parameter in the set of combination from which the subset is selected. Some tolerance may be included in this selection, such that combinations that are associated with a value of the parameter within a predetermined distance of the lowest/highest value of the parameter in the set of combinations may be selected for inclusion in the subset that minimises/maximises the value of the parameter. For example, the value of a parameter associated with a combination may include the wastage associated with the combination, the number of physical administration steps required to administer a combination, the number of physical preparative steps associated with administration of a combination, or any combination or derivative of the above.

In embodiments, the method comprises computing the wastage associated with a combination of dosage forms ($W_t$ [D1,D2, D1D2]; $W_{n1t}$[D1,D2, D1D2]; $W_{n2t}$ [D1,D2, D1D2]) as the difference between the total amount of drug in the combination of dosage forms and the amount of drug ($A_t, A_{n1t}, A_{n2t}$) to be administered to the subject. The method may further comprise computing the total wastage as the wastage per period of time. Computing the total wastage (wastage per period of time) may comprises computing the wastage per elemental period of time t. This may be achieved by dividing the wastage for each combination by its corresponding multiple (n), where n=1 for combinations corresponding to the elemental period (t). In other embodiments, computing the total wastage (wastage per period of time) comprises computing the total wastage over a period of time corresponding to the lowest common multiple of the multiples (n). The wastage associated with an administration regimen may be a particularly useful parameter to compute when the drug is expensive, difficult to source and/or difficult to dispose of leftovers. Further, keeping track of the wastage in terms of amount of drug may be particularly advantageous when some of the dosage forms differ by their concentrations. Indeed, in such cases it may not be immediately apparent which administration regimens are associated with the lowest wastage, even if one could determine the amount of dosage form that is being used according to each administration regimen. Further, computing the total wastage (wastage per comparable period of time, be it the elemental period of time or a common multiple of the different multiples n considered) may be particularly advantageous since it enables to determine administration regimen that are optimal over repeated administrations. This may not be immediately apparent from the parameters of single administrations, and may be particularly advantageous for drugs that are administered over prolonged periods of time. Therefore, in embodiments one of the criteria used for selecting subsets applies to the value of total wastage (wastage per period of time) associated with each combination, and the selected combinations are those that minimise this parameter.

Instead or in addition to computing the wastage, the total number of physical administration steps required to administer a combination may be computed, and this may be used as one of the criteria used to select subsets of combinations. Computing the total number of physical administration steps required to administer a combination may comprise computing the minimum number of physical administration steps that can be used to administer a combination and that satisfy one or more rules selected from: a preset maximum amount of drug for each physical administration step, a preset maximum amount of dosage form for each physical administration step, and a restriction on the combination of dosage forms that differ by their concentration in a single physical administration step. Further, the rules on the preset amount of drug/dosage form for each physical administration step may apply differently depending on the precision required to administer a particular amount. For example, amounts specified with a particular precision may be associated with a different preset maximum amount of drug/dosage form than amounts specified with another, lower particular precision. Each of these rules may be predetermined (e.g. stored in memory) or may be received as further parameter(s) associated with the subject. Further, the choice of one or more such predetermined rules may be based on the value of one or more parameters associated with the subject. For example, two or more predetermined maximum amounts of dosage form for each physical administration step may be available, and selection of one of these amounts may depend on parameters such as the weight of the subject, the age of the subject, a disease related parameter, etc. The number of physical administration steps required to administer a combination may be a particularly useful parameter to consider when the drug is difficult, painful or inconvenient to administer. Further, the total number of physical administration steps required to administer a combination may not be immediately apparent from the combination, especially where multiple rules must be taken into account when determining the number of separate physical administration steps required to administer the combination. In such cases, the automated computation of the total number of steps required for administration, and the comparison of combinations on this basis may advantageously enable the selection of combinations that may not have intuitively appeared to be preferable due to the complexity of the factors to be taken into account when administering a combination. Therefore, in embodiments one of the criteria used for selecting subsets applies to the value of the total number of physical administrations steps associated with each combination, and the selected combinations are those that minimise this parameter.

A preset maximum amount of drug for each physical administration step may be specified as a weight of the drug or as a number of units of the drug. A preset maximum amount of dosage form for each physical administration step may be specified as a weight of the dosage form or as a volume of the dosage form. In embodiments, the dosage form is a liquid formulation. For example, the dosage form may be a solution, a suspension, or any other type of liquid formulation. A single physical administration step of a liquid formulation may be a single injection of a volume of dosage form. In some embodiments, each single injection has a pre-set maximum volume selected from a group comprising two pre-set maximum volumes ($V_1$, $V_2$). In some embodiments, each single injection has a pre-set maximum volume selected from a group comprising three pre-set maximum volumes ($V_1$, $V_2$, $V_3$). In some embodiments, the computing device is further configured to prioritise administration regimens that do not combine single injections with different maximum volumes. For example, when computing the number of physical administration steps associated with a combination, the computing device may associate with a combination the lowest possible number that does not use different maximum volumes. This may be useful to reduce the number of different syringes that are used. In embodiments, a single physical administration step can be a single ingestion of a volume of dosage form that is a liquid formulation. In embodiments, a single physical administration step can be a unit of time necessary to administer a volume of dosage form as a liquid formulation by intravenous means using e.g. a drip. In embodiments, the dosage form is a solid (e.g. tablet, powder, etc.) or encapsulated formulation. In some such embodiments, a single physical administration step can be a single ingestion of a weight or volume of dosage form, or of one or more capsules or tablets.

Instead or in addition to computing the wastage and/or the total number of physical administration steps required to administer a combination, the total number of physical preparative steps required to administer a combination may be computed. This may also be used as one of the criteria applied to select subsets of combinations. Computing the total number of physical preparative steps required to administer a combination may comprise computing the number of doses of each of the dosage forms that make up a combination. The number of physical preparative steps may be proportional to the number of doses of each dosage form as for each administration, each dose may have to be extracted from its packaging and optionally placed in a form suitable for administration (such as e.g. drawn in a syringe for injection, poured in a container for ingestion, etc.) The total number of physical administration steps required to administer a combination may be particularly useful to consider where administration requires complex, error and/or waste-prone preparative steps. For example, where the dose of a dosage form has to be placed in a form suitable for administration by heating, pouring, diluting, disolving, etc., each such step may be associated with a risk of error, waste, contamination, etc. Further, the number of preparative steps may not be identical to the number of administrations, since multiple doses of a dosage form may be suitable for administration in a combined form. Similary to the number of administration steps, the number of preparative steps and how these compare across combinations may not be intuitive. Therefore, there may be particular value in taking either or both parameters into account. As such, in embodiments one of the criteria used for selecting subsets applies to the value of the total number of physical preparative steps associated with each combination, and the selected combinations are those that minimise this parameter.

In addition to the parameters that are used to evaluate combinations against the criteria used for selecting subsets of combinations, further information about each combination may advantageously be computed, and optionally output to the user. These may include one or more of: the wastage associated with the combination (as an amount of drug and/or an amount of dosage form, combined across dosage forms in the combination and/or for each dosage form in the combination separately); the total wastage associated with the combination (as an amount of drug and/or an amount of dosage form combined across dosage forms in the combination and/or for each dosage form in the combination separately); the number of doses of each dosage form; the total number of doses across dosage forms; the amount to be used from each dosage form (as an amount of drug and/or an amount of dosage form) and/or from each dose of each dosage form; the amounts of each dosage form and/or of each dose of each dosage form to be used for each physical administration step; the number of physical administration steps; any parameters of material required for administration, for example, when a dosage form is a liquid formulation for injection, the volume of injection device to be used for each physical administration step, and/or the number of syringes to be used.

Further, at least one of the above parameters may be computed in at least two ways, and the results of these computations may be compared to identify any inconsistencies. For example, the computing device may be configured to: compute the total amount of each dosage form that is used and the total wastage, and compare the total wastage and the total amount of each dosage form, in order to check that the amounts are compatible with multiples of the dosage forms used. A warning or error may further be produced where inconsistencies have been detected.

In embodiments, a user interface may be provided through which a user may be able to input information including the value of at least one parameter associated with the subject. Similarly, outputting one or more optimal administration regimen(s) may comprise providing information that identifies the one or more optimal administration regimen(s) to a user via the user interface. The user interface may form part of the computing device that is configured to implement the methods described herein, or may form part of a second computing device with which the computing device configured to implement the methods described herein is configured to communicate. For example, a computing device according to the disclosure may be configured to communicate with a second computing device, such that the computing device receiving the value of at least one parameter associated with a subject comprises the computing device receiving information from the second computing device (which information may have been input by a user via a user interface of the second computing device), and the computing device outputting one or more optimal administration regimen(s) comprises the computing device communicating information identifying the one or more optimal administration regimen(s) to the second computing device (which the second computing device may be able to provide to the user via a user interface of the second computing device). Embodiments where the same computing device implements the methods described herein and receives input/provides output through a user interface of the computing device may advantageously perform all computations locally. As such, they may not require e.g. a connection to a network to provide results, and may not need to share data across a public network. Conversely, embodiments where the computing device implementing the method is remote from the computing device associated with a user interface may advantageously enable the tools of the present disclosure to be provided by a centrally maintained computing system (such as e.g. a server). The ability to centrally maintain the computing system implementing the method may ensure that the methods use up to date information, and that appropriate computing power is dedicated to make the necessary computations. Further, such implementations may be simpler to provide as cross-platform implementations as they can be provided for example as a web application, rather than platform-specific applications.

Also provided is a device for automatically determining an administration regimen of a drug to a subject, the device comprising a processor and a memory, wherein the memory stores instructions that, when executed by the processor, cause the processor to implement the steps of the methods described herein. In particular, the instructions may cause the processor to: receive the value of at least one parameter associated with the subject; determine the amount of drug $(A_t)$ to be administered to the subject per elemental period of time (t) based at least in part on the value of the at least one parameter associated with the subject, wherein the drug is available in at least two different dosage forms (D1,D2) that differ by the total amount of drug and/or the drug concentration in a dose of the dosage form; compute all minimal combinations ($A_t$ [D1,D2, D1D2]) of the at least two different dosage forms that can be used to achieve the amount of drug $(A_t)$ to be administered to the subject, wherein a minimal combination is a combination that reaches or exceeds the amount of drug $(A_t)$ to be administered to the subject by using the minimum number of doses of each dosage form in a combination of dosage forms (D1, D2, D1D2); select a subset of the combinations ($A_t$ [D1,D2, D1D2]) that satisfy at least a first criterion and a second criterion; and output the selected subset of combinations as the optimal administration regimen(s) for the subject. The device may have any of the features described above.

The devices of the invention may comprise a server or a personal computing device. A personal computing device may be a mobile device, such as a mobile phone or tablet.

According to a further aspect, a computer readable medium is provided, recording instructions that, when executed by a processor, cause the processor to implement the steps of the methods described herein. In particular, the instructions may cause the processor to receive the value of at least one parameter associated with the subject; determine the amount of drug $(A_t)$ to be administered to the subject per elemental period of time (t) based at least in part on the value of the at least one parameter associated with the subject, wherein the drug is available in at least two different dosage forms (D1,D2) that differ by the total amount of drug and/or the drug concentration in a dose of the dosage form; compute all minimal combinations ($A_t$ [D1,D2, D1D2]) of the at least two different dosage forms that can be used to achieve the amount of drug $(A_t)$ to be administered to the subject, wherein a minimal combination is a combination that reaches or exceeds the amount of drug $(A_t)$ to be administered to the subject by using the minimum number of individual doses of each dosage form for each combination of dosage forms (D1, D2, D1D2); select a subset of the combinations ($A_t$ [D1,D2, D1D2]) that satisfy at least a first criterion and a second criterion; and output the selected subset of combinations as the optimal administration regimen(s) for the subject.

Also provided herein is a method of treating a subject with a drug comprising the steps of: automatically (e.g. by a processor) determining an administration regimen of the drug to the subject, by: receiving the value of at least one parameter associated with the subject; determining the amount of drug $(A_t)$ to be administered to the subject per elemental period of time (t) based at least in part on the value of the at least one parameter associated with the subject, wherein the drug is available in at least two different dosage forms (D1,D2) that differ by the total amount of drug and/or the drug concentration in a dose of the dosage form; computing all minimal combinations ($A_t$ [D1,D2, D1D2]) of the at least two different dosage forms that can be used to achieve the amount of drug $(A_t)$ to be administered to the subject, wherein a minimal combination is a combination that reaches or exceeds the amount of drug $(A_t)$ to be administered to the subject by using the minimum number of doses of each dosage form in a combination of dosage forms (D1,D2, D1D2); selecting a subset of the combinations ($A_t$ [D1,D2, D1D2]) that satisfy at least a first criterion and a second criterion; and outputting the selected subset of combinations as the optimal administration regimen(s) for the subject; and treating the subject with the optimal administration regimen (or one of the optimal administration regimens) for the subject. Embodiments of this aspect may include any of the features described in relation to any other aspect.

Still further, the invention provides a computer program stored on a medium, for executing, in cooperation with hardware, the steps of: receiving the value of at least one parameter associated with the subject; determining the amount of drug $(A_t)$ to be administered to the subject per elemental period of time (t) based at least in part on the value of the at least one parameter associated with the subject, wherein the drug is available in at least two different dosage forms (D1, D2) that differ by the total amount of drug and/or the drug concentration in a dose of the dosage form; computing all minimal combinations ($A_t$ [D1,D2, D1D2]) of the at least two different dosage forms that can be used to achieve the amount of drug $(A_t)$ to be administered to the subject, wherein a minimal combination is a combination that reaches or exceeds the amount of drug ($A_t$) to be administered to the subject by using the minimum number of individual doses of each dosage form in a combination of dosage forms (D1, D2, D1D2); selecting a subset of the combinations ($A_t$ [D1,D2, D1D2]) that satisfy at least a first criterion and a second criterion; and outputting the selected subset of combinations as the optimal administration regimen(s) for the subject.

Figure 1:
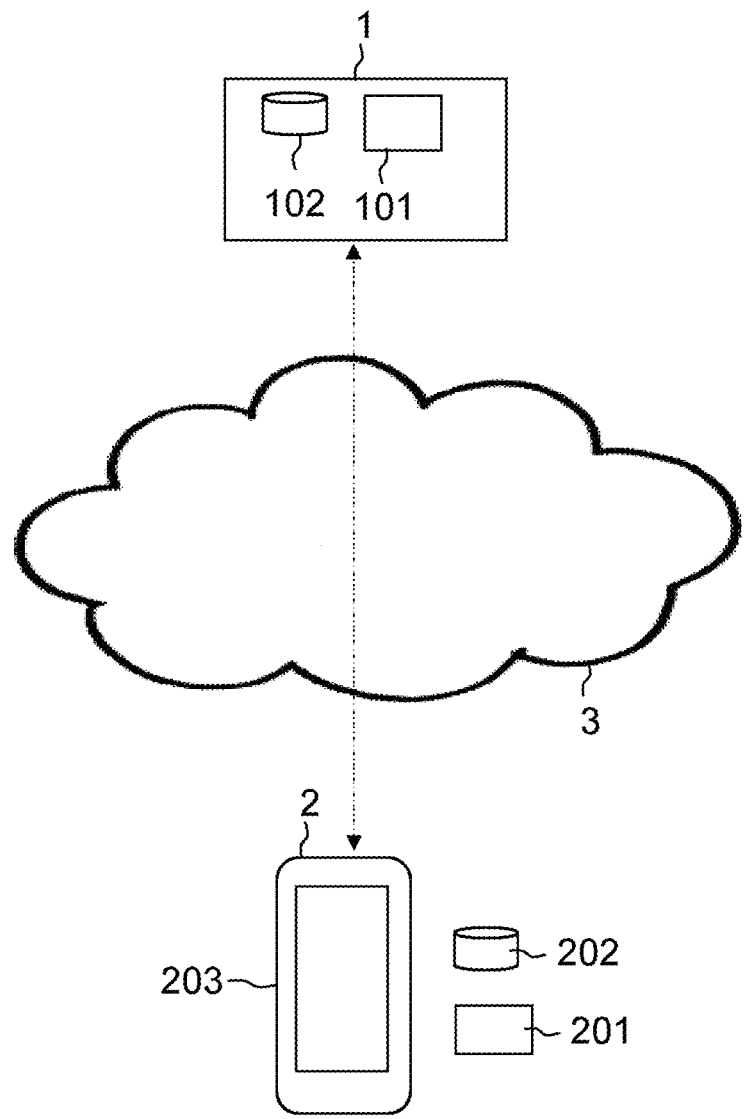
FIG. 1 shows an exemplary computing system in which embodiments of the present invention may be used.

Where the figures laid out herein illustrate embodiments of the present invention, these should not be construed as limiting to the scope of the invention. Where appropriate, like reference numerals will be used in different figures to relate to the same structural features of the illustrated embodiments.

DETAILED DESCRIPTION

Specific embodiments of the invention will be described below with reference to the Figures.

FIG. 1 shows an exemplary computing system in which embodiments of the present invention may be used.

A first computing device 1 is shown in FIG. 1. The first computing device 1 may for example form part of a service provider computing system, and as such is also referred to herein as 'service provider computing device'. The first computing device 1 comprises one or more processors 101 (e.g. servers), and one or more memories 102. The first computing device may further comprise a plurality of switches (not shown). A user (not shown) is provided with a user computing device (also referred to herein as 'second computing device') 2. This may be a mobile computing device such as a mobile phone, a personal computer, etc. The computing device 2 has at least one processor 202 and at least one memory 201 together providing at least one execution environment. Typically, a mobile device has firmware and applications run in at least one regular execution environment (REE) with an operating system such as iOS, Android or Windows. The computing device 2 may also be equipped with means 203 to communicate with other elements of a computing infrastructure, for example via the public internet 3. These may for example comprise a wireless telecommunications apparatus for communication with a wireless telecommunications network, local wireless communication apparatus to communicate with the public internet 3 using e.g. Wi-Fi technology, and/or a wired communication interface to connect to the public internet 3. The second computing device 2 comprises a user interface 204 which typically includes a display. The display 204 may be a touch screen. Other types of user interfaces may be provided, such as e.g. a speaker, keyboard, one or more buttons (not shown), etc. The second (user) computing device 2 can be connected to the first (service provider) computing device 1 by a network connection, such as via the public internet 3.

In embodiments, the first computing device 1 is configured to determine an administration regimen of a drug to a subject. In such embodiments, the memory 101 may store instructions that, when executed by the processor 102, cause the processor to execute the steps of a method of determining an administration regimen of a drug to a subject, as described herein. In such embodiments, the first computing device 1 may be configured to receive information from a user computing device 2, for example over the public internet 3. The first computing device 1 may further be configured to output information to a user computing device 2, for example over the public internet 3. The information can then be displayed by the user computing device 2, for example using display 204. For example, the processor 101 may comprise one or more servers, and the method may be implemented as a webpage, a web application or a progressive web application. In embodiments, the method is implemented as a progressive web application that runs on the first computing device 1, and is delivered to the second computing device 2 through the public internet 3.

In other embodiments, the second computing device 2 is configured to determine an administration regimen of a drug to a subject. In such embodiments, the memory 201 may store instructions that, when executed by the processor 202, cause the processor to execute the steps of a method of determining an administration regimen of a drug to a subject, as described herein. In such embodiments, the second computing device 1 may be configured to receive information via its user interface 204, upon input from a user. The second computing device 2 may further be configured to output information to a user, for example via the user interface 204. In such embodiments, the method may be implemented as an application that runs locally on the processor 202.

As the skilled person would understand, alternative implementations are possible. For example, the processor 102 may be configured to execute the steps of a method of determining an administration regimen of a drug to a subject, as described herein, and the method may be accessed via a native application that runs locally on the second computing device 2 and sends a query to the first computing device 1.

Figure 2:
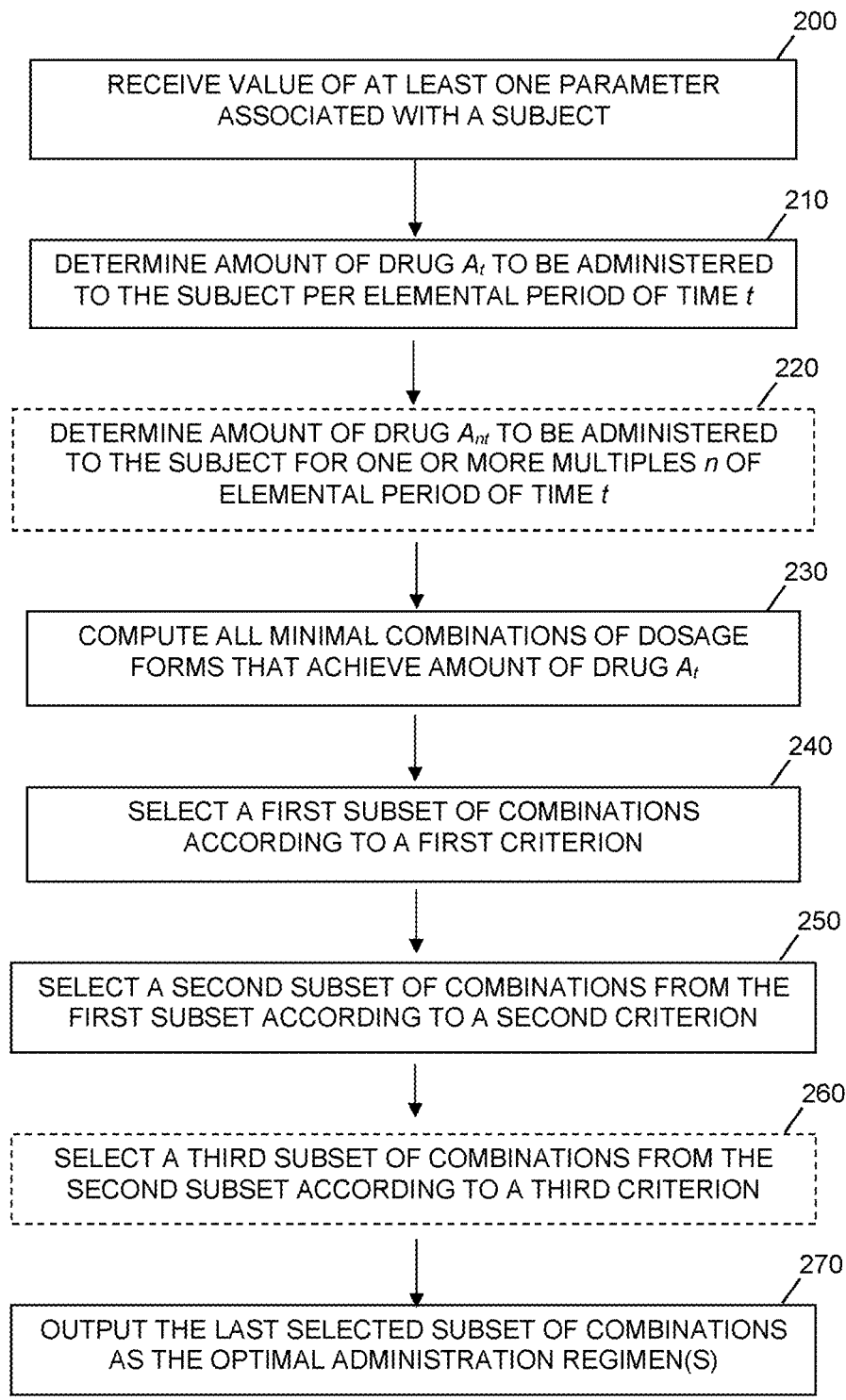
FIG. 2 is a flow chart illustrating a method of determining an administration regimen of a drug to a subject.

FIG. 2 shows a general embodiment of a method of determining an administration regimen of a drug to a subject. The methods and device of the present invention find use in situations where a drug is available in at least two different dosage forms (D1, D2) that differ by the total amount of drug and/or the drug concentration in a dose of the dosage form.

At step 200, the value of at least one parameter associated with the subject is received (for example by the processor 102 or the processor 202). The at least one parameter may be the weight of the subject. The value of one or more additional parameters may also be received at step 200. These may include one or more user preferences. User preferences may include for example a selection of one or more criteria to be use in the determination of the most suitable drug regimen for the subject, as will be discussed further below. User preferences may include a selection of one or more administration frequencies (multiples of an elemental period of time for administration, as will be discussed further below). The one or more further parameters associated with the subject may instead or in addition be selected from the group comprising: the age of the subject, the sex of the subject, a disease-associated parameter, and a treatment associated parameter. A disease associated parameter may be an indication of the disease severity, identity, stage, co-occurrence of another disease or condition, etc. A treatment associated parameter may be an indication of another treatment that the subject is or has been undergoing. The values of one or more parameters may be entered by a user at a user interface 204, and communicated to the processor 102/202.

At step 210, the amount of drug ($A_t$) to be administered to the subject per elemental period of time (t) is determined based at least in part on the value of the at least one parameter associated with the subject. The amount of drug to be administered per elemental period of time (t) and the one or more administration frequencies that are suitable to achieve a desired prophylactic or therapeutic effect for a drug may be pre-defined, for example through clinical trials, as known in the art. In embodiments, appropriate (such as e.g. safe and effective) amounts of drugs to be administered per elemental period of time (t) as a function of one or more parameters associated with the subject are provided as an input to the methods described herein. For example, these may be stored in the memory 101/201. These can be provided as one or more mathematical relationships linking one or more parameters associated with the subject to the safe and effective amount of drug to be administered per elemental period of time (t). For example, an amount of drug per kg (weight of the patient) per elemental period of time may be provided as an input to the methods described herein. Further, multiple such amounts of drug per kg per elemental period of time may be provided, where the choice of such an amount may depend on the value of another parameter associated with the patient (such as e.g. sex, age, disease severity/stage, etc.). Therefore, step 210 may comprise the processor 102/202 retrieving from memory 101/201, a relationship linking one or more parameters associated with the subject to the (e.g. safe and effective) amount of drug to be administered per elemental period of time (t). Further, the choice of the relationship that is retrieved, where multiple such relationships are stored in memory 101/201 may depend on the value of at least one parameter received at step 200. Step 210 may further comprise the processor 102/202 applying the mathematical relationship to the value of the at least one parameter (e.g. the subject's weight) received in step 200. Preferably, the at least one parameter comprises the subject's weight, and determining the amount of drug ($A_t$) to be administered to the subject per elemental period of time (t) based at least in part on the weight of a subject comprises the processor 102/202 multiplying the weight of the subject by a preset amount of drug per elemental period of time (t). The elemental period of time t that is used may depend on the particular drug used, such as for example the minimum interval between administrations that has been assessed in clinical trials. In embodiments, the elemental period of time t is selected from a day, a week and a month. In embodiments, n is 2 and 4 and the elemental period is a week.

A further optional step 220 may be performed, in which the amount of drug ($A_{n1t}$, $A_{n2t}$) to be administered to the subject is calculated for one or more multiples (n) of the elemental period of time (t). The one or more multiples (n) can be received at step 200 as a further parameter associated with the subject (i.e. as a user preference). In embodiments, value(s) of one or more multiples (n) can be stored in the memory 101/201. These can be retrieved by the processor 102/202 and used in step 220 (as default values), or they can be used to check that one or more values of n received at step 200 are compatible with the present method. For example, a maximum value of n may be stored in memory, and the processor 102/202 may at step 220 verify that any value of n received in step 200 is a submutliple of the maximum value stored in memory. The multiples n are typically integer multiples, since administration schedules that are counted in entire days, weeks or months are more common. However, the present method is not in principle limited to this. Further, the amount of drug ($A_{n1t}$, $A_{n2t}$) to be administered to the subject may be calculated for one or more multiples (n) of the elemental period of time (t) by multiplying the amount of drug per elemental period of time $A_t$ by each value of n. Alternatively, the amount of drug ($A_{n1t}$, $A_{n2t}$) to be administered to the subject may be calculated for one or more multiples (n) of the elemental period of time (t) by retrieving from memory 101/201 a mathematical relationship between the value of the at least one parameter associated with the subject and the amount of drug to be administered per period of time n*t. For example, one or more amounts of drug to be administered per kg per week may be stored in memory in combination with a maximum suitable interval of 4 weeks. These may be used to calculate an amount of drug to be administered to a subject every week, every 2 weeks or every 4 weeks, depending on the subject's weight. As the skilled person would understand, it is also possible for the mathematical relationship between the amount of drug and the value of at least one parameter associated with the subject to be provided by the user prior to the implementation of step 210, and stored in memory 101/201 for use in steps 210, 220.

At step 230, all minimal combinations of at least two dosage forms of the drug that can be used to achieve the amount of drug ($A_t$) to be administered to the subject (and each of the amounts $A_{n1t}$, $A_{n2t}$, if applicable) are computed. For example, processor 102/202 may compute all possible minimal combinations and store these in memory 101/201. A minimal combination is a combination that reaches or exceeds the amount of drug ($A_t$) by using the minimum number of individual doses of each dosage form for each combination of dosage forms (D1, D2, D1D2). For example, for a drug that is available in two dosage forms D1 and D2, three types of combinations are possible to achieve any dose: D1 alone, D2 alone, D1 and D2. If D2 contains half the amount of drug of D1, and a total dose of 2*D1 is required, then the minimal combinations are: 2*D1 (i.e. two doses of dosage form D1), 4*D2 (i.e. four doses of dosage form D2), 1*D1+2*D2 (i.e. one dose of dosage form D1 and two doses of dosage form D2). In other words, for each of the three types of combinations, the minimal combinations are those that include the minimum number of doses that achieves the amount while having the dosage form in the set. For D1 alone, this is the minimum number of doses of D1 that achieves $A_t$. For D2 alone, this is the minimum number of doses of D2 that achieves $A_t$. For D1+D2, these are the minimum combinations of doses that include both D1 and D2 (i.e. at least one D1 and one D2 must be used) and that achieve $A_t$. There may be multiple minimal combinations in types combining different dosage forms, for some amounts $A_t$ and some dosage forms D1, D2 (since for example some amounts $A_t$ could be reached using 1*D1+2*D2 or using 2*D1+1*D2). In embodiments, depending on the amount $A_t$ required, some types of combinations may not be represented in the minimal combinations computed at step 230, because the amount $A_t$ is lower than the amount of drug contained in at least one of the dosage forms. For example, if $A_t$ is smaller than the amount of drug contained in a dose of dosage form D1 or D2, then the D1D2 combinations may not be generated. In embodiments, the amounts of drug contained in each of the dosage forms (D1, D2) may be stored in memory 101/201 and retrieved by the processor 102/202. Alternatively, the amounts of drug contained in each of the dosage forms (D1, D2) may be provided by the user prior to the processor 102/202 implementing step 230.

In embodiments, the drug is to be administered to the subject in multiple phases that together form a course of treatment, where the administration regimen may differ between the multiple phases. For example, the drug may be administered according to a first administration regimen during a first phase that may be referred to as 'loading phase', following which the drug may be administered according to a second administration regimen that may be referred to as 'maintenance phase'. The amount(s) of drug ($A_t$) to be administered to a subject per elemental period of time (t) and/or the one or more suitable intervals between administrations may differ between the different phases of treatment. In embodiments, each of steps 210, 220 and 230 may be implemented for one or more of multiple phases that together form a course of treatment. In embodiments, a choice of treatment phase may be received as a parameter in step 200, and steps 210, 220 and 230 may be implemented accordingly.

At steps 240, 250 (and 260, if applicable), a subset of the combinations ($A_t$ [D1,D2, D1D2]) that satisfy at least a first criterion and a second criterion is selected. In this particular implementation, at step 240, a first subset of the combinations ($A_t$ [D1,D2, D1D2]—and $A_{n1t}$ [D1,D2, D1D2]; $A_{n2t}$ [D1,D2, D1D2], if applicable) generated at step 230 is selected according to a first criterion. For example, the processor 102/202 may evaluate the combinations calculated at step 230 and stored in memory 101/201 against a first criterion, select a first subset of the combinations based on the evaluation, and store the first subset in memory 101/201. Selecting a subset of combinations that satisfy a first criterion may comprise computing the value of a parameter associated with the combinations, and selecting the combinations that maximise or minimise the parameter. Alternatively, the combinations that have a value above or below a predetermined threshold for the calculated parameter may be selected. Yet further, the combinations that have a value within a certain distance of the maximum/minimum value across all combinations may be selected. As the skilled person would understand, depending on the combinations and criteria used, the subset may in fact comprise all combinations, for example where all combinations satisfy the criteria (for example because the value of the parameter is identical for all combinations, or within a certain distance of the minimum/maximum value of the parameter across all combinations evaluated). Selecting a subset of combinations may be performed for example by ranking the combinations according to the criterion, and selecting all combinations that have the joint best rank. In embodiments where combinations are calculated for one or more values of n (in addition to n=1), the selection may be performed separately for the elemental period of time (t) and each of the multiples (n) of the elemental period of time (t). Alternatively, the selection may be performed jointly for the elemental period of time (t) and each of the multiples (n) of the elemental period of time (t).

At step 250, a second subset of the subset of combinations ($A_t$ [D1,D2, D1D2]—and $A_{n1t}$ [D1,D2, D1D2]; $A_{n2t}$ [D1,D2, D1D2], if applicable) selected at step 240 is selected according to a second criterion. Selection of a second subset from the first subset may be performed as explained above in relation to step 240. For example, the processor 102/202 may evaluate the combinations calculated at step 230 (or only the subset selected at step 240) and stored in memory 101/201 against a second criterion (for example by computing the value of a second parameter associated with the combinations), select a second subset of the combinations in the first subset based on the evaluation, and store the second subset in memory 101/201.

At optional step 260, a third subset may be selected from the second subset, according to a third criterion. Selection of a third subset from the second subset may be performed as explained above in relation to step 240. For example, the processor 102/202 may evaluate the combinations calculated at step 230 (or only the subset selected at step 240, or the subset selected at step 250) and stored in memory 101/201 against a third criterion, select a third subset of the combinations in the second subset based on the evaluation, and store the third subset in memory 101/201. As the skilled person would understand, any number of further criteria may be used to hierarchically select subsets of previously selected subsets. For example, a fourth subset may be selected from the third subset using a fourth criterion, a fifth subset may be selected from the fourth subset using a fifth criterion, etc.

In embodiments, the further parameter received at step 200 comprises a selected criterion. In such embodiments, the criterion can be used as the first criterion for selection of administration regimens, in combination with one or more preset further criteria that may be stored in memory 101/201. For example, the second and any further criteria (if used) may be selected automatically based on the criterion received at step 200. In other words, the memory 101/201 may store default criteria to be used in combination with selected first criterion, and the processor 102 or 202 may retrieve the value of this parameter from memory 101/201, based on the values received at step 200. Similarly, step 200 may comprise receiving at least two further parameters including a first criterion and a second criterion. These may be used in combination with a third criterion that may be set as a default parameter stored in memory 101/201. Step 200 may also comprise receiving at least three further parameters including a first criterion, a second criterion and a third criterion. In embodiments, default selections may be stored in the memory 201/101 for all criteria including the first criterion.

Parameters associated with the combinations that may be computed to select subsets of combinations may include one or more of: the wastage associated with a combination of dosage forms, the total wastage per period of time, the total number of physical administration steps required to administer a combination, and the total number of physical preparative steps required to administer a combination. The total wastage per period of time may be calculated as the total wastage per elemental period of time, and/or the total wastage over a period of time corresponding to the lowest common multiple of the multiples (n). The total wastage per elemental period of time may be calculated by dividing the wastage for each combination by its corresponding multiple n, where n=1 for combinations corresponding tote elemental period (t). The total wastage over a period of time corresponding to the lowest common multiple of the multiples (n) may be calculated by multiplying the wastage for each combination by the multiplier needed to reach the lowest common multiple based on the multiple n associated with the combination. For example, for n=2 and n=4, the lowest common multiple is 4, and the total wastage can be calculated in this embodiment over 4 elemental time periods. This may be achieved by multiplying the wastage for each combination for the elemental time period by 4, and the wastage for each combination for the n=2 multiple of the elemental time period by 2. The total number of physical administration steps required to administer a combination may be calculated as the minimum number of physical administration steps that can be used to administer a combination and that satisfy one or more rules. The rules and any other parameter of the dosage forms D1, D2 that may be necessary to apply the rules may be stored in memory 101/201 and retrieved by the processor 102/202 in order to calculate the total number of physical administration steps. The total number of physical preparative steps required to administer a combination may be calculated as the number of doses of each of the dosage forms that make up a combination. Where multiple preparative steps apply for some of the dosage forms, this may be stored in memory 101/201 as a parameter of the dosage forms D1, D2 and retrieved by the processor 102/202 in order to calculate the total number of physical preparative steps by multiplying the number of doses of each dosage form by the corresponding number of physical preparative steps.

At step 270, the (last) selected subset of combinations is output as the optimal administration regimen(s) for the subject according to the first and second (and optionally third or further criteria). In embodiments, outputting the optimal administration regimens may comprise the processor 202 causing information identifying the one or more optimal administration regimen(s) to be displayed on the user interface 204. For example, the processor 102 may communicate information identifying the one or more optimal administration regimen(s) to the processor 202, which may cause it to be displayed on user interface 204. Alternatively, the processor 202 may be able to perform at least some of the computations above locally, and may therefore select the combinations and output the information identifying the selected combinations as the optimal administration regimen(s). In embodiments, a single optimal administration regimen (i.e. combination of dosage forms) may be output. In embodiments, multiple optimal administration regimens (i.e. combinations of dosage forms) may be output. In embodiments, a single optimal administration regimen may be output for the elemental period of time (t) and each of the multiples (n) of the elemental period of time. In embodiments where multiple optimal administration regimens are output, an indication of which of the output administration regimen is optimal according to one of the criterion may also be output. For example, the multiple optimal administration regimens may be output together with an indication of which of these multiple optimal administration regimens optimise the first criterion. For example, when an optimal administration regimen is output for each of the multiples n separately, these may not all be optimal across all combinations for all administration intervals. In such cases, it may be useful to include an indication of which of these are optimal according to a criterion, such as e.g. the first criterion.

Outputting a combination comprises providing information identifying the combination, comprising the identity and number of the dosage forms that make up the combination. If applicable, the information identifying the combination may further comprise the administration interval (t, n*t). The information identifying the combination is provided to a user via a user interface, or to a user device for providing to a user via a user interface. The user interface may be provided for example as a webpage displayed on a user device. In such embodiments, the user may be able to input information such as by typing or selecting items, causing the user device to obtain information from a server in the form of a new webpage.

Additional parameters associated with an output administration regimen may also be computed and optionally output at step 270. These parameters may include one or more of: the wastage associated with the combination, the total wastage associated with the combination, the amount to be used from each dosage form, the amounts of each dosage form to be used for each physical administration step, etc. When the drug is a liquid formulation for injection, these parameters may further include the volume of injection device (e.g. syringe) to be used for each physical administration step. Advantageously, at least one of the above parameters may be computed in at least two ways, and the results of the computations may be compared to ensure that they are consistent. Further, at least two of the above parameters may be computed by the processor 102/202, in order to check that the at least two values are consistent. For example, the processor 102/202 may compute the total amount of each dosage form that is used and the total wastage, and compare the total wastage and the total amount of each dosage form to check that the amounts are compatible with multiples of the dosage forms used.

As the skilled person would understand, the general principles above are applicable to situations where the drug is available in three or more dosage forms (such as e.g. four, five or six dosage forms). For example, where the drug is available in four different dosage forms (D1, D2, D3, D4), 15 types of minimal combinations may be considered: D1, D2, D3, D4, D1D2, D1D3, D1D4, D2D3, D2D4, D3D4, D1D2D3, D1D2D4, D2D3D4, D1D3D4, and D1D2D3D4. As explained above, depending on the amount of drug $A_t$ that is required, and the amount of drug contained in each of the dosage forms, not all types of combinations may be represented. For example, if $A_t$ is smaller than the amount of drug in D4, then the minimal combinations comprising D4 in combination with any other dosage form may not be computed. In embodiments, any two of the three or more dosage forms may differ by the total amount of drug in a dose of the dosage formulation. Similarly, any two of the three or more dosage forms may differ by the concentration of drug in a dose of the dosage formulation. Further, any two of the two or more dosage forms may differ both by the concentration of drug in a dose of the dosage formulation and by the total amount of drug in a dose of the dosage formulation.

EXAMPLES

An exemplary method of determining an administration regimen of a drug to a subject will now be described. The example now described relates to the administration of the drug emicizumab, commercially available as HEMLIBRA® (Roche Products Limited). Emicizumab is a humanised monoclonal modified immunoglobulin G4 (IgG4) antibody produced using recombinant DNA technology in mammalian Chinese Hamster Ovary (CHO) cells. Emicizumab is described in EP2644698B1, which is incorporated herein by reference. Emicizumab is a bispecific antibody that specifically binds to blood coagulation factor F.IX/F.IXa and to blood coagulation factor F.X, and substitutes for the cofactor function of blood coagulation factor F.VIII by promoting activation of F.X by F.IXa. This function is deficient in patients with Hemophilia A, resulting in a bleeding abnormality. Emicizumab is commercially available in four different dosage forms, all of which are solutions for subcutaneous injection:

Hemlibra 30 mg: vials of 1 ml of solution containing 30 mg of emicizumab, at a concentration of 30 mg/ml; this is also referred to as 'sky-blue vial' herein, due to the colour of the packaging of this dosage form;

Hemlibra 60 mg: vials of 0.4 ml of solution containing 60 mg of emicizumab, at a concentration of 150 mg/ml; this is also referred to as 'purple vial' herein;

Hemlibra 105 mg: vials of 0.7 ml of solution containing 105 mg of emicizumab, at a concentration of 150 mg/ml; this is also referred to as 'turquoise vial' herein; and Hemlibra 150 mg: vials of 1 ml of solution containing 150 mg of emicizumab, at a concentration of 150 mg/ml; this is also referred to as 'brown vial' herein.

Hemlibra is indicated for routine prophylaxis of bleeding episodes in patients with haemophilia A (congenital factor VIII deficiency) with factor VIII inhibitors, and severe haemophilia A (congenital factor VIII deficiency, FVIII <1%) without factor VIII inhibitors.

Through clinical trials, it was determined that Hemlibra can be used in all age groups, and that a two phase administration regimen should be followed comprising:

a loading phase: a recommended dose of 3 mg/kg is to be administered once weekly for 4 weeks;

a maintenance phase: a recommended dose of 1.5 mg/kg/week is to be administered with a minimum frequency of once every 4 weeks (maximum interval of 4 weeks between administrations), i.e. 1.5 mg/kg to be administered once weekly, 3 mg/kg to be administered once every two weeks, or 6 mg/kg to be administered once every four weeks.

In this example, further rules for administration were provided, including that two different concentrations of Hemlibra to be combined in the same syringe, that each injection should not exceed 2 ml to be administered in 1 ml or 2-3 ml syringes, and that a 1 ml syringe was to be used to administer amounts specified with two decimals precision (in ml). The data from clinical trials provide that a maintenance regimen (weekly, every 2 weeks or every four weeks) should be chosen with the aim of supporting adherence, an amount of emicizumab should be calculated accordingly as "Patient bodyweight (kg)×dose (1.5; 3 or 6 mg/kg)=total amount (mg) of emicizumab to be administered" and an appropriate dosage and volume from vial strength available should be chosen, where once a vial has been chosen, the total volume of Hemlibra can be calculated as "Total amount (mg) of emicizumab to be administered÷vial concentration (mg/mL)=total volume of Hemlibra (mL) to be injected".

This leaves many options open, and creates potential for errors as a regimen that supports adherence may not be chosen completely independently from the choice of vial combinations that will be used. Indeed, adherence may depend on factors such as the number of injections required, the wastage associated with a regimen, etc. As such, the inventors have identified that the choice of an administration regimen should take into account multiple variables including in this example the frequency of administration in the maintenance regimen, the weight of the patient, the different dosage forms available, the restrictions on administration (volumes and combinations of dosage forms), and the criteria that may be of relevance to a patient including the amount of product that is wasted (per administration and over a four weeks period), the number of injections required (per administration), and the number of physical steps required to prepare an administration (which is proportional to the number of vial draws required). The inventors have therefore designed a tool that takes all of these variables into account to determine an administration regimen for a patient.

In the particular implementation described here, the method takes as input:

preset dose multipliers (x mg/kg) for the loading phase (QL=3 mg/kg), the weekly (Q1W=1.5 mg/kg), biweekly (Q2W=3 mg/kg), and four-weekly (Q4W=6 mg/kg) maintenance phase regimen;

concentrations ($C_{SB}$, $C_P$, $C_T$, $C_B$) and volumes ($V_{SB}$, $V_P$, $V_T$, $V_B$) for each of the four types of dosage forms (D1=sky blue vial (SB), D2=purple vial (P), D3=turquoise vial (T), D4=brown vial (B));

a range of weights for which administration regimen should be determined, for example w=3 to 150 kg, by integer increments;

rules on administration procedures such as e.g. two possible volumes of syringes $V_1$, $V_2$, conditions as to when a particular syringe volume cannot be used, and whether different vials/vials with different concentrations can be combined in the same syringe.

The method then performs three successive steps:

1. calculate doses: the total dose (mg) for each weight for each regimen (loading, maintenance-weekly, maintenance-biweekly, maintenance-four-weekly)—where the loading dose is the same as the maintenance-biweekly dose (although the administration interval is different);
2. calculate combinations: for each total dose, generate all minimal combinations of dosage forms that can be used to achieve the total dose, calculate the parameters of each minimal combination;
3. generate recommendations: for each weight, identify the combinations that minimise one or more criteria and generate instructions for these.

These steps will be discussed in more detail below. In the example discussed below, steps 1 to 3 are performed for a range of weights, and all of the combinations and recommendations for each of these weights are pre-computed. As such, recommendations can simply be extracted from the appropriate recommendations set when a specific weight is entered through a user interface. In other implementations not discussed in detail below, each of steps 1 to 3 are performed for a single, specific weight. For example, steps 1 to 3 can be performed on-the-fly upon receipt of a weight entered through a user interface. Similar computations as those discussed below apply in such cases, albeit for a single weight rather than a list of weights.

In step 1, each of four total doses $A_L^w{}_t$, $A^w{}_t$, $A^w{}_{n1t}$, $A^w{}_{n2t}$ (where t=1 week, n1=2, n2=4 and L refers to the loading phase dose) is calculated for each weight w=3 . . . 150 as:

$$A_L^w{}_t = QL * w \quad \text{(Equation 1)}$$

$$A^w{}_t = Q1W * w \quad \text{(Equation 2)}$$

$$A^w{}_{n1t} = Q2W * w = Q1W * n1 * w \quad \text{(Equation 3)}$$

$$A^w{}_{n2t} = Q4W * w = Q1W * n2 * w \quad \text{(Equation 4)}$$

Step 1 results in a list of 441 total doses (3 different total doses for each of 147 different weights)—since QL=Q2W in this example. This list is taken as an input to step 2. In step 2, all possible minimal combinations of the four dosage forms that can be used to achieve each of the amounts of drug represented in these 441 total doses are computed. In particular, for each of the total doses ($A_L^w{}_t$, $A^w{}_t$, $A^w{}_{nt1}$, $A^w{}_{n2t}$—or for improved efficiency, for each of the 5 different total doses represented in this list), in order to calculate the numbers of SB, P, T and B vials ($n_{SB}$, $n_P$, $n_T$, $n_B$) that make up a combination, the following steps are performed:

a. sky blue led combinations
   i. sky blue alone ($A^w$[SB]): calculate the minimum number of sky blue vials that achieve the dose ($A^w$) as $$n_{SB} = \text{round.up}(A^w/(C_{SB} * V_{SB}))\qquad\text{(Equation 5])}$$

where roundup( ) rounds up the number between brackets to the nearest integer ii. sky blue in combination with purple ($A^w$[SBP]): loop through: 1 SB vial+minimum number of P vials that achieve the dose ($A^w$); 2 SB vials+minimum number of P vials that achieve the dose; etc. until the number of SB vials is such that no additional vial is needed to make up the total amount (at which point the number of SB vials is just below $n_{SB}$ calculated in step i) where for each number of SB vials $n_{SB}$, the minimum number of P vials is calculated as:

$$n_P = \text{round.up}((A^w - 1*(C_{SB}*V_{SB}))/(C_P*V_P))\qquad\text{(Equation 6)}$$

iii. sky blue in combination with turquoise ($A^w$[SBT]): loop through: 1 SB vial+minimum number of T vials that achieve the dose ($A^w$); 2 SB vials+minimum number of T vials that achieve the dose; etc. until the number of SB vials is such that no additional vial is needed to make up the total amount, where for each number of SB vials $n_{SB}$, the minimum number of T vials is calculated as:

$$n_T = \text{round.up}((A^w - 1*(C_{SB}*V_{SB}))/(C_T*V_T))\qquad\text{(Equation 7)}$$

iv. sky blue in combination with brown ($A^w$[SBB]): loop through: 1 SB vial+minimum number of B vials that achieve the dose ($A^w$); 2 SB vials+minimum number of B vials that achieve the dose; etc. until the number of SB vials is such that no additional vial is needed to make up the total amount (i.e. the $n_{SB}$ calculated in step i) where for each number of SB vials $n_{SB}$, the minimum number of B vials is calculated as:

$$n_B = \text{round.up}((A^w - 1*(C_{SB}*V_{SB}))/(C_B*V_B))\qquad\text{(Equation 8)}$$

b. repeat the process in a. for purple led combinations
c. repeat the process in a. for turquoise led combinations
d. repeat the process in a. for brown led combinations
e. calculate the 3 colours combinations:
   i. sky blue led, +purple and turquoise ($A^w$[SBPT]): loop through x=number of SB vials and y=number of P vials:
      x=1: 1 SB vial+1 P vial+minimum number of T vials that achieve the dose; 1 SB vial+2 P vial+minimum number of T vials that achieve the dose; etc. until the total amount in 1 SB vial+y P vial exceeds the total amount $A^w$;
      x=2: 2 SB vials+1 P vial+minimum number of T vials that achieve the dose; 2 SB vial+2 P vial+minimum number of T vials that achieve the dose; etc. until the total amount in 2 SB vial+y P vial exceeds the total amount $A^w$;
      etc. until the total amount in x×SB+1 P exceeds the total amount $A^w$.
   ii. repeat step i for sky blue led, +purple and brown ($A^w$[SBPB])
   iii. repeat step i for sky blue led, +turquoise and purple ($A^w$[SBTP])
   iv. repeat step i for sky blue led, +turquoise and brown ($A^w$[SBTB])
   v. repeat step i for sky blue led, +brown and purple ($A^w$[SBBP])
   vi. repeat step i for sky blue led, +brown and turquoise ($A^w$[SBBT])
   vii. repeat step i for purple led, +turquoise and sky blue ($A^w$[PTSB])
   viii. repeat step i for purple led, +turquoise and brown ($A^w$[PTB])
   ix. repeat step i for purple led, +brown and sky blue ($A^w$[PBSB])
   x. repeat step i for purple led, +brown and turquoise ($A^w$[PBT])
   xi. repeat step i for turquoise led, +purple and sky blue ($A^w$[TPSB])
   xii. repeat step i for turquoise led, +purple and brown ($A^w$[TPB])
   xiii. repeat step i for turquoise led, +brown and sky blue ($A^w$[TBSB])
   xiv. repeat step i for turquoise led, +brown and purple ($A^w$[TBP])
   xv. repeat step i for brown led, +purple and sky blue ($A^w$[BPSB])
   xvi. repeat step i for brown led, +purple and turquoise ($A^w$[BPT])
   xvii. repeat step i for brown led, +turquoise and sky blue ($A^w$[BTSB])
   xviii. repeat step i for brown led, +turquoise and purple ($A^w$[BTP])

Step 2 also comprises, for each of the combinations, the calculation of multiple parameters of each minimal combination including at least: the total number of vial draws (total number of vials needed), the amount of product drawn from each vial (in mg and in ml), the wastage in mg of product unused per administration, and the number of injections required to administer the combination. The wastage in mg of product unused can be calculated in multiple ways. For example, the total amount of drug in the combination can be calculated as $$\text{Total}(n_{SB}, n_P, n_T, n_B) = (n_{SB}*C_{SB}*V_{SB}) + (n_P*C_P*V_P) + (n_T*C_T*V_T) + (n_B*C_B*V_B)\qquad\text{(Equation 9)}$$

And the wastage W for a combination for a particular amount $A^w$ can be calculated as $$W = \text{Total}(n_{SB}, n_P, n_T, n_B) - A^w\qquad\text{(Equation 10)}$$

Alternatively, the total amount (ml or mg) that is drawn from each vial may be calculated and compared to the total amount (ml or mg) that is available from each vial.

The total amount drawn from each vial can be calculated as the total amount present in each vial for all but the last added vial, for which the amount drawn can be calculated as the volume needed to reach the amount needed $A^w$ minus the amount already provided by the other vials. As the skilled person would understand, the particular order of the steps used to generate the combinations is arbitrary and any order can be used provided that all possible combinations are generated. Further, the parameters for each combination may be calculated as each combination is generated, or a list of combinations may be generated and looped through to calculate each of the parameters. The number of injections to be used to administer a combination is calculated based on the rules mentioned above about the volumes of syringes $V_1$, $V_2$ and the rules on combinations of vials/concentrations. In the present examples, syringes of 1 ml or 2 ml can be used, and the sky blue vial cannot be combined with any of the purple, turquoise and brown vials. The number of injections can be calculated in this case by:

if at least one sky blue vial is used ($n_{SB} \geq 1$)
calculating the number of injections of $V_1=1$ ml or $V_2=2$ ml that are necessary to administer the total amount of product that is contributed by sky blue vials in the combination;
calculating the number of injections of $V_1=1$ ml or $V_2=2$ ml that are necessary to administer the total amount of product that is contributed by all of the other vials together in the combination, with the added restriction that any amount specified with 2 decimal precision (in ml) can only be administered with a 1 ml syringe—for example, by calculating the number of injections necessary to administer all of the full vials, and determining whether the remaining volume to be administered requires the use of a 1 ml syringe;
adding up the above four numbers to generate three sub-combinations: a sub-combination that only uses $V_1=1$ ml, a combination that uses only $V_2=2$ ml, and two combinations that use both volumes.
If no sky blue vial is used ($n_{SB}=0$): calculating the number of injections of $V_1=1$ ml or $V_2=2$ ml that are necessary to administer the total amount of product that is contributed by all of the other vials together in the combination, with the added restriction that any amount specified with 2 decimal precision (in ml) can only be administered with a 1 ml syringe.
Filter the combinations, if required, to keep only: combinations that have a minimum amount of injections, combinations that use the smallest possible syringe and/or combinations that only use one type of syringe (i.e. one volume).

As a result of step 2, a data table is produced that contains information and parameters for each of 85,008 combinations. A subset of this table including multiple exemplary parameters for selection of possible combinations that achieve one of four different exemplary total doses are shown in the Table 1 below. In the example shown, a table is obtained that lists all combinations and their parameters, for each of the different amounts $A^w$ that have been generated in step 1. This table can be expanded to list all combinations and their parameters for each of the weights in w=3 . . . 150 kg and for each of the four types of administration regimen $A_L{}^w{}_t$, $A^w{}_t$, $A^w{}_{n1t}$, $A^w{}_{n2t}$. Alternatively, as explained above, the table generated in step 2 may also list all combinations for all four types of administration regimen for each weight.

When generating such an extended table (or when originally generating the table in Step 2 in an extended form), the wastage per comparable period of time (e.g. 4 weeks) can also be calculated. The total amount of wastage per comparable period of time is calculated in this example by scaling the wastages per administration appropriately, i.e. either dividing the wastages for the n1=2 and n2=4 total doses ($A^w{}_{n1t}$, $A^w{}_{n2t}$) by 2 and 4, respectively, or multiplying the wastages for the n=1 (i.e. $A^w{}_t$) and n1=2 ($A^w{}_{n1t}$) total doses by 4 and 2, respectively. The latter may be preferable as it may result in a more intuitive measure of wastage.

The method then proceeds to step 3, where recommendations are generated. In this example, recommendations are generated using three different criteria: the amount of wastage over 4 weeks, the number of injections per administration, and the number of vial draws. In particular, for each patient weight in w=3 . . . 150 kg, the method generates a list of all administration regimen that have been evaluated. The method then ranks each list according to the above-mentioned three criteria in a nested/hierarchical manner (by ranking the combinations according to a first criterion, then within each rank, ranking the combinations according to a second criterion, and within each of these ranks, ranking the combinations according to a third criterion and/or flagging the best ranked combination within each rank). Further, this is done in this example according to two different hierarchies.

A first hierarchy prioritises the minimisation of wastage per comparable period of time (e.g. the total wastage over 4 weeks), and the combinations in the table are therefore ranked according to total wastage. The best ranked (i.e. lowest wastage) combinations are then ranked again according to the number of injections per administration. The best ranked (i.e. lowest number of injections) combinations are then ranked according to the number of vial draws. The final best ranked combinations (i.e. top ranked combinations (based on vial draws) amongst the top ranked combinations (based on number of injections) amongst the top ranked combinations (based on total wastage)) are then stored in a "least wastage recommendations" list. In the present example, each ranking is performed separately for each of the four categories of administration regimen (loading, maintenance-weekly, maintenance-biweekly, and maintenance-four weekly), and a best ranked combination is output to the "least wastage recommendations" list for each of these. Where two or more combinations have the same rank across all three criteria, all of these combinations can be output to the "least wastage recommendations" list, or one may be arbitrarily selected. Further, the combinations in the "least wastage recommendations" list are flagged if they have either or both of (i) the same total wastage as the overall lowest total wastage combination (across all categories of administration regimen) and (ii) the same number of injections as the overall lowest number of injections combination (across all categories of administration regimen). Alternatively, it is possible for the nested rankings to be performed jointly for all maintenance regimen. In such cases, only the options that have the optimal values are output, which may not include a solution for each of the different categories of maintenance regimen.

A second hierarchy prioritises the minimisation of the number of injections, and the combinations in the table are therefore ranked according to the number of injections per administration. The best ranked (i.e. lowest number of injections) combinations are then ranked again according to the number of vial draws per administration. The best ranked (i.e. lowest number of vial draws) combinations are then ranked according to the lowest total wastage. The final best ranked combinations are then stored in a "least injections recommendations" list. In the present example, each ranking is performed separately for each of the four categories of administration regimen (loading, maintenance-weekly, maintenance-biweekly, and maintenance-four weekly), and a best ranked combination is output to the "least injections recommendations" list for each of these. Where two or more combinations have the same rank across all three criteria, all of these combinations can be output to the "least injections recommendations" list, or one can be selected arbitrarily. However, the combinations in the "least injections recommendations" list are flagged if they have either or both of (i) the same total wastage as the overall lowest total wastage combination (across all categories of administration regimen) and (ii) the same number of injections as the overall lowest number of injections combination (across all categories of administration regimen).

In the present example, the method generates separate recommendations tables for the loading and maintenance regimen, by repeating the above process for the loading dose combinations and for the maintenance dose combinations. As a result of step 3, four data tables are produced that contain information and parameters for each of the combinations that minimise the above-mentioned hierarchical criteria. Subsets of these tables are shown in Tables 2 to 5 below. Some of the values in those tables can be derived from the values in other columns in multiple manners. For example, the total amounts of volumes of each dosage form can be calculated by multiplying the number of vials and volumes (Full vials[#V * Vol.]; Part vial[#V * Vol.]), and summing these up, for each dosage form. Alternatively, these can be derived from the total weight of product contributed by each dosage form. In embodiments, each value that can be calculated in more than one ways is calculated in at least two of these ways, in order to check the internal consistency of the data produced. Similarly, the data in relation to the total volume of product and the total amount of product should be convertible into each other, based on data from other columns. In embodiments, each volume/mg value is compared to its corresponding mg/volume value, and/or to its constituent volumes and/or mg values, in order to check that the data is consistent.

Table 1 provides a subset of data (23 out of 85,008 rows) computed in relation to combinations of dosage forms that are generated in the present exemplary embodiment. In the table below, CN=combination number, SB=sky blue, P=purple, T=turquoise, B=brown, W=wastage.

| | Component Volumes (mL) | | | | | Product (mg) | | | | | Wastage (mg) | | | | |
|---|---|---|---|---|---|---|---|---|---|---|---|---|---|---|---|
| CN | SB mL | P mL | T. mL | B mL | Total mL | SB (mg) | P (mg) | T. (mg) | B (mg) | Total Product (mg) | SB W (mg) | P W (mg) | T W (mg) | B W (mg) | Total wastage (mg) |
| 1 | 0.15 | 0 | 0 | 0 | 0.15 | 4.5 | 0 | 0 | 0 | 4.5 | 25.5 | 0 | 0 | 0 | 25.5 |
| 1773 | 0 | 0.03 | 0 | 0 | 0.03 | 0 | 4.5 | 0 | 0 | 4.5 | 0 | 55.5 | 0 | 0 | 55.5 |
| 12272 | 0 | 0 | 0.03 | 0 | 0.03 | 0 | 0 | 4.5 | 0 | 4.5 | 0 | 0 | 100.5 | 0 | 100.5 |
| 18230 | 0 | 0 | 0 | 0.03 | 0.03 | 0 | 0 | 0 | 4.5 | 4.5 | 0 | 0 | 0 | 145.5 | 145.5 |
| 129 | 1 | 0.43 | 0 | 0 | 1.43 | 30 | 64.5 | 0 | 0 | 94.5 | 0 | 55.5 | 0 | 0 | 55.5 |
| 709 | 1 | 0 | 0.43 | 0 | 1.43 | 30 | 0 | 64.5 | 0 | 94.5 | 0 | 0 | 40.5 | 0 | 40.5 |
| 1235 | 1 | 0 | 0 | 0.43 | 1.43 | 30 | 0 | 0 | 64.5 | 94.5 | 0 | 0 | 0 | 85.5 | 85.5 |
| 1833 | 0 | 0.63 | 0 | 0 | 0.63 | 0 | 94.5 | 0 | 0 | 94.5 | 0 | 25.5 | 0 | 0 | 25.5 |
| 3893 | 0 | 0.4 | 0.23 | 0 | 0.63 | 0 | 60 | 34.5 | 0 | 94.5 | 0 | 0 | 70.5 | 0 | 70.5 |
| 8094 | 0 | 0.4 | 0 | 0.23 | 0.63 | 0 | 60 | 0 | 34.5 | 94.5 | 0 | 0 | 0 | 115.5 | 115.5 |
| 12332 | 0 | 0 | 0.63 | 0 | 0.63 | 0 | 0 | 94.5 | 0 | 94.5 | 0 | 0 | 10.5 | 0 | 10.5 |
| 18290 | 0 | 0 | 0 | 0.63 | 0.63 | 0 | 0 | 0 | 94.5 | 94.5 | 0 | 0 | 0 | 55.5 | 55.5 |
| 22532 | 1 | 0.4 | 0.03 | 0 | 1.43 | 30 | 60 | 4.5 | 0 | 94.5 | 0 | 0 | 100.5 | 0 | 100.5 |
| 26434 | 1 | 0.4 | 0 | 0.03 | 1.43 | 30 | 60 | 0 | 4.5 | 94.5 | 0 | 0 | 0 | 145.5 | 145.5 |
| 181 | 1 | 0.95 | 0 | 0 | 1.95 | 30 | 142.5 | 0 | 0 | 172.5 | 0 | 37.5 | 0 | 0 | 37.5 |
| 761 | 1 | 0 | 0.95 | 0 | 1.95 | 30 | 0 | 142.5 | 0 | 172.5 | 0 | 0 | 67.5 | 0 | 67.5 |
| 1287 | 1 | 0 | 0 | 0.95 | 1.95 | 30 | 0 | 0 | 142.5 | 172.5 | 0 | 0 | 0 | 7.5 | 7.5 |
| 1885 | 0 | 1.15 | 0 | 0 | 1.15 | 0 | 172.5 | 0 | 0 | 172.5 | 0 | 7.5 | 0 | 0 | 7.5 |
| 3945 | 0 | 0.4 | 0.75 | 0 | 1.15 | 0 | 60 | 112.5 | 0 | 172.5 | 0 | 0 | 97.5 | 0 | 97.5 |
| 4465 | 0 | 0.8 | 0.35 | 0 | 1.15 | 0 | 120 | 52.5 | 0 | 172.5 | 0 | 0 | 52.5 | 0 | 52.5 |
| 8146 | 0 | 0.4 | 0 | 0.75 | 1.15 | 0 | 60 | 0 | 112.5 | 172.5 | 0 | 0 | 0 | 37.5 | 37.5 |
| 8666 | 0 | 0.8 | 0 | 0.35 | 1.15 | 0 | 120 | 0 | 52.5 | 172.5 | 0 | 0 | 0 | 97.5 | 97.5 |
| 12384 | 0 | 0 | 1.15 | 0 | 1.15 | 0 | 0 | 172.5 | 0 | 172.5 | 0 | 0 | 37.5 | 0 | 37.5 |
| 13714 | 0 | 0.45 | 0.7 | 0 | 1.15 | 0 | 67.5 | 105 | 0 | 172.5 | 0 | 52.5 | 0 | 0 | 52.5 |
| 15994 | 0 | 0 | 0.7 | 0.45 | 1.15 | 0 | 0 | 105 | 67.5 | 172.5 | 0 | 0 | 0 | 82.5 | 82.5 |
| 18342 | 0 | 0 | 0 | 1.15 | 1.15 | 0 | 0 | 0 | 172.5 | 172.5 | 0 | 0 | 0 | 127.5 | 127.5 |
| 18902 | 0.75 | 0 | 0 | 1 | 1.75 | 22.5 | 0 | 0 | 150 | 172.5 | 7.5 | 0 | 0 | 0 | 7.5 |
| 19542 | 0 | 0.15 | 0 | 1 | 1.15 | 0 | 22.5 | 0 | 150 | 172.5 | 0 | 37.5 | 0 | 0 | 37.5 |
| 21043 | 0 | 0 | 0.15 | 1 | 1.15 | 0 | 0 | 22.5 | 150 | 172.5 | 0 | 0 | 82.5 | 0 | 82.5 |
| 22584 | 1 | 0.4 | 0.55 | 0 | 1.95 | 30 | 60 | 82.5 | 0 | 172.5 | 0 | 0 | 22.5 | 0 | 22.5 |
| 23066 | 1 | 0.8 | 0.15 | 0 | 1.95 | 30 | 120 | 22.5 | 0 | 172.5 | 0 | 0 | 82.5 | 0 | 82.5 |
| 26486 | 1 | 0.4 | 0 | 0.55 | 1.95 | 30 | 60 | 0 | 82.5 | 172.5 | 0 | 0 | 0 | 67.5 | 67.5 |
| 26986 | 1 | 0.8 | 0 | 0.15 | 1.95 | 30 | 120 | 0 | 22.5 | 172.5 | 0 | 0 | 0 | 127.5 | 127.5 |
| 30376 | 1 | 0.25 | 0.7 | 0 | 1.95 | 30 | 37.5 | 105 | 0 | 172.5 | 0 | 22.5 | 0 | 0 | 22.5 |
| 32460 | 1 | 0 | 0.7 | 0.25 | 1.95 | 30 | 0 | 105 | 37.5 | 172.5 | 0 | 0 | 0 | 112.5 | 112.5 |
| 37254 | 0.25 | 0.4 | 0.7 | 0 | 1.35 | 7.5 | 60 | 105 | 0 | 172.5 | 22.5 | 0 | 0 | 0 | 22.5 |
| 42534 | 0 | 0.4 | 0.7 | 0.05 | 1.15 | 0 | 60 | 105 | 7.5 | 172.5 | 0 | 0 | 0 | 142.5 | 142.5 |
| 53454 | 0.25 | 0.4 | 0.7 | 0 | 1.35 | 7.5 | 60 | 105 | 0 | 172.5 | 22.5 | 0 | 0 | 0 | 22.5 |
| 58734 | 0 | 0.4 | 0.7 | 0.05 | 1.15 | 0 | 60 | 105 | 7.5 | 172.5 | 0 | 0 | 0 | 142.5 | 142.5 |
| 462 | 1 | 3.76 | 0 | 0 | 4.76 | 30 | 564 | 0 | 0 | 594 | 0 | 36 | 0 | 0 | 36 |
| 1042 | 1 | 0 | 3.76 | 0 | 4.76 | 30 | 0 | 564 | 0 | 594 | 0 | 0 | 66 | 0 | 66 |
| 1568 | 1 | 0 | 0 | 3.76 | 4.76 | 30 | 0 | 0 | 564 | 594 | 0 | 0 | 0 | 36 | 36 |
| 2166 | 0 | 3.96 | 0 | 0 | 3.96 | 0 | 594 | 0 | 0 | 594 | 0 | 6 | 0 | 0 | 6 |
| 4226 | 0 | 0.4 | 3.56 | 0 | 3.96 | 0 | 60 | 534 | 0 | 594 | 0 | 0 | 96 | 0 | 96 |
| 4746 | 0 | 0.8 | 3.16 | 0 | 3.96 | 0 | 120 | 474 | 0 | 594 | 0 | 0 | 51 | 0 | 51 |
| 5226 | 0 | 1.2 | 2.76 | 0 | 3.96 | 0 | 180 | 414 | 0 | 594 | 0 | 0 | 6 | 0 | 6 |
| 5666 | 0 | 1.6 | 2.36 | 0 | 3.96 | 0 | 240 | 354 | 0 | 594 | 0 | 0 | 66 | 0 | 66 |
| 6066 | 0 | 2 | 1.96 | 0 | 3.96 | 0 | 300 | 294 | 0 | 594 | 0 | 0 | 21 | 0 | 21 |
| 6426 | 0 | 2.4 | 1.56 | 0 | 3.96 | 0 | 360 | 234 | 0 | 594 | 0 | 0 | 81 | 0 | 81 |
| 6746 | 0 | 2.8 | 1.16 | 0 | 3.96 | 0 | 420 | 174 | 0 | 594 | 0 | 0 | 36 | 0 | 36 |
| 7026 | 0 | 3.2 | 0.76 | 0 | 3.96 | 0 | 480 | 114 | 0 | 594 | 0 | 0 | 96 | 0 | 96 |
| 7266 | 0 | 3.6 | 0.36 | 0 | 3.96 | 0 | 540 | 54 | 0 | 594 | 0 | 0 | 51 | 0 | 51 |

-continued

| | | | | | | | | | | | | | | | |
|---|---|---|---|---|---|---|---|---|---|---|---|---|---|---|---|
| 8427 | 0 | 0.4 | 0 | 3.56 | 3.96 | 0 | 60 | 0 | 534 | 594 | 0 | 0 | 0 | 66 | 66 |
| 8947 | 0 | 0.8 | 0 | 3.16 | 3.96 | 0 | 120 | 0 | 474 | 594 | 0 | 0 | 0 | 126 | 126 |
| 9427 | 0 | 1.2 | 0 | 2.76 | 3.96 | 0 | 180 | 0 | 414 | 594 | 0 | 0 | 0 | 36 | 36 |
| 9867 | 0 | 1.6 | 0 | 2.36 | 3.96 | 0 | 240 | 0 | 354 | 594 | 0 | 0 | 0 | 96 | 96 |
| 10267 | 0 | 2 | 0 | 1.96 | 3.96 | 0 | 300 | 0 | 294 | 594 | 0 | 0 | 0 | 6 | 6 |
| 10627 | 0 | 2.4 | 0 | 1.56 | 3.96 | 0 | 360 | 0 | 234 | 594 | 0 | 0 | 0 | 66 | 66 |
| 10947 | 0 | 2.8 | 0 | 1.16 | 3.96 | 0 | 420 | 0 | 174 | 594 | 0 | 0 | 0 | 126 | 126 |
| 11227 | 0 | 3.2 | 0 | 0.76 | 3.96 | 0 | 480 | 0 | 114 | 594 | 0 | 0 | 0 | 36 | 36 |
| 11467 | 0 | 3.6 | 0 | 0.36 | 3.96 | 0 | 540 | 0 | 54 | 594 | 0 | 0 | 0 | 96 | 96 |
| 12665 | 0 | 0 | 3.96 | 0 | 3.96 | 0 | 0 | 594 | 0 | 594 | 0 | 0 | 36 | 0 | 36 |
| 13995 | 0 | 3.26 | 0.7 | 0 | 3.96 | 0 | 489 | 105 | 0 | 594 | 0 | 51 | 0 | 0 | 51 |
| 14455 | 0 | 2.56 | 1.4 | 0 | 3.96 | 0 | 384 | 210 | 0 | 594 | 0 | 36 | 0 | 0 | 36 |
| 14845 | 0 | 1.86 | 2.1 | 0 | 3.96 | 0 | 279 | 315 | 0 | 594 | 0 | 21 | 0 | 0 | 21 |
| 15165 | 0 | 1.16 | 2.8 | 0 | 3.96 | 0 | 174 | 420 | 0 | 594 | 0 | 6 | 0 | 0 | 6 |
| 15415 | 0 | 0.46 | 3.5 | 0 | 3.96 | 0 | 69 | 525 | 0 | 594 | 0 | 51 | 0 | 0 | 51 |
| 16275 | 0 | 0 | 0.7 | 3.26 | 3.96 | 0 | 0 | 105 | 489 | 594 | 0 | 0 | 0 | 111 | 111 |
| 16735 | 0 | 0 | 1.4 | 2.56 | 3.96 | 0 | 0 | 210 | 384 | 594 | 0 | 0 | 0 | 66 | 66 |
| 17125 | 0 | 0 | 2.1 | 1.86 | 3.96 | 0 | 0 | 315 | 279 | 594 | 0 | 0 | 0 | 21 | 21 |
| 17445 | 0 | 0 | 2.8 | 1.16 | 3.96 | 0 | 0 | 420 | 174 | 594 | 0 | 0 | 0 | 126 | 126 |
| 17695 | 0 | 0 | 3.5 | 0.46 | 3.96 | 0 | 0 | 525 | 69 | 594 | 0 | 0 | 0 | 81 | 81 |
| 18623 | 0 | 0 | 0 | 3.96 | 3.96 | 0 | 0 | 0 | 594 | 594 | 0 | 0 | 0 | 6 | 6 |
| 19823 | 0 | 2.96 | 0 | 1 | 3.96 | 0 | 444 | 0 | 150 | 594 | 0 | 36 | 0 | 0 | 36 |
| 20223 | 0 | 1.96 | 0 | 2 | 3.96 | 0 | 294 | 0 | 300 | 594 | 0 | 6 | 0 | 0 | 6 |
| 20523 | 0 | 0.96 | 0 | 3 | 3.96 | 0 | 144 | 0 | 450 | 594 | 0 | 36 | 0 | 0 | 36 |
| 21324 | 0 | 0 | 2.96 | 1 | 3.96 | 0 | 0 | 444 | 150 | 594 | 0 | 0 | 81 | 0 | 81 |
| 21724 | 0 | 0 | 1.96 | 2 | 3.96 | 0 | 0 | 294 | 300 | 594 | 0 | 0 | 21 | 0 | 21 |
| 22024 | 0 | 0 | 0.96 | 3 | 3.96 | 0 | 0 | 144 | 450 | 594 | 0 | 0 | 66 | 0 | 66 |
| 22865 | 1 | 0.4 | 3.36 | 0 | 4.76 | 30 | 60 | 504 | 0 | 594 | 0 | 0 | 21 | 0 | 21 |
| 23347 | 1 | 0.8 | 2.96 | 0 | 4.76 | 30 | 120 | 444 | 0 | 594 | 0 | 0 | 81 | 0 | 81 |
| 23807 | 1 | 1.2 | 2.56 | 0 | 4.76 | 30 | 180 | 384 | 0 | 594 | 0 | 0 | 36 | 0 | 36 |
| 24227 | 1 | 1.6 | 2.16 | 0 | 4.76 | 30 | 240 | 324 | 0 | 594 | 0 | 0 | 96 | 0 | 96 |
| 24607 | 1 | 2 | 1.76 | 0 | 4.76 | 30 | 300 | 264 | 0 | 594 | 0 | 0 | 51 | 0 | 51 |
| 24947 | 1 | 2.4 | 1.36 | 0 | 4.76 | 30 | 360 | 204 | 0 | 594 | 0 | 0 | 6 | 0 | 6 |
| 25247 | 1 | 2.8 | 0.96 | 0 | 4.76 | 30 | 420 | 144 | 0 | 594 | 0 | 0 | 66 | 0 | 66 |
| 25507 | 1 | 3.2 | 0.56 | 0 | 4.76 | 30 | 480 | 84 | 0 | 594 | 0 | 0 | 21 | 0 | 21 |
| 25727 | 1 | 3.6 | 0.16 | 0 | 4.76 | 30 | 540 | 24 | 0 | 594 | 0 | 0 | 81 | 0 | 81 |
| 26767 | 1 | 0.4 | 0 | 3.36 | 4.76 | 30 | 60 | 0 | 504 | 594 | 0 | 0 | 0 | 96 | 96 |
| 27267 | 1 | 0.8 | 0 | 2.96 | 4.76 | 30 | 120 | 0 | 444 | 594 | 0 | 0 | 0 | 6 | 6 |
| 27727 | 1 | 1.2 | 0 | 2.56 | 4.76 | 30 | 180 | 0 | 384 | 594 | 0 | 0 | 0 | 66 | 66 |
| 28147 | 1 | 1.6 | 0 | 2.16 | 4.76 | 30 | 240 | 0 | 324 | 594 | 0 | 0 | 0 | 126 | 126 |
| 28527 | 1 | 2 | 0 | 1.76 | 4.76 | 30 | 300 | 0 | 264 | 594 | 0 | 0 | 0 | 36 | 36 |
| 28867 | 1 | 2.4 | 0 | 1.36 | 4.76 | 30 | 360 | 0 | 204 | 594 | 0 | 0 | 0 | 96 | 96 |
| 29167 | 1 | 2.8 | 0 | 0.96 | 4.76 | 30 | 420 | 0 | 144 | 594 | 0 | 0 | 0 | 6 | 6 |
| 29427 | 1 | 3.2 | 0 | 0.56 | 4.76 | 30 | 480 | 0 | 84 | 594 | 0 | 0 | 0 | 66 | 66 |
| 29647 | 1 | 3.6 | 0 | 0.16 | 4.76 | 30 | 540 | 0 | 24 | 594 | 0 | 0 | 0 | 126 | 126 |
| 30657 | 1 | 3.06 | 0.7 | 0 | 4.76 | 30 | 459 | 105 | 0 | 594 | 0 | 21 | 0 | 0 | 21 |
| 31097 | 1 | 2.36 | 1.4 | 0 | 4.76 | 30 | 354 | 210 | 0 | 594 | 0 | 6 | 0 | 0 | 6 |
| 31467 | 1 | 1.66 | 2.1 | 0 | 4.76 | 30 | 249 | 315 | 0 | 594 | 0 | 51 | 0 | 0 | 51 |
| 31767 | 1 | 0.96 | 2.8 | 0 | 4.76 | 30 | 144 | 420 | 0 | 594 | 0 | 36 | 0 | 0 | 36 |
| 31997 | 1 | 0.26 | 3.5 | 0 | 4.76 | 30 | 39 | 525 | 0 | 594 | 0 | 21 | 0 | 0 | 21 |
| 32741 | 1 | 0 | 0.7 | 3.06 | 4.76 | 30 | 0 | 105 | 459 | 594 | 0 | 0 | 0 | 141 | 141 |
| 33181 | 1 | 0 | 1.4 | 2.36 | 4.76 | 30 | 0 | 210 | 354 | 594 | 0 | 0 | 0 | 96 | 96 |
| 33551 | 1 | 0 | 2.1 | 1.66 | 4.76 | 30 | 0 | 315 | 249 | 594 | 0 | 0 | 0 | 51 | 51 |
| 33851 | 1 | 0 | 2.8 | 0.96 | 4.76 | 30 | 0 | 420 | 144 | 594 | 0 | 0 | 0 | 6 | 6 |
| 34081 | 1 | 0 | 3.5 | 0.26 | 4.76 | 30 | 0 | 525 | 39 | 594 | 0 | 0 | 0 | 111 | 111 |
| 34732 | 1 | 2.76 | 0 | 1 | 4.76 | 30 | 414 | 0 | 150 | 594 | 0 | 6 | 0 | 0 | 6 |
| 35112 | 1 | 1.76 | 0 | 2 | 4.76 | 30 | 264 | 0 | 300 | 594 | 0 | 36 | 0 | 0 | 36 |
| 35392 | 1 | 0.76 | 0 | 3 | 4.76 | 30 | 114 | 0 | 450 | 594 | 0 | 6 | 0 | 0 | 6 |
| 36132 | 1 | 0 | 2.76 | 1 | 4.76 | 30 | 0 | 414 | 150 | 594 | 0 | 0 | 6 | 0 | 6 |
| 36485 | 1 | 0 | 1.76 | 2 | 4.76 | 30 | 0 | 264 | 300 | 594 | 0 | 0 | 51 | 0 | 51 |
| 36765 | 1 | 0 | 0.76 | 3 | 4.76 | 30 | 0 | 114 | 450 | 594 | 0 | 0 | 96 | 0 | 96 |
| 37659 | 0.3 | 0.4 | 3.5 | 0 | 4.2 | 9 | 60 | 525 | 0 | 594 | 21 | 0 | 0 | 0 | 21 |
| 40509 | 0.8 | 2.4 | 1.4 | 0 | 4.6 | 24 | 360 | 210 | 0 | 594 | 6 | 0 | 0 | 0 | 6 |
| 41259 | 0.3 | 3.2 | 0.7 | 0 | 4.2 | 9 | 480 | 105 | 0 | 594 | 21 | 0 | 0 | 0 | 21 |
| 42815 | 0 | 0.4 | 0.7 | 2.86 | 3.96 | 0 | 60 | 105 | 429 | 594 | 0 | 0 | 0 | 21 | 21 |
| 43235 | 0 | 0.4 | 1.4 | 2.16 | 3.96 | 0 | 60 | 210 | 324 | 594 | 0 | 0 | 0 | 126 | 126 |
| 43585 | 0 | 0.4 | 2.1 | 1.46 | 3.96 | 0 | 60 | 315 | 219 | 594 | 0 | 0 | 0 | 81 | 81 |
| 43865 | 0 | 0.4 | 2.8 | 0.76 | 3.96 | 0 | 60 | 420 | 114 | 594 | 0 | 0 | 0 | 36 | 36 |
| 44075 | 0 | 0.4 | 3.5 | 0.06 | 3.96 | 0 | 60 | 525 | 9 | 594 | 0 | 0 | 0 | 141 | 141 |
| 44695 | 0 | 1.2 | 0.7 | 2.06 | 3.96 | 0 | 180 | 105 | 309 | 594 | 0 | 0 | 0 | 141 | 141 |
| 45035 | 0 | 1.2 | 1.4 | 1.36 | 3.96 | 0 | 180 | 210 | 204 | 594 | 0 | 0 | 0 | 96 | 96 |
| 45305 | 0 | 1.2 | 2.1 | 0.66 | 3.96 | 0 | 180 | 315 | 99 | 594 | 0 | 0 | 0 | 51 | 51 |
| 46065 | 0 | 1.6 | 0.7 | 1.66 | 3.96 | 0 | 240 | 105 | 249 | 594 | 0 | 0 | 0 | 51 | 51 |
| 46365 | 0 | 1.6 | 1.4 | 0.96 | 3.96 | 0 | 240 | 210 | 144 | 594 | 0 | 0 | 0 | 6 | 6 |
| 46595 | 0 | 1.6 | 2.1 | 0.26 | 3.96 | 0 | 240 | 315 | 39 | 594 | 0 | 0 | 0 | 111 | 111 |
| 47195 | 0 | 2 | 0.7 | 1.26 | 3.96 | 0 | 300 | 105 | 189 | 594 | 0 | 0 | 0 | 111 | 111 |
| 47455 | 0 | 2 | 1.4 | 0.56 | 3.96 | 0 | 300 | 210 | 84 | 594 | 0 | 0 | 0 | 66 | 66 |
| 48105 | 0 | 2.4 | 0.7 | 0.86 | 3.96 | 0 | 360 | 105 | 129 | 594 | 0 | 0 | 0 | 21 | 21 |
| 48325 | 0 | 2.4 | 1.4 | 0.16 | 3.96 | 0 | 360 | 210 | 24 | 594 | 0 | 0 | 0 | 126 | 126 |

-continued

| | | | | | | | | | | | | | | | |
|---|---|---|---|---|---|---|---|---|---|---|---|---|---|---|---|
| 48815 | 0 | 2.8 | 0.7 | 0.46 | 3.96 | 0 | 420 | 105 | 69 | 594 | 0 | 0 | 0 | 81 | 81 |
| 49355 | 0 | 3.2 | 0.7 | 0.06 | 3.96 | 0 | 480 | 105 | 9 | 594 | 0 | 0 | 0 | 141 | 141 |
| 52409 | 0.8 | 2.8 | 0 | 1 | 4.6 | 24 | 420 | 0 | 150 | 594 | 6 | 0 | 0 | 0 | 6 |
| 54159 | 0.3 | 3.2 | 0.7 | 0 | 4.2 | 9 | 480 | 105 | 0 | 594 | 21 | 0 | 0 | 0 | 21 |
| 55309 | 0.8 | 2.4 | 1.4 | 0 | 4.6 | 24 | 360 | 210 | 0 | 594 | 6 | 0 | 0 | 0 | 6 |
| 57459 | 0.3 | 0.4 | 3.5 | 0 | 4.2 | 9 | 60 | 525 | 0 | 594 | 21 | 0 | 0 | 0 | 21 |
| 59015 | 0 | 0.4 | 0.7 | 2.86 | 3.96 | 0 | 60 | 105 | 429 | 594 | 0 | 0 | 0 | 21 | 21 |
| 59465 | 0 | 0.8 | 0.7 | 2.46 | 3.96 | 0 | 120 | 105 | 369 | 594 | 0 | 0 | 0 | 81 | 81 |
| 59875 | 0 | 1.2 | 0.7 | 2.06 | 3.96 | 0 | 180 | 105 | 309 | 594 | 0 | 0 | 0 | 141 | 141 |
| 60245 | 0 | 1.6 | 0.7 | 1.66 | 3.96 | 0 | 240 | 105 | 249 | 594 | 0 | 0 | 0 | 51 | 51 |
| 60575 | 0 | 2 | 0.7 | 1.26 | 3.96 | 0 | 300 | 105 | 189 | 594 | 0 | 0 | 0 | 111 | 111 |
| 60865 | 0 | 2.4 | 0.7 | 0.86 | 3.96 | 0 | 360 | 105 | 129 | 594 | 0 | 0 | 0 | 21 | 21 |
| 61115 | 0 | 2.8 | 0.7 | 0.46 | 3.96 | 0 | 420 | 105 | 69 | 594 | 0 | 0 | 0 | 81 | 81 |
| 61325 | 0 | 3.2 | 0.7 | 0.06 | 3.96 | 0 | 480 | 105 | 9 | 594 | 0 | 0 | 0 | 141 | 141 |
| 62125 | 0 | 0.4 | 2.1 | 1.46 | 3.96 | 0 | 60 | 315 | 219 | 594 | 0 | 0 | 0 | 81 | 81 |
| 62435 | 0 | 0.8 | 2.1 | 1.06 | 3.96 | 0 | 120 | 315 | 159 | 594 | 0 | 0 | 0 | 141 | 141 |
| 62705 | 0 | 1.2 | 2.1 | 0.66 | 3.96 | 0 | 180 | 315 | 99 | 594 | 0 | 0 | 0 | 51 | 51 |
| 62935 | 0 | 1.6 | 2.1 | 0.26 | 3.96 | 0 | 240 | 315 | 39 | 594 | 0 | 0 | 0 | 111 | 111 |
| 63765 | 0 | 0.4 | 2.8 | 0.76 | 3.96 | 0 | 60 | 420 | 114 | 594 | 0 | 0 | 0 | 36 | 36 |
| 64005 | 0 | 0.8 | 2.8 | 0.36 | 3.96 | 0 | 120 | 420 | 54 | 594 | 0 | 0 | 0 | 96 | 96 |
| 64815 | 0 | 0.4 | 3.5 | 0.06 | 3.96 | 0 | 60 | 525 | 9 | 594 | 0 | 0 | 0 | 141 | 141 |
| 67169 | 0.8 | 0 | 2.8 | 1 | 4.6 | 24 | 0 | 420 | 150 | 594 | 6 | 0 | 0 | 0 | 6 |
| 68015 | 0 | 2.26 | 0.7 | 1 | 3.96 | 0 | 339 | 105 | 150 | 594 | 0 | 21 | 0 | 0 | 21 |
| 68345 | 0 | 1.26 | 0.7 | 2 | 3.96 | 0 | 189 | 105 | 300 | 594 | 0 | 51 | 0 | 0 | 51 |
| 68575 | 0 | 0.26 | 0.7 | 3 | 3.96 | 0 | 39 | 105 | 450 | 594 | 0 | 21 | 0 | 0 | 21 |
| 69025 | 0 | 0.86 | 2.1 | 1 | 3.96 | 0 | 129 | 315 | 150 | 594 | 0 | 51 | 0 | 0 | 51 |
| 69525 | 0 | 0.16 | 2.8 | 1 | 3.96 | 0 | 24 | 420 | 150 | 594 | 0 | 36 | 0 | 0 | 36 |
| 70839 | 0.8 | 2.8 | 0 | 1 | 4.6 | 24 | 420 | 0 | 150 | 594 | 6 | 0 | 0 | 0 | 6 |
| 72439 | 0.8 | 0.8 | 0 | 3 | 4.6 | 24 | 120 | 0 | 450 | 594 | 6 | 0 | 0 | 0 | 6 |
| 73915 | 0 | 0.4 | 2.56 | 1 | 3.96 | 0 | 60 | 384 | 150 | 594 | 0 | 0 | 36 | 0 | 36 |
| 74335 | 0 | 0.8 | 2.16 | 1 | 3.96 | 0 | 120 | 324 | 150 | 594 | 0 | 0 | 96 | 0 | 96 |
| 74715 | 0 | 1.2 | 1.76 | 1 | 3.96 | 0 | 180 | 264 | 150 | 594 | 0 | 0 | 51 | 0 | 51 |
| 75055 | 0 | 1.6 | 1.36 | 1 | 3.96 | 0 | 240 | 204 | 150 | 594 | 0 | 0 | 6 | 0 | 6 |
| 75355 | 0 | 2 | 0.96 | 1 | 3.96 | 0 | 300 | 144 | 150 | 594 | 0 | 0 | 66 | 0 | 66 |
| 75615 | 0 | 2.4 | 0.56 | 1 | 3.96 | 0 | 360 | 84 | 150 | 594 | 0 | 0 | 21 | 0 | 21 |
| 75835 | 0 | 2.8 | 0.16 | 1 | 3.96 | 0 | 420 | 24 | 150 | 594 | 0 | 0 | 81 | 0 | 81 |
| 76695 | 0 | 0.4 | 1.56 | 2 | 3.96 | 0 | 60 | 234 | 300 | 594 | 0 | 0 | 81 | 0 | 81 |
| 77015 | 0 | 0.8 | 1.16 | 2 | 3.96 | 0 | 120 | 174 | 300 | 594 | 0 | 0 | 36 | 0 | 36 |
| 77295 | 0 | 1.2 | 0.76 | 2 | 3.96 | 0 | 180 | 114 | 300 | 594 | 0 | 0 | 96 | 0 | 96 |
| 77535 | 0 | 1.6 | 0.36 | 2 | 3.96 | 0 | 240 | 54 | 300 | 594 | 0 | 0 | 51 | 0 | 51 |
| 78395 | 0 | 0.4 | 0.56 | 3 | 3.96 | 0 | 60 | 84 | 450 | 594 | 0 | 0 | 21 | 0 | 21 |
| 78615 | 0 | 0.8 | 0.16 | 3 | 3.96 | 0 | 120 | 24 | 450 | 594 | 0 | 0 | 81 | 0 | 81 |
| 80179 | 0.8 | 0 | 2.8 | 1 | 4.6 | 24 | 0 | 420 | 150 | 594 | 6 | 0 | 0 | 0 | 6 |
| 82025 | 0 | 2.26 | 0.7 | 1 | 3.96 | 0 | 339 | 105 | 150 | 594 | 0 | 21 | 0 | 0 | 21 |
| 82385 | 0 | 1.56 | 1.4 | 1 | 3.96 | 0 | 234 | 210 | 150 | 594 | 0 | 6 | 0 | 0 | 6 |
| 82675 | 0 | 0.86 | 2.1 | 1 | 3.96 | 0 | 129 | 315 | 150 | 594 | 0 | 51 | 0 | 0 | 51 |
| 82895 | 0 | 0.16 | 2.8 | 1 | 3.96 | 0 | 24 | 420 | 150 | 594 | 0 | 36 | 0 | 0 | 36 |
| 83465 | 0 | 1.26 | 0.7 | 2 | 3.96 | 0 | 189 | 105 | 300 | 594 | 0 | 51 | 0 | 0 | 51 |
| 83725 | 0 | 0.56 | 1.4 | 2 | 3.96 | 0 | 84 | 210 | 300 | 594 | 0 | 36 | 0 | 0 | 36 |
| 84315 | 0 | 0.26 | 0.7 | 3 | 3.96 | 0 | 39 | 105 | 450 | 594 | 0 | 21 | 0 | 0 | 21 |

This shows additional columns, with the columns CN and Total Product (mg) repeated for readability.
VCC = vial concentration combinations, N = no, Y = yes, CND = number of different components, Sy = syringe, Instr. = instructions, NI = number of injections

| | Total Product | Vial Draws | | | | | | | Injections | | Injection 1 | | Injection 2 | | Injection 3 | |
|---|---|---|---|---|---|---|---|---|---|---|---|---|---|---|---|---|
| | | | | | | | | | 1 mL | 2 mL | Sy | | Sy | | Sy | |
| CN | (mg) | SB | P | T | B | Total | VCC | NDC | NI | Sy | Sy | Size | Instr. | Size | Instr. | Size | Instr. |
| 1 | 4.5 | 1 | 0 | 0 | 0 | 1 | N | 1 | 1 | 1 | 0 | 1 | 0.15 mL: SB; | | | | |
| 1773 | 4.5 | 0 | 1 | 0 | 0 | 1 | N | 1 | 1 | 1 | 0 | 1 | 0.03 mL: P; | | | | |
| 12272 | 4.5 | 0 | 0 | 1 | 0 | 1 | N | 1 | 1 | 1 | 0 | 1 | 0.03 mL: T; | | | | |
| 18230 | 4.5 | 0 | 0 | 0 | 1 | 1 | N | 1 | 1 | 1 | 0 | 1 | 0.03 mL: B; | | | | |
| 129 | 94.5 | 1 | 2 | 0 | 0 | 3 | Y | 2 | 2 | 2 | 0 | 1 | 1 mL: SB; | 1 | 0.4 mL: P; 0.03 mL: P; | | |
| 709 | 94.5 | 1 | 0 | 1 | 0 | 2 | Y | 2 | 2 | 2 | 0 | 1 | 1 mL: SB; | 1 | 0.43 mL: T; | | |
| 1235 | 94.5 | 1 | 0 | 0 | 1 | 2 | Y | 2 | 2 | 2 | 0 | 1 | 1 mL: SB; | 1 | 0.43 mL: B; | | |
| 1833 | 94.5 | 0 | 2 | 0 | 0 | 2 | N | 1 | 1 | 1 | 0 | 1 | 0.4 mL: P; 0.23 mL: P; | | | | |
| 3893 | 94.5 | 0 | 1 | 1 | 0 | 2 | N | 2 | 1 | 1 | 0 | 1 | 0.4 mL: P; 0.23 mL: T; | | | | |
| 8094 | 94.5 | 0 | 1 | 0 | 1 | 2 | N | 2 | 1 | 1 | 0 | 1 | 0.4 mL: P; 0.23 mL: B; | | | | |
| 12332 | 94.5 | 0 | 0 | 1 | 0 | 1 | N | 1 | 1 | 1 | 0 | 1 | 0.63 mL: T; | | | | |
| 18290 | 94.5 | 0 | 0 | 0 | 1 | 1 | N | 1 | 1 | 1 | 0 | 1 | 0.63 mL: B; | | | | |
| 22532 | 94.5 | 1 | 1 | 1 | 0 | 3 | Y | 3 | 2 | 2 | 0 | 1 | 1 mL: SB; | 1 | 0.4 mL: P; 0.03 mL: T; | | |

| | | | | | | | | | | | | | | | | | |
|---|---|---|---|---|---|---|---|---|---|---|---|---|---|---|---|---|---|
| 26434 | 94.5 | 1 | 1 | 0 | 1 | 3 | Y | 3 | 2 | 2 | 0 | 1 | 1 mL: SB; | 1 | 0.4 mL: P; 0.03 mL: B; | | |
| 181 | 172.5 | 1 | 3 | 0 | 0 | 4 | Y | 2 | 2 | 2 | 0 | 1 | 1 mL: SB; | 1 | 0.4 mL: P; 0.4 mL: P; 0.15 mL: P; | | |
| 761 | 172.5 | 1 | 0 | 2 | 0 | 3 | Y | 2 | 2 | 2 | 0 | 1 | 1 mL: SB; | 1 | 0.7 mL: T; 0.25 mL: T; | | |
| 1287 | 172.5 | 1 | 0 | 0 | 1 | 2 | Y | 2 | 2 | 2 | 0 | 1 | 1 mL: SB; | 1 | 0.95 mL: B; | | |
| 1885 | 172.5 | 0 | 3 | 0 | 0 | 3 | N | 1 | 2 | 2 | 0 | 1 | 0.35 mL: P; 0.4 mL: P; | 1 | 0.4 mL: P; | | |
| 3945 | 172.5 | 0 | 1 | 2 | 0 | 3 | N | 2 | 2 | 2 | 0 | 1 | 0.05 mL: T; 0.7 mL: T; | 1 | 0.4 mL: P; | | |
| 4465 | 172.5 | 0 | 2 | 1 | 0 | 3 | N | 2 | 2 | 2 | 0 | 1 | 0.35 mL: T; 0.4 mL: P; | 1 | 0.4 mL: P; | | |
| 8146 | 172.5 | 0 | 1 | 0 | 1 | 2 | N | 2 | 2 | 2 | 0 | 1 | 0.75 mL: B; | 1 | 0.4 mL: P; | | |
| 8666 | 172.5 | 0 | 2 | 0 | 1 | 3 | N | 2 | 2 | 2 | 0 | 1 | 0.35 mL: B; 0.4 mL: P; | 1 | 0.4 mL: P; | | |
| 12384 | 172.5 | 0 | 0 | 2 | 0 | 2 | N | 1 | 2 | 2 | 0 | 1 | 0.45 mL: T; | 1 | 0.7 mL: T; | | |
| 13714 | 172.5 | 0 | 2 | 1 | 0 | 3 | N | 2 | 2 | 2 | 0 | 1 | 0.05 mL: P; 0.7 mL: T; | 1 | 0.4 mL: P; | | |
| 15994 | 172.5 | 0 | 0 | 1 | 1 | 2 | N | 2 | 2 | 2 | 0 | 1 | 0.45 mL: B; | 1 | 0.7 mL: T; | | |
| 18342 | 172.5 | 0 | 0 | 0 | 2 | 2 | N | 1 | 2 | 2 | 0 | 1 | 0.15 mL: B; | 1 | 1 mL: B; | | |
| 18902 | 172.5 | 1 | 0 | 0 | 1 | 2 | Y | 2 | 2 | 2 | 0 | 1 | 0.75 mL: SB; | 1 | 1 mL: B; | | |
| 19542 | 172.5 | 0 | 1 | 0 | 1 | 2 | N | 2 | 2 | 2 | 0 | 1 | 0.15 mL: P; | 1 | 1 mL: B; | | |
| 21043 | 172.5 | 0 | 0 | 1 | 1 | 2 | N | 2 | 2 | 2 | 0 | 1 | 0.15 mL: T; | 1 | 1 mL: B; | | |
| 22584 | 172.5 | 1 | 1 | 1 | 0 | 3 | Y | 3 | 2 | 2 | 0 | 1 | 1 mL: SB; | 1 | 0.4 mL: P; 0.55 mL: T; | | |
| 23066 | 172.5 | 1 | 2 | 1 | 0 | 4 | Y | 3 | 2 | 2 | 0 | 1 | 1 mL: SB; | 1 | 0.4 mL: P; 0.4 mL: P; 0.15 mL: T; | | |
| 26486 | 172.5 | 1 | 1 | 0 | 1 | 3 | Y | 3 | 2 | 2 | 0 | 1 | 1 mL: SB; | 1 | 0.4 mL: P; 0.55 mL: B; | | |
| 26986 | 172.5 | 1 | 2 | 0 | 1 | 4 | Y | 3 | 2 | 2 | 0 | 1 | 1 mL: SB; | 1 | 0.4 mL: P; 0.4 mL: P; 0.15 mL: B; | | |
| 30376 | 172.5 | 1 | 1 | 1 | 0 | 3 | Y | 3 | 2 | 2 | 0 | 1 | 1 mL: SB; | 1 | 0.25 mL: P; 0.7 mL: T; | | |
| 32460 | 172.5 | 1 | 0 | 1 | 1 | 3 | Y | 3 | 2 | 2 | 0 | 1 | 1 mL: SB; | 1 | 0.7 mL: T; 0.25 mL: B; | | |
| 37254 | 172.5 | 1 | 1 | 1 | 0 | 3 | Y | 3 | 2 | 1 | 1 | 1 | 0.25 mL: SB; | 2 | 0.4 mL: P; 0.7 mL: T; | | |
| 42534 | 172.5 | 0 | 1 | 1 | 1 | 3 | N | 3 | 2 | 2 | 0 | 1 | 0.05 mL: B; 0.7 mL: T; | 1 | 0.4 mL: P; | | |
| 53454 | 172.5 | 1 | 1 | 1 | 0 | 3 | Y | 3 | 2 | 1 | 1 | 1 | 0.25 mL: SB; | 2 | 0.4 mL: P; 0.7 mL: T; | | |
| 58734 | 172.5 | 0 | 1 | 1 | 1 | 3 | N | 3 | 2 | 2 | 0 | 1 | 0.05 mL: B; 0.7 mL: T; | 1 | 0.4 mL: P; | | |
| 462 | 594 | 1 | 10 | 0 | 0 | 11 | Y | 2 | 4 | 3 | 1 | 1 | 1 mL: SB; | 1 | 0.16 mL: P; 0.4 mL: P; | 2 | 0.4 mL: P; 0.4 mL: P; 0.4 mL: P; 0.4 mL: P; |
| 1042 | 594 | 1 | 0 | 6 | 0 | 7 | Y | 2 | 4 | 2 | 2 | 1 | 1 mL: SB; | 1 | 0.26 mL: T; 0.7 mL: T; | 2 | 0.7 mL: T; 0.7 mL: T; |
| 1568 | 594 | 1 | 0 | 0 | 4 | 5 | Y | 2 | 4 | 3 | 1 | 1 | 1 mL: SB; | 1 | 0.76 mL: B; | 2 | 1 mL: B; 1 mL: B; |
| 2166 | 594 | 0 | 10 | 0 | 0 | 10 | N | 1 | 3 | 1 | 2 | 1 | 0.36 mL: P; 0.4 mL: P; | 2 | 0.4 mL: P; 0.4 mL: P; 0.4 mL: P; 0.4 mL: P; 0.4 mL: P; | 2 | 0.4 mL: P; 0.4 mL: P; 0.4 mL: P; 0.4 mL: P; |
| 4226 | 594 | 0 | 1 | 6 | 0 | 7 | N | 2 | 3 | 1 | 2 | 1 | 0.06 mL: T; 0.7 mL: T; | 2 | 0.4 mL: P; 0.7 mL: T; 0.7 mL: T; | 2 | 0.7 mL: T; 0.7 mL: T; |
| 4746 | 594 | 0 | 2 | 5 | 0 | 7 | N | 2 | 3 | 1 | 2 | 1 | 0.36 mL: T; 0.4 mL: P; | 2 | 0.4 mL: P; 0.7 mL: T; 0.7 mL: T; | 2 | 0.7 mL: T; 0.7 mL: T; |
| 5226 | 594 | 0 | 3 | 4 | 0 | 7 | N | 2 | 3 | 1 | 2 | 1 | 0.66 mL: T; | 2 | 0.4 mL: P; 0.7 mL: T; 0.7 mL: T; | 2 | 0.4 mL: P; 0.7 mL: T; 0.7 mL: T; |
| 5666 | 594 | 0 | 4 | 4 | 0 | 8 | N | 2 | 3 | 1 | 2 | 1 | 0.26 mL: T; 0.7 mL: T; | 2 | 0.4 mL: P; 0.7 mL: T; | 2 | 0.4 mL: P; 0.7 mL: T; 0.4 mL: P; |
| 6066 | 594 | 0 | 5 | 3 | 0 | 8 | N | 2 | 3 | 1 | 2 | 1 | 0.56 mL: T; 0.4 mL: P; | 2 | 0.4 mL: P; 0.7 mL: T; 0.7 mL: T; | 2 | 0.4 mL: P; 0.4 mL: P; 0.4 mL: P; |

-continued

| | | | | | | | | | | | | | | | | | |
|---|---|---|---|---|---|---|---|---|---|---|---|---|---|---|---|---|---|
| 6426 | 594 | 0 | 6 | 3 | 0 | 9 | N | 2 | 3 | 1 | 2 | 1 | 0.16 mL: T; 0.7 mL: T; | 2 | 0.4 mL: P; 0.4 mL: P; 0.4 mL: P; 0.7 mL: T; | 2 | 0.4 mL: P; 0.4 mL: P; |
| 6746 | 594 | 0 | 7 | 2 | 0 | 9 | N | 2 | 3 | 1 | 2 | 1 | 0.46 mL: T; 0.4 mL: P; | 2 | 0.4 mL: P; 0.4 mL: P; 0.7 mL: T; | 2 | 0.4 mL: P; 0.4 mL: P; |
| 7026 | 594 | 0 | 8 | 2 | 0 | 10 | N | 2 | 3 | 1 | 2 | 1 | 0.06 mL: T; 0.7 mL: T; | 2 | 0.4 mL: P; 0.4 mL: P; 0.4 mL: P; 0.4 mL: P; | 2 | 0.4 mL: P; 0.4 mL: P; 0.4 mL: P; |
| 7266 | 594 | 0 | 9 | 1 | 0 | 10 | N | 2 | 3 | 1 | 2 | 1 | 0.36 mL: T; 0.4 mL: P; | 2 | 0.4 mL: P; 0.4 mL: P; 0.4 mL: P; 0.4 mL: P; | 2 | 0.4 mL: P; 0.4 mL: P; |
| 8427 | 594 | 0 | 1 | 0 | 4 | 5 | N | 2 | 3 | 2 | 1 | 1 | 0.56 mL: B; 0.4 mL: P; | 2 | 1 mL: B; 1 mL: B; | 1 | 1 mL: B; |
| 8947 | 594 | 0 | 2 | 0 | 4 | 6 | N | 2 | 3 | 2 | 1 | 1 | 0.16 mL: B; 0.4 mL: P; | 2 | 1 mL: B; 1 mL: B; | 1 | 1 mL: B; |
| 9427 | 594 | 0 | 3 | 0 | 3 | 6 | N | 2 | 3 | 1 | 2 | 1 | 0.76 mL: B; | 2 | 1 mL: B; 1 mL: B; | 2 | 0.4 mL: P; 0.4 mL: P; |
| 9867 | 594 | 0 | 4 | 0 | 3 | 7 | N | 2 | 3 | 1 | 2 | 1 | 0.36 mL: B; 0.4 mL: P; | 2 | 1 mL: B; 1 mL: B; | 2 | 0.4 mL: P; 0.4 mL: P; |
| 10267 | 594 | 0 | 5 | 0 | 2 | 7 | N | 2 | 3 | 1 | 2 | 1 | 0.96 mL: B; | 2 | 0.4 mL: P; 0.4 mL: P; 1 mL: B; | 2 | 0.4 mL: P; 0.4 mL: P; |
| 10627 | 594 | 0 | 6 | 0 | 2 | 8 | N | 2 | 3 | 1 | 2 | 1 | 0.56 mL: B; 0.4 mL: P; | 2 | 0.4 mL: P; 0.4 mL: P; 1 mL: B; | 2 | 0.4 mL: P; 0.4 mL: P; |
| 10947 | 594 | 0 | 7 | 0 | 2 | 9 | N | 2 | 3 | 1 | 2 | 1 | 0.16 mL: B; 0.4 mL: P; 0.4 mL: P; | 2 | 0.4 mL: P; 0.4 mL: P; 1 mL: B; | 2 | 0.4 mL: P; 0.4 mL: P; |
| 11227 | 594 | 0 | 8 | 0 | 1 | 9 | N | 2 | 3 | 1 | 2 | 1 | 0.76 mL: B; | 2 | 0.4 mL: P; 0.4 mL: P; 0.4 mL: P; 0.4 mL: P; | 2 | 0.4 mL: P; 0.4 mL: P; 0.4 mL: P; 0.4 mL: P; |
| 11467 | 594 | 0 | 9 | 0 | 1 | 10 | N | 2 | 3 | 1 | 2 | 1 | 0.36 mL: B; 0.4 mL: P; | 2 | 0.4 mL: P; 0.4 mL: P; 0.4 mL: P; 0.4 mL: P; | 2 | 0.4 mL: P; 0.4 mL: P; 0.4 mL: P; 0.4 mL: P; |
| 12665 | 594 | 0 | 0 | 6 | 0 | 6 | N | 1 | 4 | 2 | 2 | 1 | 0.46 mL: T; | 2 | 0.7 mL: T; 0.7 mL: T; | 2 | 0.7 mL: T; 0.7 mL: T; |
| 13995 | 594 | 0 | 9 | 1 | 0 | 10 | N | 2 | 3 | 1 | 2 | 1 | 0.06 mL: P; 0.7 mL: T; | 2 | 0.4 mL: P; 0.4 mL: P; 0.4 mL: P; 0.4 mL: P; | 2 | 0.4 mL: P; 0.4 mL: P; 0.4 mL: P; 0.4 mL: P; |
| 14455 | 594 | 0 | 7 | 2 | 0 | 9 | N | 2 | 3 | 1 | 2 | 1 | 0.16 mL: P; 0.7 mL: T; | 2 | 0.4 mL: P; 0.4 mL: P; 0.7 mL: T; | 2 | 0.4 mL: P; 0.4 mL: P; 0.7 mL: T; |
| 14845 | 594 | 0 | 5 | 3 | 0 | 8 | N | 2 | 3 | 1 | 2 | 1 | 0.26 mL: P; 0.7 mL: T; | 2 | 0.4 mL: P; 0.7 mL: T; 0.7 mL: T; | 2 | 0.4 mL: P; 0.4 mL: P; 0.7 mL: T; |
| 15165 | 594 | 0 | 3 | 4 | 0 | 7 | N | 2 | 3 | 1 | 2 | 1 | 0.36 mL: P; 0.4 mL: P; | 2 | 0.4 mL: P; 0.7 mL: T; 0.7 mL: T; | 2 | 0.7 mL: T; 0.7 mL: T; 0.7 mL: T; |
| 15415 | 594 | 0 | 2 | 5 | 0 | 7 | N | 2 | 3 | 1 | 2 | 1 | 0.06 mL: P; 0.7 mL: T; | 2 | 0.4 mL: P; 0.7 mL: T; 0.7 mL: T; | 2 | 0.7 mL: T; 0.7 mL: T; 0.7 mL: T; |
| 16275 | 594 | 0 | 0 | 1 | 4 | 5 | N | 2 | 3 | 2 | 1 | 1 | 0.26 mL: B; 0.7 mL: T; | 2 | 1 mL: B; 1 mL: B; | 1 | 1 mL: B; |
| 16735 | 594 | 0 | 0 | 2 | 3 | 5 | N | 2 | 3 | 1 | 2 | 1 | 0.56 mL: B; | 2 | 1 mL: B; 1 mL: B; | 2 | 0.7 mL: T; 0.7 mL: T; |
| 17125 | 594 | 0 | 0 | 3 | 2 | 5 | N | 2 | 3 | 1 | 2 | 1 | 0.86 mL: B; | 2 | 0.7 mL: T; 1 mL: B; | 2 | 0.7 mL: T; 0.7 mL: T; |
| 17445 | 594 | 0 | 0 | 4 | 2 | 6 | N | 2 | 3 | 1 | 2 | 1 | 0.16 mL: B; 0.7 mL: T; | 2 | 0.7 mL: T; 1 mL: B; | 2 | 0.7 mL: T; 0.7 mL: T; |
| 17695 | 594 | 0 | 0 | 5 | 1 | 6 | N | 2 | 4 | 2 | 2 | 1 | 0.46 mL: B; | 2 | 0.7 mL: T; 0.7 mL: T; | 2 | 0.7 mL: T; 0.7 mL: T; |

-continued

| | | | | | | | | | | | | | | | | | |
|---|---|---|---|---|---|---|---|---|---|---|---|---|---|---|---|---|---|
| 18623 | 594 | 0 | 0 | 0 | 4 | 4 | N | 1 | 3 | 2 | 1 | 1 | 0.96 mL: B; | 2 | 1 mL: B; 1 mL: B; | 1 | 1 mL: B; |
| 19823 | 594 | 0 | 8 | 0 | 1 | 9 | N | 2 | 3 | 1 | 2 | 1 | 0.16 mL: P; 0.4 mL: P; 0.4 mL: P; | 2 | 0.4 mL: P; 0.4 mL: P; 1 mL: B; | 2 | 0.4 mL: P; 0.4 mL: P; 0.4 mL: P; |
| 20223 | 594 | 0 | 5 | 0 | 2 | 7 | N | 2 | 3 | 1 | 2 | 1 | 0.36 mL: P; 0.4 mL: P; | 2 | 1 mL: B; 1 mL: B; | 2 | 0.4 mL: P; 0.4 mL: P; |
| 20523 | 594 | 0 | 3 | 0 | 3 | 6 | N | 2 | 3 | 2 | 1 | 1 | 0.16 mL: P; 0.4 mL: P; 0.4 mL: P; | 2 | 1 mL: B; 1 mL: B; | 1 | 1 mL: B; |
| 21324 | 594 | 0 | 0 | 5 | 1 | 6 | N | 2 | 3 | 1 | 2 | 1 | 0.16 mL: P; 0.7 mL: T; | 2 | 0.7 mL: T; 1 mL: B; | 2 | 0.7 mL: T; 0.7 mL: T; |
| 21724 | 594 | 0 | 0 | 3 | 2 | 5 | N | 2 | 3 | 1 | 2 | 1 | 0.56 mL: T; | 2 | 1 mL: B; 1 mL: B; | 2 | 0.7 mL: T; 0.7 mL: T; |
| 22024 | 594 | 0 | 0 | 2 | 3 | 5 | N | 2 | 3 | 2 | 1 | 1 | 0.26 mL: T; 0.7 mL: T; | 2 | 1 mL: B; 1 mL: B; | 1 | 1 mL: B; |
| 22865 | 594 | 1 | 1 | 5 | 0 | 7 | Y | 3 | 4 | 2 | 2 | 1 | 1 mL: SB; | 1 | 0.56 mL: T; 0.4 mL: P; | 2 | 0.7 mL: T; 0.7 mL: T; |
| 23347 | 594 | 1 | 2 | 5 | 0 | 8 | Y | 3 | 4 | 2 | 2 | 1 | 1 mL: SB; | 1 | 0.16 mL: T; 0.7 mL: T; 0.7 mL: T; | 2 | 0.4 mL: P; 0.7 mL: T; |
| 23807 | 594 | 1 | 3 | 4 | 0 | 8 | Y | 3 | 4 | 2 | 2 | 1 | 1 mL: SB; | 1 | 0.46 mL: T; 0.4 mL: P; | 2 | 0.4 mL: P; 0.7 mL: T; |
| 24227 | 594 | 1 | 4 | 4 | 0 | 9 | Y | 3 | 4 | 2 | 2 | 1 | 1 mL: SB; | 1 | 0.06 mL: T; 0.7 mL: T; | 2 | 0.4 mL: P; 0.7 mL: T; |
| 24607 | 594 | 1 | 5 | 3 | 0 | 9 | Y | 3 | 4 | 2 | 2 | 1 | 1 mL: SB; | 1 | 0.36 mL: T; 0.4 mL: P; | 2 | 0.4 mL: P; 0.7 mL: T; |
| 24947 | 594 | 1 | 6 | 2 | 0 | 9 | Y | 3 | 4 | 2 | 2 | 1 | 1 mL: SB; | 1 | 0.66 mL: T; | 2 | 0.4 mL: P; 0.4 mL: P; 0.7 mL: T; |
| 25247 | 594 | 1 | 7 | 2 | 0 | 10 | Y | 3 | 4 | 3 | 1 | 1 | 1 mL: SB; | 1 | 0.26 mL: T; 0.7 mL: T; | 2 | 0.4 mL: P; 0.4 mL: P; 0.4 mL: P; 0.4 mL: P; |
| 25507 | 594 | 1 | 8 | 1 | 0 | 10 | Y | 3 | 4 | 3 | 1 | 1 | 1 mL: SB; | 1 | 0.56 mL: T; 0.4 mL: P; | 2 | 0.4 mL: P; 0.4 mL: P; 0.4 mL: P; 0.4 mL: P; |
| 25727 | 594 | 1 | 9 | 1 | 0 | 11 | Y | 3 | 4 | 3 | 1 | 1 | 1 mL: SB; | 1 | 0.16 mL: T; 0.4 mL: P; 0.4 mL: P; | 2 | 0.4 mL: P; 0.4 mL: P; 0.4 mL: P; 0.4 mL: P; |
| 26767 | 594 | 1 | 1 | 0 | 4 | 6 | Y | 3 | 4 | 3 | 1 | 1 | 1 mL: SB; | 1 | 0.36 mL: B; 0.4 mL: P; | 2 | 1 mL: B; 1 mL: B; |
| 27267 | 594 | 1 | 2 | 0 | 3 | 6 | Y | 3 | 4 | 3 | 1 | 1 | 1 mL: SB; | 1 | 0.96 mL: B; | 2 | 1 mL: B; 1 mL: B; |
| 27727 | 594 | 1 | 3 | 0 | 3 | 7 | Y | 3 | 4 | 3 | 1 | 1 | 1 mL: SB; | 1 | 0.56 mL: B; 0.4 mL: P; | 2 | 1 mL: B; 1 mL: B; |
| 28147 | 594 | 1 | 4 | 0 | 3 | 8 | Y | 3 | 4 | 3 | 1 | 1 | 1 mL: SB; | 1 | 0.16 mL: B; 0.4 mL: P; 0.4 mL: P; | 2 | 1 mL: B; 1 mL: B; |
| 28527 | 594 | 1 | 5 | 0 | 2 | 8 | Y | 3 | 4 | 2 | 2 | 1 | 1 mL: SB; | 1 | 0.76 mL: B; | 2 | 0.4 mL: P; 0.4 mL: P; 1 mL: B; |
| 28867 | 594 | 1 | 6 | 0 | 2 | 9 | Y | 3 | 4 | 2 | 2 | 1 | 1 mL: SB; | 1 | 0.36 mL: B; 0.4 mL: P; | 2 | 0.4 mL: P; 0.4 mL: P; 1 mL: B; |
| 29167 | 594 | 1 | 7 | 0 | 1 | 9 | Y | 3 | 4 | 3 | 1 | 1 | 1 mL: SB; | 1 | 0.96 mL: B; | 2 | 0.4 mL: P; 0.4 mL: P; 0.4 mL: P; 0.4 mL: P; |
| 29427 | 594 | 1 | 8 | 0 | 1 | 10 | Y | 3 | 4 | 3 | 1 | 1 | 1 mL: SB; | 1 | 0.56 mL: B; 0.4 mL: P; | 2 | 0.4 mL: P; 0.4 mL: P; 0.4 mL: P; 0.4 mL: P; 0.4 mL: P; |

-continued

| | | | | | | | | | | | | | | | | | |
|---|---|---|---|---|---|---|---|---|---|---|---|---|---|---|---|---|---|
| 29647 | 594 | 1 | 9 | 0 | 1 | 11 | Y | 3 | 4 | 3 | 1 | 1 | 1 mL: SB; | 1 | 0.16 mL: B; 0.4 mL: P; 0.4 mL: P; 0.4 mL: P; | 2 | 0.4 mL: P; 0.4 mL: P; 0.4 mL: P; 0.4 mL: P; |
| 30657 | 594 | 1 | 8 | 1 | 0 | 10 | Y | 3 | 4 | 3 | 1 | 1 | 1 mL: SB; | 1 | 0.26 mL: P; 0.7 mL: T; | 2 | 0.4 mL: P; 0.4 mL: P; 0.4 mL: P; 0.4 mL: P; |
| 31097 | 594 | 1 | 6 | 2 | 0 | 9 | Y | 3 | 4 | 2 | 2 | 1 | 1 mL: SB; | 1 | 0.36 mL: P; 0.4 mL: P; | 2 | 0.4 mL: P; 0.7 mL: T; 0.7 mL: T; |
| 31467 | 594 | 1 | 5 | 3 | 0 | 9 | Y | 3 | 4 | 2 | 2 | 1 | 1 mL: SB; | 1 | 0.06 mL: P; 0.7 mL: T; | 2 | 0.4 mL: P; 0.7 mL: T; 0.7 mL: T; |
| 31767 | 594 | 1 | 3 | 4 | 0 | 8 | Y | 3 | 4 | 2 | 2 | 1 | 1 mL: SB; | 1 | 0.16 mL: P; 0.7 mL: T; | 2 | 0.4 mL: P; 0.7 mL: T; 0.7 mL: T; |
| 31997 | 594 | 1 | 1 | 5 | 0 | 7 | Y | 3 | 4 | 2 | 2 | 1 | 1 mL: SB; | 1 | 0.26 mL: P; 0.7 mL: T; | 2 | 0.7 mL: T; 0.7 mL: T; |
| 32741 | 594 | 1 | 0 | 1 | 4 | 6 | Y | 3 | 4 | 3 | 1 | 1 | 1 mL: SB; | 1 | 0.06 mL: B; 0.7 mL: T; | 2 | 1 mL: B; 1 mL: B; |
| 33181 | 594 | 1 | 0 | 2 | 3 | 6 | Y | 3 | 4 | 2 | 2 | 1 | 1 mL: SB; | 1 | 0.36 mL: B; | 2 | 1 mL: B; 1 mL: B; |
| 33551 | 594 | 1 | 0 | 3 | 2 | 6 | Y | 3 | 4 | 2 | 2 | 1 | 1 mL: SB; | 1 | 0.66 mL: B; | 2 | 0.7 mL: T; 1 mL: B; |
| 33851 | 594 | 1 | 0 | 4 | 1 | 6 | Y | 3 | 4 | 2 | 2 | 1 | 1 mL: SB; | 1 | 0.96 mL: B; | 2 | 0.7 mL: T; 0.7 mL: T; |
| 34081 | 594 | 1 | 0 | 5 | 1 | 7 | Y | 3 | 4 | 2 | 2 | 1 | 1 mL: SB; | 1 | 0.26 mL: B; 0.7 mL: T; | 2 | 0.7 mL: T; 0.7 mL: T; |
| 34732 | 594 | 1 | 7 | 0 | 1 | 9 | Y | 3 | 4 | 2 | 2 | 1 | 1 mL: SB; | 1 | 0.36 mL: P; 0.4 mL: P; | 2 | 0.4 mL: P; 0.4 mL: P; 1 mL: B; |
| 35112 | 594 | 1 | 5 | 0 | 2 | 8 | Y | 3 | 4 | 3 | 1 | 1 | 1 mL: SB; | 1 | 0.16 mL: P; 0.4 mL: P; 0.4 mL: P; | 2 | 1 mL: B; 1 mL: B; |
| 35392 | 594 | 1 | 2 | 0 | 3 | 6 | Y | 3 | 4 | 3 | 1 | 1 | 1 mL: SB; | 1 | 0.36 mL: P; 0.4 mL: P; | 2 | 1 mL: B; 1 mL: B; |
| 36132 | 594 | 1 | 0 | 4 | 1 | 6 | Y | 3 | 4 | 2 | 2 | 1 | 1 mL: SB; | 1 | 0.66 mL: T; | 2 | 0.7 mL: T; 1 mL: B; |
| 36485 | 594 | 1 | 0 | 3 | 2 | 6 | Y | 3 | 4 | 2 | 2 | 1 | 1 mL: SB; | 1 | 0.36 mL: T; | 2 | 1 mL: B; 1 mL: B; |
| 36765 | 594 | 1 | 0 | 2 | 3 | 6 | Y | 3 | 4 | 3 | 1 | 1 | 1 mL: SB; | 1 | 0.06 mL: T; 0.7 mL: T; | 2 | 1 mL: B; 1 mL: B; |
| 37659 | 594 | 1 | 1 | 5 | 0 | 7 | Y | 3 | 4 | 2 | 2 | 1 | 0.3 mL: SB; | 2 | 0.4 mL: P; 0.7 mL: T; 0.7 mL: T; | 2 | 0.7 mL: T; |
| 40509 | 594 | 1 | 6 | 2 | 0 | 9 | Y | 3 | 3 | 1 | 2 | 1 | 0.8 mL: SB; | 2 | 0.4 mL: P; 0.4 mL: P; 0.4 mL: P; 0.4 mL: P; | 2 | 0.4 mL: P; 0.7 mL: T; |
| 41259 | 594 | 1 | 8 | 1 | 0 | 10 | Y | 3 | 3 | 1 | 2 | 1 | 0.3 mL: SB; | 2 | 0.4 mL: P; 0.4 mL: P; 0.4 mL: P; 0.4 mL: P; 0.4 mL: P; | 2 | 0.4 mL: P; 0.4 mL: P; 0.4 mL: P; 0.7 mL: T; |
| 42815 | 594 | 0 | 1 | 1 | 3 | 5 | N | 3 | 3 | 1 | 2 | 1 | 0.86 mL: B; | 2 | 1 mL: B; 1 mL: B; | 2 | 0.4 mL: P; 0.7 mL: T; |
| 43235 | 594 | 0 | 1 | 2 | 3 | 6 | N | 3 | 3 | 1 | 2 | 1 | 0.16 mL: B; 0.7 mL: T; | 2 | 1 mL: B; 1 mL: B; | 2 | 0.4 mL: P; 0.7 mL: T; |
| 43585 | 594 | 0 | 1 | 3 | 2 | 6 | N | 3 | 3 | 1 | 2 | 1 | 0.46 mL: P; 0.4 mL: P; | 2 | 0.7 mL: T; 1 mL: B; | 2 | 0.7 mL: T; 0.7 mL: T; |
| 43865 | 594 | 0 | 1 | 4 | 1 | 6 | N | 3 | 3 | 1 | 2 | 1 | 0.76 mL: B; | 2 | 0.4 mL: P; 0.7 mL: T; | 2 | 0.7 mL: T; 0.7 mL: T; |
| 44075 | 594 | 0 | 1 | 5 | 1 | 7 | N | 3 | 3 | 1 | 2 | 1 | 0.06 mL: B; 0.7 mL: T; | 2 | 0.4 mL: P; 0.7 mL: T; | 2 | 0.7 mL: T; 0.7 mL: T; |
| 44695 | 594 | 0 | 3 | 1 | 3 | 7 | N | 3 | 3 | 1 | 2 | 1 | 0.06 mL: B; 0.7 mL: T; | 2 | 1 mL: B; 1 mL: B; | 2 | 0.4 mL: P; 0.4 mL: P; 0.4 mL: P; |
| 45035 | 594 | 0 | 3 | 2 | 2 | 7 | N | 3 | 3 | 1 | 2 | 1 | 0.36 mL: B; 0.4 mL: P; | 2 | 0.7 mL: T; 1 mL: B; | 2 | 0.4 mL: P; 0.4 mL: P; 0.7 mL: T; |
| 45305 | 594 | 0 | 3 | 3 | 1 | 7 | N | 3 | 3 | 1 | 2 | 1 | 0.66 mL: B; | 2 | 0.4 mL: P; 0.7 mL: T; 0.7 mL: T; | 2 | 0.4 mL: P; 0.4 mL: P; 0.7 mL: T; |

-continued

| | | | | | | | | | | | | | | | | | |
|---|---|---|---|---|---|---|---|---|---|---|---|---|---|---|---|---|---|
| 46065 | 594 | 0 | 4 | 1 | 2 | 7 | N | 3 | 3 | 1 | 2 | 1 | 0.66 mL: B;<br>1 mL: B; | 2 | 0.7 mL: T;<br>0.4 mL: P;<br>0.4 mL: P; | 2 | 0.4 mL: P;<br>0.4 mL: P;<br>0.4 mL: P; |
| 46365 | 594 | 0 | 4 | 2 | 1 | 7 | N | 3 | 3 | 1 | 2 | 1 | 0.96 mL: B; | 2 | 0.4 mL: P;<br>0.7 mL: T;<br>0.7 mL: T; | 2 | 0.4 mL: P;<br>0.4 mL: P;<br>0.4 mL: P; |
| 46595 | 594 | 0 | 4 | 3 | 1 | 8 | N | 3 | 3 | 1 | 2 | 1 | 0.26 mL: B;<br>0.7 mL: T; | 2 | 0.4 mL: P;<br>0.7 mL: T;<br>0.7 mL: T; | 2 | 0.4 mL: P;<br>0.4 mL: P;<br>0.4 mL: P; |
| 47195 | 594 | 0 | 5 | 1 | 2 | 8 | N | 3 | 3 | 1 | 2 | 1 | 0.26 mL: B;<br>0.7 mL: T; | 2 | 0.4 mL: P;<br>0.4 mL: P;<br>1 mL: B; | 2 | 0.4 mL: P;<br>0.4 mL: P;<br>0.4 mL: P; |
| 47455 | 594 | 0 | 5 | 2 | 1 | 8 | N | 3 | 3 | 1 | 2 | 1 | 0.56 mL: B;<br>0.4 mL: P; | 2 | 0.7 mL: T;<br>0.7 mL: T;<br>0.7 mL: T; | 2 | 0.4 mL: P;<br>0.4 mL: P;<br>0.4 mL: P; |
| 48105 | 594 | 0 | 6 | 1 | 1 | 8 | N | 3 | 3 | 1 | 2 | 1 | 0.86 mL: B; | 2 | 0.4 mL: P;<br>0.4 mL: P;<br>0.7 mL: T; | 2 | 0.4 mL: P;<br>0.4 mL: P;<br>0.4 mL: P; |
| 48325 | 594 | 0 | 6 | 2 | 1 | 9 | N | 3 | 3 | 1 | 2 | 1 | 0.16 mL: B;<br>0.7 mL: T; | 2 | 0.4 mL: P;<br>0.4 mL: P;<br>0.7 mL: T; | 2 | 0.4 mL: P;<br>0.4 mL: P;<br>0.4 mL: P; |
| 48815 | 594 | 0 | 7 | 1 | 1 | 9 | N | 3 | 3 | 1 | 2 | 1 | 0.46 mL: B;<br>0.4 mL: P; | 2 | 0.4 mL: P;<br>0.4 mL: P;<br>0.7 mL: T; | 2 | 0.4 mL: P;<br>0.4 mL: P;<br>0.4 mL: P; |
| 49355 | 594 | 0 | 8 | 1 | 1 | 10 | N | 3 | 3 | 1 | 2 | 1 | 0.06 mL: B;<br>0.7 mL: T; | 2 | 0.4 mL: P;<br>0.4 mL: P;<br>0.4 mL: P;<br>0.4 mL: P; | 2 | 0.4 mL: P;<br>0.4 mL: P; |
| 52409 | 594 | 1 | 7 | 0 | 1 | 9 | Y | 3 | 3 | 1 | 2 | 1 | 0.8 mL: SB; | 2 | 0.4 mL: P;<br>0.4 mL: P;<br>0.4 mL: P;<br>0.4 mL: P; | 2 | 0.4 mL: P;<br>0.4 mL: P;<br>1 mL: B; |
| 54159 | 594 | 1 | 8 | 1 | 0 | 10 | Y | 3 | 3 | 1 | 2 | 1 | 0.3 mL: SB; | 2 | 0.4 mL: P;<br>0.4 mL: P;<br>0.4 mL: P;<br>0.4 mL: P; | 2 | 0.4 mL: P;<br>0.4 mL: P;<br>0.4 mL: P;<br>0.7 mL: T; |
| 55309 | 594 | 1 | 6 | 2 | 0 | 9 | Y | 3 | 3 | 1 | 2 | 1 | 0.8 mL: SB; | 2 | 0.4 mL: P;<br>0.4 mL: P;<br>0.4 mL: P;<br>0.4 mL: P; | 2 | 0.4 mL: P;<br>0.7 mL: T;<br>0.7 mL: T; |
| 57459 | 594 | 1 | 1 | 5 | 0 | 7 | Y | 3 | 4 | 2 | 2 | 1 | 0.3 mL: SB;<br>0.7 mL: T; | 2 | 0.7 mL: T;<br>0.7 mL: T; | 2 | 0.7 mL: T;<br>0.7 mL: T; |
| 59015 | 594 | 0 | 1 | 1 | 3 | 5 | N | 3 | 3 | 1 | 2 | 1 | 0.86 mL: B; | 2 | 1 mL: B;<br>1 mL: B; | 2 | 0.4 mL: P;<br>0.7 mL: T; |
| 59465 | 594 | 0 | 2 | 1 | 3 | 6 | N | 3 | 3 | 1 | 2 | 1 | 0.46 mL: B;<br>0.4 mL: P; | 2 | 1 mL: B;<br>1 mL: B; | 2 | 0.4 mL: P;<br>0.7 mL: T; |
| 59875 | 594 | 0 | 3 | 1 | 3 | 7 | N | 3 | 3 | 1 | 2 | 1 | 0.06 mL: B;<br>0.7 mL: T; | 2 | 1 mL: B;<br>1 mL: B; | 2 | 0.4 mL: P;<br>0.4 mL: P; |
| 60245 | 594 | 0 | 4 | 1 | 2 | 7 | N | 3 | 3 | 1 | 2 | 1 | 0.66 mL: B; | 2 | 0.7 mL: T;<br>1 mL: B; | 2 | 0.4 mL: P;<br>0.4 mL: P;<br>0.4 mL: P; |
| 60575 | 594 | 0 | 5 | 1 | 2 | 8 | N | 3 | 3 | 1 | 2 | 1 | 0.26 mL: B;<br>0.7 mL: T; | 2 | 0.4 mL: P;<br>0.4 mL: P;<br>1 mL: B; | 2 | 0.4 mL: P;<br>0.4 mL: P;<br>0.4 mL: P; |
| 60865 | 594 | 0 | 6 | 1 | 1 | 8 | N | 3 | 3 | 1 | 2 | 1 | 0.86 mL: B; | 2 | 0.4 mL: P;<br>0.4 mL: P;<br>0.7 mL: T; | 2 | 0.4 mL: P;<br>0.4 mL: P;<br>0.4 mL: P; |
| 61115 | 594 | 0 | 7 | 1 | 1 | 9 | N | 3 | 3 | 1 | 2 | 1 | 0.46 mL: B;<br>0.4 mL: P; | 2 | 0.4 mL: P;<br>0.4 mL: P;<br>0.7 mL: T; | 2 | 0.4 mL: P;<br>0.4 mL: P;<br>0.4 mL: P; |
| 61325 | 594 | 0 | 8 | 1 | 1 | 10 | N | 3 | 3 | 1 | 2 | 1 | 0.06 mL: B;<br>0.7 mL: T; | 2 | 0.4 mL: P;<br>0.4 mL: P;<br>0.4 mL: P;<br>0.4 mL: P; | 2 | 0.4 mL: P;<br>0.4 mL: P;<br>0.4 mL: P;<br>0.4 mL: P; |

-continued

| | | | | | | | | | | | | | | | | | |
|---|---|---|---|---|---|---|---|---|---|---|---|---|---|---|---|---|---|
| 62125 | 594 | 0 | 1 | 3 | 2 | 6 | N | 3 | 3 | 1 | 2 | 1 | 0.46 mL: B; 0.4 mL: P; | 2 | 0.7 mL: T; 1 mL: B; | 2 | 0.7 mL: T; |
| 62435 | 594 | 0 | 2 | 3 | 2 | 7 | N | 3 | 3 | 1 | 2 | 1 | 0.06 mL: B; 0.7 mL: T; | 2 | 0.4 mL: P; 1 mL: B; | 2 | 0.4 mL: P; 0.7 mL: T; |
| 62705 | 594 | 0 | 3 | 3 | 1 | 7 | N | 3 | 3 | 1 | 2 | 1 | 0.66 mL: B; | 2 | 0.4 mL: P; 0.7 mL: T; | 2 | 0.4 mL: P; 0.4 mL: P; 0.7 mL: T; |
| 62935 | 594 | 0 | 4 | 3 | 1 | 8 | N | 3 | 3 | 1 | 2 | 1 | 0.26 mL: B; | 2 | 0.4 mL: P; 0.7 mL: T; | 2 | 0.4 mL: P; 0.7 mL: T; 0.4 mL: P; |
| 63765 | 594 | 0 | 1 | 4 | 1 | 6 | N | 3 | 3 | 1 | 2 | 1 | 0.76 mL: B; | 2 | 0.4 mL: P; 0.7 mL: T; | 2 | 0.7 mL: T; 0.7 mL: T; |
| 64005 | 594 | 0 | 2 | 4 | 1 | 7 | N | 3 | 3 | 1 | 2 | 1 | 0.36 mL: B; 0.4 mL: P; | 2 | 0.4 mL: P; 0.7 mL: T; | 2 | 0.7 mL: T; 0.7 mL: T; |
| 64815 | 594 | 0 | 1 | 5 | 1 | 7 | N | 3 | 3 | 1 | 2 | 1 | 0.06 mL: B; 0.7 mL: T; | 2 | 0.4 mL: P; 0.7 mL: T; | 2 | 0.7 mL: T; 0.7 mL: T; |
| 67169 | 594 | 1 | 0 | 4 | 1 | 6 | Y | 3 | 4 | 2 | 2 | 1 | 0.8 mL: SB; | 2 | 0.7 mL: T; 1 mL: B; | 2 | 0.7 mL: T; 0.7 mL: T; |
| 68015 | 594 | 0 | 6 | 1 | 1 | 8 | N | 3 | 3 | 1 | 2 | 1 | 0.26 mL: P; 0.7 mL: T; | 2 | 0.4 mL: P; 1 mL: B; | 2 | 0.4 mL: P; 0.4 mL: P; |
| 68345 | 594 | 0 | 4 | 1 | 2 | 7 | N | 3 | 3 | 1 | 2 | 1 | 0.06 mL: P; 0.7 mL: T; | 2 | 1 mL: B; 1 mL: B; | 2 | 0.4 mL: P; 0.4 mL: P; |
| 68575 | 594 | 0 | 1 | 1 | 3 | 5 | N | 3 | 3 | 2 | 1 | 1 | 0.26 mL: P; 0.7 mL: T; | 2 | 1 mL: B; 1 mL: B; | 1 | 1 mL: B; |
| 69025 | 594 | 0 | 3 | 3 | 1 | 7 | N | 3 | 3 | 1 | 2 | 1 | 0.06 mL: P; 0.7 mL: T; | 2 | 0.7 mL: T; 1 mL: B; | 2 | 0.4 mL: P; 0.7 mL: T; |
| 69525 | 594 | 0 | 1 | 4 | 1 | 6 | N | 3 | 3 | 1 | 2 | 1 | 0.16 mL: P; 0.7 mL: T; | 2 | 0.7 mL: T; 1 mL: B; | 2 | 0.7 mL: T; 0.7 mL: T; |
| 70839 | 594 | 1 | 7 | 0 | 1 | 9 | Y | 3 | 3 | 1 | 2 | 1 | 0.8 mL: SB; | 2 | 0.4 mL: P; 0.4 mL: P; 0.4 mL: P; 0.4 mL: P; | 2 | 0.4 mL: P; 0.4 mL: P; 1 mL: B; |
| 72439 | 594 | 1 | 2 | 0 | 3 | 6 | Y | 3 | 3 | 1 | 2 | 1 | 0.8 mL: SB; | 2 | 1 mL: B; 1 mL: B; | 2 | 0.4 mL: P; 0.4 mL: P; 1 mL: B; |
| 73915 | 594 | 0 | 1 | 4 | 1 | 6 | N | 3 | 3 | 1 | 2 | 1 | 0.46 mL: T; 0.4 mL: P; | 2 | 0.7 mL: T; 1 mL: B; | 2 | 0.7 mL: T; 0.7 mL: T; |
| 74335 | 594 | 0 | 2 | 4 | 1 | 7 | N | 3 | 3 | 1 | 2 | 1 | 0.06 mL: T; 0.7 mL: T; | 2 | 0.7 mL: T; 1 mL: B; | 2 | 0.4 mL: P; 0.7 mL: T; |
| 74715 | 594 | 0 | 3 | 3 | 1 | 7 | N | 3 | 3 | 1 | 2 | 1 | 0.36 mL: T; 0.4 mL: P; | 2 | 0.7 mL: T; 1 mL: B; | 2 | 0.4 mL: P; 0.7 mL: T; |
| 75055 | 594 | 0 | 4 | 2 | 1 | 7 | N | 3 | 3 | 1 | 2 | 1 | 0.66 mL: T; | 2 | 0.7 mL: T; 1 mL: B; | 2 | 0.4 mL: P; 0.4 mL: P; 0.4 mL: P; |
| 75355 | 594 | 0 | 5 | 2 | 1 | 8 | N | 3 | 3 | 1 | 2 | 1 | 0.26 mL: T; 0.7 mL: T; | 2 | 0.4 mL: P; 1 mL: B; | 2 | 0.4 mL: P; 0.4 mL: P; 0.4 mL: P; |
| 75615 | 594 | 0 | 6 | 1 | 1 | 8 | N | 3 | 3 | 1 | 2 | 1 | 0.56 mL: T; 0.4 mL: P; | 2 | 0.4 mL: P; 1 mL: B; | 2 | 0.4 mL: P; 0.4 mL: P; |
| 75835 | 594 | 0 | 7 | 1 | 1 | 9 | N | 3 | 3 | 1 | 2 | 1 | 0.16 mL: T; 0.4 mL: P; 0.4 mL: P; | 2 | 0.4 mL: P; 1 mL: B; | 2 | 0.4 mL: P; 0.4 mL: P; |
| 76695 | 594 | 0 | 1 | 3 | 2 | 6 | N | 3 | 3 | 1 | 2 | 1 | 0.16 mL: T; 0.7 mL: T; | 2 | 1 mL: B; 1 mL: B; | 2 | 0.4 mL: P; 0.7 mL: T; |
| 77015 | 594 | 0 | 2 | 2 | 2 | 6 | N | 3 | 3 | 1 | 2 | 1 | 0.46 mL: T; 0.4 mL: P; | 2 | 1 mL: B; 1 mL: B; | 2 | 0.4 mL: P; 0.7 mL: T; |
| 77295 | 594 | 0 | 3 | 2 | 2 | 7 | N | 3 | 3 | 1 | 2 | 1 | 0.06 mL: T; 0.7 mL: T; | 2 | 1 mL: B; 1 mL: B; | 2 | 0.4 mL: P; 0.4 mL: P; |
| 77535 | 594 | 0 | 4 | 1 | 2 | 7 | N | 3 | 3 | 1 | 2 | 1 | 0.36 mL: T; 0.4 mL: P; | 2 | 1 mL: B; 1 mL: B; | 2 | 0.4 mL: P; 0.4 mL: P; |
| 78395 | 594 | 0 | 1 | 1 | 3 | 5 | N | 3 | 3 | 2 | 1 | 1 | 0.56 mL: T; 0.4 mL: P; | 2 | 1 mL: B; 1 mL: B; | 1 | 1 mL: B; |
| 78615 | 594 | 0 | 2 | 1 | 3 | 6 | N | 3 | 3 | 2 | 1 | 1 | 0.16 mL: T; 0.4 mL: P; 0.4 mL: P; | 2 | 1 mL: B; 1 mL: B; | 1 | 1 mL: B; |

-continued

| | | | | | | | | | | | | | | | | | |
|---|---|---|---|---|---|---|---|---|---|---|---|---|---|---|---|---|---|
| 80179 | 594 | 1 | 0 | 4 | 1 | 6 | Y | 3 | 4 | 2 | 2 | 1 | 0.8 mL: SB; | 2 | 0.7 mL: T; 1 mL: B; | 2 | 0.7 mL: T; 0.7 mL: T; |
| 82025 | 594 | 0 | 6 | 1 | 1 | 8 | N | 3 | 3 | 1 | 2 | 1 | 0.26 mL: P; 0.7 mL: T; | 2 | 0.4 mL: P; 0.4 mL: P; 1 mL: B; | 2 | 0.4 mL: P; 0.4 mL: P; 0.4 mL: P; |
| 82385 | 594 | 0 | 4 | 2 | 1 | 7 | N | 3 | 3 | 1 | 2 | 1 | 0.36 mL: P; 0.4 mL: P; | 2 | 0.7 mL: T; 1 mL: B; | 2 | 0.4 mL: P; 0.4 mL: P; 0.7 mL: T; |
| 82675 | 594 | 0 | 3 | 3 | 1 | 7 | N | 3 | 3 | 1 | 2 | 1 | 0.06 mL: P; 0.7 mL: T; | 2 | 0.7 mL: T; 1 mL: B; | 2 | 0.4 mL: P; 0.4 mL: P; 0.7 mL: T; |
| 82895 | 594 | 0 | 1 | 4 | 1 | 6 | N | 3 | 3 | 1 | 2 | 1 | 0.16 mL: P; 0.7 mL: T; | 2 | 0.7 mL: T; 1 mL: B; | 2 | 0.7 mL: T; 0.7 mL: T; |
| 83465 | 594 | 0 | 4 | 1 | 2 | 7 | N | 3 | 3 | 1 | 2 | 1 | 0.06 mL: P; 0.7 mL: T; | 2 | 1 mL: B; 1 mL: B; | 2 | 0.4 mL: P; 0.4 mL: P; 0.4 mL: P; |
| 83725 | 594 | 0 | 2 | 2 | 2 | 6 | N | 3 | 3 | 1 | 2 | 1 | 0.16 mL: P; 0.7 mL: T; | 2 | 1 mL: B; 1 mL: B; | 2 | 0.4 mL: P; 0.7 mL: T; |
| 84315 | 594 | 0 | 1 | 1 | 3 | 5 | N | 3 | 3 | 2 | 1 | 1 | 0.26 mL: P; 0.7 mL: T; | 2 | 1 mL: B; 1 mL: B; | 1 | 1 mL: B; |

Table 2 shows a subset of data (30 out of 147 rows) in a "least wastage—loading phase" recommendations table generated in the present exemplary embodiment. As mentioned above, the loading phase regimen only includes one type of administration regimen (weekly, 3 mg/kg, for 4 weeks) in this example. In the table below, Wt=weight of patient (kg), TD=total dose (mg), TV=total volume (ml), #V=number of vials, Vol.=volume, SB=sky blue, P=purple, T=turquoise, B=brown, VD=vial draws, SB ml=total amount SB product (ml), P ml=total amount P product (ml), T ml=total amount T product (ml), B ml=total amount B product (ml).

| | | 30 mg/1.0 mL (30 mg/mL) SB vial | | | | 60 mg/0.4 mL (150 mg/mL) P vial | | | | 105 mg/0.7 mL (150 mg/mL) T vial | | | |
|---|---|---|---|---|---|---|---|---|---|---|---|---|---|
| | | Full vial | | Part vial | | Full vial | | Part vial | | Full vial | | Part vial | |
| Wt | TD | # V | Vol. | # V | Vol. | # V | Vol. | # V | Vol. | # V | Vol. | # V | |
| 5 | 15 | | | 1 | 0.5 | | | | | | | | |
| 10 | 30 | 1 | 1 | | | | | | | | | | |
| 15 | 45 | | | | | | | | 0.3 | | | | |
| 20 | 60 | | | | | 1 | | | 0.4 | | | | |
| 25 | 75 | | | 1 | 0.5 | | | 1 | 0.4 | | | | |
| 30 | 90 | 1 | 1 | | | | | 1 | 0.4 | | | | |
| 35 | 105 | | | | | | | | | 1 | 0.7 | | |
| 40 | 120 | | | | | 2 | 0.4 | | | | | | |
| 45 | 135 | 1 | 1 | | | | | | | 1 | 0.7 | | |
| 50 | 150 | | | | | | | | | | | | |
| 55 | 165 | | | | | 1 | 0.4 | | | 1 | 0.7 | | |
| 60 | 180 | | | | | 3 | 0.4 | | | | | | |
| 65 | 195 | 1 | 1 | | | 1 | 0.4 | | | 1 | 0.7 | | |
| 70 | 210 | | | | | | | | | 2 | 0.7 | | |
| 75 | 225 | | | | | 2 | 0.4 | | | 1 | 0.7 | | |
| 80 | 240 | | | | | 4 | 0.4 | | | | | | |
| 85 | 255 | | | | | | | | | 1 | 0.7 | | |
| 90 | 270 | | | | | 2 | 0.4 | | | | | | |
| 95 | 285 | | | | | 3 | 0.4 | | | 1 | 0.7 | | |
| 100 | 300 | | | | | | | | | | | | |
| 105 | 315 | | | | | | | | | 3 | 0.7 | | |
| 110 | 330 | 1 | 1 | | | | | | | | | | |
| 115 | 345 | | | | | 4 | 0.4 | | | 1 | 0.7 | | |
| 120 | 360 | | | | | 1 | 0.4 | | | | | | |
| 125 | 375 | | | | | 1 | 0.4 | | | 3 | 2.1 | | |
| 130 | 390 | | | | | 4 | 0.4 | | | | | | |
| 135 | 405 | | | | | | | | | 1 | 0.7 | | |

-continued

| | | | | | | | | | |
|---|---|---|---|---|---|---|---|---|---|
| 140 | 420 | | | | | | | 4 | 0.7 |
| 145 | 435 | | | 2 | 0.4 | | | 3 | 0.7 |
| 150 | 450 | | | | | | | | |

Table 2 (continued) shows additional columns - the weight column is repeated for ease of reading. In the table below, Wt = weight of patient (kg), WA4 = waste over 4 weeks (mg), VCC = vial concentration combinations, Ni = number of injections, Sy S = syringe size (ml), Instr. = instructions, VD = total vial draws, SB W4 = sky blue waste over 4 weeks (ml), P W4 = purple waste over 4 weeks (ml), T W4 = turquoise waste over 4 weeks (ml), B W4 = brown waste over 4 weeks (ml), SB mg = total SB product (mg), T mg = total T product (mg), P mg = total P product (mg), B mg = total B product (mg), TD = total dose (mg), SB VD = SB vial draws, SB = sky blue, P = purple, T = turquoise, B = brown, Syr = syringes.

| | | 105 mg/0.7 mL (150 mg/mL) T vial Part vial | 150 mg/1.0 mL (150 mg/mL) B vial | | | | | | SB | P | T | B |
|---|---|---|---|---|---|---|---|---|---|---|---|---|
| | | | Full vial | | Part vial | | | | | | | |
| Wt | TD | Vol. | # V | Vol. | # V | Vol. | TV | VD | ml | ml | ml | ml |
| 5 | 15 | | | | | | 0.5 | 1 | 0.5 | 0 | 0 | 0 |
| 10 | 30 | | | | | | 1 | 1 | 1 | 0 | 0 | 0 |
| 15 | 45 | | | | | | 0.3 | 1 | 0 | 0.3 | 0 | 0 |
| 20 | 60 | | | | | | 0.4 | 1 | 0 | 0.4 | 0 | 0 |
| 25 | 75 | | | | | | 0.9 | 2 | 0.5 | 0.4 | 0 | 0 |
| 30 | 90 | | | | | | 1.4 | 2 | 1 | 0.4 | 0 | 0 |
| 35 | 105 | | | | | | 0.7 | 1 | 0 | 0 | 0.7 | 0 |
| 40 | 120 | | | | | | 0.8 | 2 | 0 | 0.8 | 0 | 0 |
| 45 | 135 | | | | | | 1.7 | 2 | 1 | 0 | 0.7 | 0 |
| 50 | 150 | | 1 | 1 | | | 1 | 1 | 0 | 0 | 0 | 1 |
| 55 | 165 | | | | | | 1.1 | 2 | 0 | 0.4 | 0.7 | 0 |
| 60 | 180 | | | | | | 1.2 | 3 | 0 | 1.2 | 0 | 0 |
| 65 | 195 | | | | | | 2.1 | 3 | 1 | 0.4 | 0.7 | 0 |
| 70 | 210 | | | | | | 1.4 | 2 | 0 | 0 | 1.4 | 0 |
| 75 | 225 | | | | | | 1.5 | 3 | 0 | 0.8 | 0.7 | 0 |
| 80 | 240 | | | | | | 1.6 | 4 | 0 | 1.6 | 0 | 0 |
| 85 | 255 | | 1 | 1 | | | 1.7 | 2 | 0 | 0 | 0.7 | 1 |
| 90 | 270 | | 1 | 1 | | | 1.8 | 3 | 0 | 0.8 | 0 | 1 |
| 95 | 285 | | | | | | 1.9 | 4 | 0 | 1.2 | 0.7 | 0 |
| 100 | 300 | | 2 | 1 | | | 2 | 2 | 0 | 0 | 0 | 2 |
| 105 | 315 | | | | | | 2.1 | 3 | 0 | 0 | 2.1 | 0 |
| 110 | 330 | | 2 | 1 | | | 3 | 3 | 1 | 0 | 0 | 2 |
| 115 | 345 | | | | | | 2.3 | 5 | 0 | 1.6 | 0.7 | 0 |
| 120 | 360 | | 2 | 1 | | | 2.4 | 3 | 0 | 0.4 | 0 | 2 |
| 125 | 375 | | | | | | 2.5 | 4 | 0 | 0.4 | 2.1 | 0 |
| 130 | 390 | | 1 | 1 | | | 2.6 | 5 | 0 | 1.6 | 0 | 1 |
| 135 | 405 | | 2 | 1 | | | 2.7 | 3 | 0 | 0 | 0.7 | 2 |
| 140 | 420 | | | | | | 2.8 | 4 | 0 | 0 | 2.8 | 0 |
| 145 | 435 | | | | | | 2.9 | 5 | 0 | 0.8 | 2.1 | 0 |
| 150 | 450 | | 3 | 1 | | | 3 | 3 | 0 | 0 | 0 | 3 |

Table 3 (continued) shows additional columns - the weight column is repeated for ease of reading. In the table below, all abbreviations are as in Table 2.

| | | | | | | Syr (n) | | | SB | P | T | B | SB | P | T | B | |
|---|---|---|---|---|---|---|---|---|---|---|---|---|---|---|---|---|---|
| | | Inj. 1 | | Inj. 2 | | 1 | 2 | | | | | | | | | | |
| Wt | VCC | SyS | Instr. | SyS | Instr. | ml | ml | NI | W4 | W4 | W4 | W4 | mg | mg | mg | mg | TD |
| 5 | | 1 | 0.5 mL: SB; | | | 1 | 0 | 1 | 30 | 1 | 0 | 0 | 15 | 0 | 0 | 0 | 15 |
| 10 | | 1 | 1 mL: SB; | | | 1 | 0 | 1 | 0 | 0 | 0 | 0 | 30 | 0 | 0 | 0 | 30 |
| 15 | | 1 | 0.3 mL: P; | | | 1 | 0 | 1 | 30 | 0 | 0.2 | 0 | 0 | 45 | 0 | 0 | 45 |
| 20 | | 1 | 0.4 mL: P; | | | 1 | 0 | 1 | 0 | 0 | 0 | 0 | 0 | 60 | 0 | 0 | 60 |
| 25 | X | 1 | 0.5 mL: SB; | 1 | 0.4 mL: P | 2 | 0 | 2 | 30 | 1 | 0 | 0 | 15 | 60 | 0 | 0 | 75 |
| 30 | X | 1 | 1 mL: SB; | 1 | 0.4 mL: P | 2 | 0 | 2 | 0 | 0 | 0 | 0 | 30 | 60 | 0 | 0 | 90 |
| 35 | | 1 | 0.7 mL: T; | | | 1 | 0 | 1 | 0 | 0 | 0 | 0 | 0 | 0 | 105 | 0 | 105 |
| 40 | | 1 | 0.4 mL: P; 0.4 mL: P; | | | 1 | 0 | 1 | 0 | 0 | 0 | 0 | 0 | 120 | 0 | 0 | 120 |
| 45 | X | 1 | 1 mL: SB; | 1 | 0.7 mL: T | 2 | 0 | 2 | 0 | 0 | 0 | 0 | 30 | 0 | 105 | 0 | 135 |
| 50 | | 1 | 1 mL: B; | | | 1 | 0 | 1 | 0 | 0 | 0 | 0 | 0 | 0 | 0 | 150 | 150 |
| 55 | | 2 | 0.4 mL: P; 0.7 mL: T; | | | 0 | 1 | 1 | 0 | 0 | 0 | 0 | 0 | 60 | 105 | 0 | 165 |
| 60 | | 2 | 0.4 mL: P; 0.4 mL: P; 0.4 mL: P; | | | 0 | 1 | 1 | 0 | 0 | 0 | 0 | 0 | 180 | 0 | 0 | 180 |
| 65 | X | 1 | 1 mL: SB; | 2 | 0.4 mL: P 0.7 mL: T | 1 | 1 | 2 | 0 | 0 | 0 | 0 | 30 | 60 | 105 | 0 | 195 |
| 70 | | 2 | 0.7 mL: T; 0.7 mL: T; | | | 0 | 1 | 1 | 0 | 0 | 0 | 0 | 0 | 0 | 210 | 0 | 210 |

| | | | | | | | | | | | | | | | | | | | |
|---|---|---|---|---|---|---|---|---|---|---|---|---|---|---|---|---|---|---|---|
| 75 | | 2 | 0.4 mL: P;<br>0.4 mL: P;<br>0.7 mL: T; | | | 0 | 1 | 1 | 0 | 0 | 0 | 0 | 0 | 0 | 120 | 105 | 0 | 225 |
| 80 | | 2 | 0.4 mL: P;<br>0.4 mL: P;<br>0.4 mL: P;<br>0.4 mL: P; | | | 0 | 1 | 1 | 0 | 0 | 0 | 0 | 0 | 0 | 240 | 0 | 0 | 240 |
| 85 | | 2 | 0.7 mL: T;<br>1 mL: B; | | | 0 | 1 | 1 | 0 | 0 | 0 | 0 | 0 | 0 | 0 | 105 | 150 | 255 |
| 90 | | 2 | 0.4 mL: P;<br>0.4 mL: P;<br>1 mL: B; | | | 0 | 1 | 1 | 0 | 0 | 0 | 0 | 0 | 0 | 120 | 0 | 150 | 270 |
| 95 | | 2 | 0.4 mL: P;<br>0.4 mL: P;<br>0.4 mL: P;<br>0.7 mL: T; | | | 0 | 1 | 1 | 0 | 0 | 0 | 0 | 0 | 0 | 180 | 105 | 0 | 285 |
| 100 | | 2 | 1 mL: B;<br>1 mL: B; | | | 0 | 1 | 1 | 0 | 0 | 0 | 0 | 0 | 0 | 0 | 0 | 300 | 300 |
| 105 | | 2 | 0.7 mL: T;<br>0.7 mL: T; | 1 | 0.7 mL: T | 1 | 1 | 2 | 0 | 0 | 0 | 0 | 0 | 0 | 0 | 315 | 0 | 315 |
| 110 | X | 1 | 1 mL: SB; | 2 | 1 mL: B<br>1 mL: B | 1 | 1 | 2 | 0 | 0 | 0 | 0 | 30 | 0 | 0 | 300 | 330 |
| 115 | | 2 | 0.4 mL: P;<br>0.4 mL: P;<br>0.4 mL: P;<br>0.7 mL: T; | 1 | 0.4 mL: P | 1 | 1 | 2 | 0 | 0 | 0 | 0 | 0 | 0 | 240 | 105 | 0 | 345 |
| 120 | | 2 | 1 mL: B;<br>1 mL: B; | 1 | 0.4 mL: P | 1 | 1 | 2 | 0 | 0 | 0 | 0 | 0 | 0 | 60 | 0 | 300 | 360 |
| 125 | | 2 | 0.4 mL: P;<br>0.7 mL: T;<br>0.7 mL: T; | 1 | 0.7 mL: T | 1 | 1 | 2 | 0 | 0 | 0 | 0 | 0 | 0 | 60 | 315 | 0 | 375 |
| 130 | | 2 | 0.4 mL: P;<br>0.4 mL: P;<br>1 mL: B; | 1 | 0.4 mL: P<br>0.4 mL: P | 1 | 1 | 2 | 0 | 0 | 0 | 0 | 0 | 0 | 240 | 0 | 150 | 390 |
| 135 | | 2 | 1 mL: B;<br>1 mL: B; | 1 | 0.7 mL: T | 1 | 1 | 2 | 0 | 0 | 0 | 0 | 0 | 0 | 0 | 105 | 300 | 405 |
| 140 | | 2 | 0.7 mL: T;<br>0.7 mL: T; | 2 | 0.7 mL: T<br>0.7 mL: T | 0 | 2 | 2 | 0 | 0 | 0 | 0 | 0 | 0 | 0 | 420 | 0 | 420 |
| 145 | | 2 | 0.4 mL: P;<br>0.7 mL: T;<br>0.7 mL: T; | 2 | 0.4 mL: P<br>0.7 mL: T | 0 | 2 | 2 | 0 | 0 | 0 | 0 | 0 | 0 | 120 | 315 | 0 | 435 |
| 150 | | 2 | 1 mL: B;<br>1 mL: B; | 1 | 1 mL: B | 1 | 1 | 2 | 0 | 0 | 0 | 0 | 0 | 0 | 0 | 0 | 450 | 450 |

Table 3 shows a subset of data (30 out of 147 rows) in a "least injections—loading phase" recommendations table generated in the present exemplary embodiment. As mentioned above, the loading phase regimen only includes one type of administration regimen (weekly, 3 mg/kg, for 4 weeks) in this example. In the table below, all abbreviations are as in Table 2.

| | | 30 mg/1.0 mL<br>(30 mg/mL) SB vial | | | | 60 mg/0.4 mL<br>(150 mg/mL) P vial | | | | 105 mg/0.7 mL<br>(150 mg/mL) T vial | | | | 150 mg/1.0 mL<br>(150 mg/mL) B vial | | | | | | | | |
|---|---|---|---|---|---|---|---|---|---|---|---|---|---|---|---|---|---|---|---|---|---|---|
| | | Full vial | | Part vial | | Full vial | | Part vial | | Full vial | | Part vial | | Full vial | | Part vial | | | | SB | P | T | B |
| Wt | TD | #V | Vol. | # V | Vol. | # V | Vol. | # V | Vol. | #V | Vol. | # V | Vol. | #V | Vol. | #V | Vol. | TV | VD | ml | ml | ml | ml |
| 5 | 15 | | | 1 | 0.5 | | | | | | | | | | | | | 0.5 | 1 | 0.5 | 0 | 0 | 0 |
| 10 | 30 | 1 | 1 | | | | | | | | | | | | | | | 1 | 1 | 1 | 0 | 0 | 0 |
| 15 | 45 | | | | | | | 1 | 0.3 | | | | | | | | | 0.3 | 1 | 0 | 0.3 | 0 | 0 |
| 20 | 60 | | | | | 1 | 0.4 | | | | | | | | | | | 0.4 | 1 | 0 | 0.4 | 0 | 0 |
| 25 | 75 | | | | | | | | | 1 | 0.5 | | | | | | | 0.5 | 1 | 0 | 0 | 0.5 | 0 |
| 30 | 90 | | | | | | | | | 1 | 0.6 | | | | | | | 0.6 | 1 | 0 | 0 | 0.6 | 0 |
| 35 | 105 | | | | | | | | | 1 | 0.7 | | | | | | | 0.7 | 1 | 0 | 0 | 0.7 | 0 |
| 40 | 120 | | | | | | | | | | | | | | | 1 | 0.8 | 0.8 | 1 | 0 | 0 | 0 | 0.8 |
| 45 | 135 | | | | | | | | | | | | | | | 1 | 0.9 | 0.9 | 1 | 0 | 0 | 0 | 0.9 |
| 50 | 150 | | | | | | | | | | | | | 1 | 1 | | | 1 | 1 | 0 | 0 | 0 | 1 |
| 55 | 165 | | | | | 1 | 0.4 | | | 1 | 0.7 | | | | | | | 1.1 | 2 | 0 | 0.4 | 0.7 | 0 |
| 60 | 180 | | | | | | | | | 1 | 0.7 | 1 | 0.5 | | | | | 1.2 | 2 | 0 | 0 | 1.2 | 0 |
| 65 | 195 | | | | | | | | | 1 | 0.7 | 1 | 0.6 | | | | | 1.3 | 2 | 0 | 0 | 1.3 | 0 |
| 70 | 210 | | | | | | | | | 2 | 0.7 | | | | | | | 1.4 | 2 | 0 | 0 | 1.4 | 0 |
| 75 | 225 | | | | | | | | | 1 | 0.5 | 1 | 1 | | | | | 1.5 | 2 | 0 | 0 | 0.5 | 1 |
| 80 | 240 | | | | | | | | | 1 | 0.6 | 1 | 1 | | | | | 1.6 | 2 | 0 | 0 | 0.6 | 1 |

-continued

| Wt | VCC | | | | | | | | | | | | | | | | | | | | | |
|---|---|---|---|---|---|---|---|---|---|---|---|---|---|---|---|---|---|---|---|---|---|---|
| 85 | 255 | | | | | | | | | 1 | 0.7 | | | | | 1 | 1 | | | 1.7 | 2 | 0 | 0 | 0.7 | 1 |
| 90 | 270 | | | | | | | | | | | | | | | 1 | 1 | 1 | 0.8 | 1.8 | 2 | 0 | 0 | 0 | 1.8 |
| 95 | 285 | | | | | | | | | | | | | | | 1 | 1 | 1 | 0.9 | 1.9 | 2 | 0 | 0 | 0 | 1.9 |
| 100 | 300 | | | | | | | | | | | | | | | 2 | 1 | | | 2 | 2 | 0 | 0 | 0 | 2 |
| 105 | 315 | | | | | | | | 3 | 0.7 | | | | | | | | | | 2.1 | 3 | 0 | 0 | 2.1 | 0 |
| 110 | 330 | 1 | 1 | | | | | | | | | | | | | 2 | 1 | | | 3 | 3 | 1 | 0 | 0 | 2 |
| 115 | 345 | | | | | 1 | 0.3 | | | | | | | | | 2 | 1 | | | 2.3 | 3 | 0 | 0.3 | 0 | 2 |
| 120 | 360 | | | 1 | 0.4 | | | | | | | | | | | 2 | 1 | | | 2.4 | 3 | 0 | 0.4 | 0 | 2 |
| 125 | 375 | | | | | | | | | | | 1 | 0.5 | | | 2 | 1 | | | 2.5 | 3 | 0 | 0 | 0.5 | 2 |
| 130 | 390 | | | | | | | | | | | 1 | 0.6 | | | 2 | 1 | | | 2.6 | 3 | 0 | 0 | 0.6 | 2 |
| 135 | 405 | | | | | | | | 1 | 0.7 | | | | | | 2 | 1 | | | 2.7 | 3 | 0 | 0 | 0.7 | 2 |
| 140 | 420 | | | | | | | | | | | | | | | 2 | 1 | 1 | 0.8 | 2.8 | 3 | 0 | 0 | 0 | 2.8 |
| 145 | 435 | | | | | | | | | | | | | | | 2 | 1 | 1 | 0.9 | 2.9 | 3 | 0 | 0 | 0 | 2.9 |
| 150 | 450 | | | | | | | | | | | | | | | 3 | 1 | | | 3 | 3 | 0 | 0 | 0 | 3 |

| | | Inj. 1 | | Inj. 2 | | Syr (n) | | | | | | | | | | | | | |
|---|---|---|---|---|---|---|---|---|---|---|---|---|---|---|---|---|---|---|---|
| | | | | | | 1 | 2 | | SB | P | T | B | SB | P | T | B | | | |
| Wt | VCC | SyS | Instr. | SyS | Instr. | ml | ml | NI | W4 | W4 | W4 | W4 | W4 | mg | mg | mg | mg | mg | TD |
| 5 | | 1 | 0.5 mL: SB; | | | 1 | 0 | 1 | 30 | 1 | 0 | 0 | 0 | 15 | 0 | 0 | 0 | | 15 |
| 10 | | 1 | 1 mL: SB; | | | 1 | 0 | 1 | 0 | 0 | 0 | 0 | 0 | 30 | 0 | 0 | 0 | | 30 |
| 15 | | 1 | 0.3 mL: P; | | | 1 | 0 | 1 | 30 | 0 | 0.2 | 0 | 0 | 0 | 45 | 0 | 0 | | 45 |
| 20 | | 1 | 0.4 mL: P; | | | 1 | 0 | 1 | 0 | 0 | 0 | 0 | 0 | 0 | 60 | 0 | 0 | | 60 |
| 25 | | 1 | 0.5 mL: T; | | | 1 | 0 | 1 | 60 | 0 | 0 | 0.4 | 0 | 0 | 0 | 75 | 0 | | 75 |
| 30 | | 1 | 0.6 mL: T; | | | 1 | 0 | 1 | 30 | 0 | 0 | 0.2 | 0 | 0 | 0 | 90 | 0 | | 90 |
| 35 | | 1 | 0.7 mL: T; | | | 1 | 0 | 1 | 0 | 0 | 0 | 0 | 0 | 0 | 0 | 105 | 0 | | 105 |
| 40 | | 1 | 0.8 mL: B; | | | 1 | 0 | 1 | 60 | 0 | 0 | 0 | 0.4 | 0 | 0 | 0 | 120 | | 120 |
| 45 | | 1 | 0.9 mL: B; | | | 1 | 0 | 1 | 30 | 0 | 0 | 0 | 0.2 | 0 | 0 | 0 | 135 | | 135 |
| 50 | | 1 | 1 mL: B; | | | 1 | 0 | 1 | 0 | 0 | 0 | 0 | 0 | 0 | 0 | 0 | 150 | | 150 |
| 55 | | 2 | 0.4 mL: P; 0.7 mL: T; | | | 0 | 1 | 1 | 0 | 0 | 0 | 0 | 0 | 0 | 60 | 105 | 0 | | 165 |
| 60 | | 2 | 0.7 mL: T; 0.5 mL: T; | | | 0 | 1 | 1 | 60 | 0 | 0 | 0.4 | 0 | 0 | 0 | 180 | 0 | | 180 |
| 65 | | 2 | 0.7 mL: T; 0.6 mL: T; | | | 0 | 1 | 1 | 30 | 0 | 0 | 0.2 | 0 | 0 | 0 | 195 | 0 | | 195 |
| 70 | | 2 | 0.7 mL: T; 0.7 mL: T; | | | 0 | 1 | 1 | 0 | 0 | 0 | 0 | 0 | 0 | 0 | 210 | 0 | | 210 |
| 75 | | 2 | 0.5 mL: T; 1 mL: B; | | | 0 | 1 | 1 | 60 | 0 | 0 | 0.4 | 0 | 0 | 0 | 75 | 150 | | 225 |
| 80 | | 2 | 0.6 mL: T; 1 mL: B; | | | 0 | 1 | 1 | 30 | 0 | 0 | 0.2 | 0 | 0 | 0 | 90 | 150 | | 240 |
| 85 | | 2 | 0.7 mL: T; 1 mL: B; | | | 0 | 1 | 1 | 0 | 0 | 0 | 0 | 0 | 0 | 0 | 105 | 150 | | 255 |
| 90 | | 2 | 1 mL: B; 0.8 mL: B; | | | 0 | 1 | 1 | 60 | 0 | 0 | 0 | 0.4 | 0 | 0 | 0 | 270 | | 270 |
| 95 | | 2 | 1 mL: B; 0.9 mL: B; | | | 0 | 1 | 1 | 30 | 0 | 0 | 0 | 0.2 | 0 | 0 | 0 | 285 | | 285 |
| 100 | | 2 | 1 mL: B; 1 mL: B; | | | 0 | 1 | 1 | 0 | 0 | 0 | 0 | 0 | 0 | 0 | 0 | 300 | | 300 |
| 105 | | 2 | 0.7 mL: T; 0.7 mL: T; | 1 | 0.7 mL: T; | 1 | 1 | 2 | 0 | 0 | 0 | 0 | 0 | 0 | 0 | 315 | 0 | | 315 |
| 110 | X | 1 | 1 mL: SB; | 2 | 1 mL: B; 1 mL: B; | 1 | 1 | 2 | 0 | 0 | 0 | 0 | 0 | 30 | 0 | 0 | 300 | | 330 |
| 115 | | 2 | 1 mL: B; 1 mL: B; | 1 | 0.3 mL: P; | 1 | 1 | 2 | 30 | 0 | 0.2 | 0 | 0 | 0 | 45 | 0 | 300 | | 345 |
| 120 | | 2 | 1 mL: B; 1 mL: B; | 1 | 0.4 mL: P; | 1 | 1 | 2 | 0 | 0 | 0 | 0 | 0 | 0 | 60 | 0 | 300 | | 360 |
| 125 | | 2 | 1 mL: B; 1 mL: B; | 1 | 0.5 mL: T; | 1 | 1 | 2 | 60 | 0 | 0 | 0.4 | 0 | 0 | 0 | 75 | 300 | | 375 |
| 130 | | 2 | 1 mL: B; 1 mL: B; | 1 | 0.6 mL: T; | 1 | 1 | 2 | 30 | 0 | 0 | 0.2 | 0 | 0 | 0 | 90 | 300 | | 390 |
| 135 | | 2 | 1 mL: B; 1 mL: B; | 1 | 0.7 mL: T; | 1 | 1 | 2 | 0 | 0 | 0 | 0 | 0 | 0 | 0 | 105 | 300 | | 405 |
| 140 | | 2 | 1 mL: B; 1 mL: B; | 1 | 0.8 mL: B; | 1 | 1 | 2 | 60 | 0 | 0 | 0 | 0.4 | 0 | 0 | 0 | 420 | | 420 |
| 145 | | 2 | 1 mL: B; 1 mL: B; | 1 | 0.9 mL: B; | 1 | 1 | 2 | 30 | 0 | 0 | 0 | 0.2 | 0 | 0 | 0 | 435 | | 435 |
| 150 | | 2 | 1 mL: B; 1 mL: B; | 1 | 1 mL: B; | 1 | 1 | 2 | 0 | 0 | 0 | 0 | 0 | 0 | 0 | 0 | 450 | | 450 |

Table 4 shows a subset of data (45 out of 441 rows) in a "least wastage—maintenance phase" recommendations table generated in the present exemplary embodiment. As mentioned above, the maintenance phase regimen includes three types of administration regimen (1.5 mg/kg/week, 3 mg/kg/2 weeks, 6 mg/kg/4 weeks) in this example. In the table below, all abbreviations are as in Table 2.

|  |  | 30 mg/1.0 mL (30 mg/mL) SB | | | | 60 mg/0.4 mL (150 mg/mL) P | | | | 105 mg/0.7 mL (150 mg/mL) T vial | | | |
|---|---|---|---|---|---|---|---|---|---|---|---|---|---|
|  |  | Full | | Part vial | | Full vial | | Part vial | | Full vial | | Part vial | |
| Wt | TD | # V | Vol. | # V | Vol. | # V | Vol | # V | Vol. | # V | Vol. | # V | Vol. |
| Maintenance Dose - 1.5 mg/kg/week | | | | | | | | | | | | | |
| 5 | 7.5 |  |  | 1 | 0.25 |  |  |  |  |  |  |  |  |
| 15 | 22.5 |  |  | 1 | 0.75 |  |  |  |  |  |  |  |  |
| 25 | 37.5 |  |  |  |  |  |  | 1 | 0.25 |  |  |  |  |
| 35 | 52.5 |  |  |  |  |  |  | 1 | 0.35 |  |  |  |  |
| 45 | 67.5 |  |  | 1 | 0.25 | 1 | 0.4 |  |  |  |  |  |  |
| 55 | 82.5 |  |  | 1 | 0.75 | 1 | 0.4 |  |  |  |  |  |  |
| 65 | 97.5 |  |  |  |  |  |  |  |  |  |  | 1 | 0.65 |
| 75 | 112.5 |  |  |  |  | 1 | 0.4 | 1 | 0.35 |  |  |  |  |
| 85 | 127.5 |  |  | 1 | 0.75 |  |  |  |  | 1 | 0.7 |  |  |
| 95 | 142.5 |  |  |  |  |  |  |  |  |  |  |  |  |
| 105 | 157.5 |  |  |  |  | 1 | 0.35 | 1 | 0.7 |  |  |  |  |
| 115 | 172.5 |  |  | 1 | 0.75 |  |  |  |  |  |  |  |  |
| 125 | 187.5 |  |  | 1 | 0.75 | 1 | 0.4 |  |  | 1 | 0.7 |  |  |
| 135 | 202.5 |  |  |  |  |  |  |  |  | 1 | 0.7 | 1 | 0.65 |
| 145 | 217.5 |  |  |  |  | 1 | 0.4 | 1 | 0.35 | 1 | 0.7 |  |  |
| Maintenance Dose - 3 mg/kg/2 week | | | | | | | | | | | | | |
| 5 | 15 |  |  | 1 | 0.5 |  |  |  |  |  |  |  |  |
| 15 | 45 |  |  |  |  |  |  | 1 | 0.3 |  |  |  |  |
| 25 | 75 |  |  | 1 | 0.5 | 1 | 0.4 |  |  |  |  |  |  |
| 35 | 105 |  |  |  |  |  |  |  |  | 1 | 0.7 |  |  |
| 45 | 135 | 1 | 1 |  |  |  |  |  |  | 1 | 0.7 |  |  |
| 55 | 165 |  |  |  |  | 1 | 0.4 |  |  | 1 | 0.7 |  |  |
| 65 | 195 | 1 | 1 |  |  | 1 | 0.4 |  |  | 1 | 0.7 |  |  |
| 75 | 225 |  |  |  |  | 2 | 0.4 |  |  | 1 | 0.7 |  |  |
| 85 | 255 |  |  |  |  |  |  |  |  | 1 | 0.7 |  |  |
| 95 | 285 |  |  |  |  | 3 | 0.4 |  |  | 1 | 0.7 |  |  |
| 105 | 315 |  |  |  |  |  |  |  |  | 3 | 0.7 |  |  |
| 115 | 345 |  |  |  |  | 4 | 0.4 |  |  | 1 | 0.7 |  |  |
| 125 | 375 |  |  |  |  | 1 | 0.4 |  |  | 3 | 0.7 |  |  |
| 135 | 405 |  |  |  |  |  |  |  |  | 1 | 0.7 |  |  |
| 145 | 435 |  |  |  |  | 2 | 0.4 |  |  | 3 | 0.7 |  |  |
| Maintenance Dose - 6 mg/kg/4 week | | | | | | | | | | | | | |
| 5 | 30 | 1 | 1 |  |  |  |  |  |  |  |  |  |  |
| 15 | 90 | 1 | 1 |  |  | 1 | 0.4 |  |  |  |  |  |  |
| 25 | 150 |  |  |  |  |  |  |  |  |  |  |  |  |
| 35 | 210 |  |  |  |  |  |  |  |  | 2 | 0.7 |  |  |
| 45 | 270 |  |  |  |  | 2 | 0.4 |  |  |  |  |  |  |
| 55 | 330 | 1 | 1 |  |  |  |  |  |  |  |  |  |  |
| 65 | 390 |  |  |  |  | 4 | 0.4 |  |  |  |  |  |  |
| 75 | 450 |  |  |  |  |  |  |  |  |  |  |  |  |
| 85 | 510 |  |  |  |  | 1 | 0.4 |  |  |  |  |  |  |
| 95 | 570 |  |  |  |  | 2 | 0.4 |  |  |  |  |  |  |
| 105 | 630 | 1 | 1 |  |  |  |  |  |  |  |  |  |  |
| 115 | 690 |  |  |  |  | 4 | 0.4 |  |  |  |  |  |  |
| 125 | 750 |  |  |  |  |  |  |  |  |  |  |  |  |
| 135 | 810 |  |  |  |  | 1 | 0.4 |  |  |  |  |  |  |
| 145 | 870 |  |  |  |  | 2 | 0.4 |  |  |  |  |  |  |

|  |  | 150 mg/1.0 mL (150 mg/mL) B | | | | | | SB | P | T | B |
|---|---|---|---|---|---|---|---|---|---|---|---|
|  |  | Full | | Part | | | | | | | |
| Wt | TD | # V | Vol. | # V | Vol. | TV | VD | ml | ml | ml | ml |
| Maintenance Dose - 1.5 mg/kg/week | | | | | | | | | | | |
| 5 | 7.5 |  |  |  |  | 0.25 | 1 | 0.25 | 0 | 0 | 0 |
| 15 | 22.5 |  |  |  |  | 0.75 | 1 | 0.75 | 0 | 0 | 0 |
| 25 | 37.5 |  |  |  |  | 0.25 | 1 | 0 | 0.25 | 0 | 0 |
| 35 | 52.5 |  |  |  |  | 0.35 | 1 | 0 | 0.35 | 0 | 0 |

-continued

| | | | | | | | | | | |
|---|---|---|---|---|---|---|---|---|---|---|
| 45 | 67.5 | | | | | 0.65 | 2 | 0.25 | 0.4 | 0 | 0 |
| 55 | 82.5 | | | | | 1.15 | 2 | 0.75 | 0.4 | 0 | 0 |
| 65 | 97.5 | | | | | 0.65 | 1 | 0 | 0 | 0.65 | 0 |
| 75 | 112.5 | | | | | 0.75 | 2 | 0 | 0.75 | 0 | 0 |
| 85 | 127.5 | | | | | 1.45 | 2 | 0.75 | 0 | 0.7 | 0 |
| 95 | 142.5 | | | 1 | 0.95 | 0.95 | 1 | 0 | 0 | 0 | 0.95 |
| 105 | 157.5 | | | | | 1.05 | 2 | 0 | 0.35 | 0.7 | 0 |
| 115 | 172.5 | 1 | 1 | | | 1.75 | 2 | 0.75 | 0 | 0 | 1 |
| 125 | 187.5 | | | | | 1.85 | 3 | 0.75 | 0.4 | 0.7 | 0 |
| 135 | 202.5 | | | | | 1.35 | 2 | 0 | 0 | 1.35 | 0 |
| 145 | 217.5 | | | | | 1.45 | 3 | 0 | 0.75 | 0.7 | 0 |
| Maintenance Dose - 3 mg/kg/2 week | | | | | | | | | | | |
| 5 | 15 | | | | | 0.5 | 1 | 0.5 | 0 | 0 | 0 |
| 15 | 45 | | | | | 0.3 | 1 | 0 | 0.3 | 0 | 0 |
| 25 | 75 | | | | | 0.9 | 2 | 0.5 | 0.4 | 0 | 0 |
| 35 | 105 | | | | | 0.7 | 1 | 0 | 0 | 0.7 | 0 |
| 45 | 135 | | | | | 1.7 | 2 | 1 | 0 | 0.7 | 0 |
| 55 | 165 | | | | | 1.1 | 2 | 0 | 0.4 | 0.7 | 0 |
| 65 | 195 | | | | | 2.1 | 3 | 1 | 0.4 | 0.7 | 0 |
| 75 | 225 | | | | | 1.5 | 3 | 0 | 0.8 | 0.7 | 0 |
| 85 | 255 | 1 | 1 | | | 1.7 | 2 | 0 | 0 | 0.7 | 1 |
| 95 | 285 | | | | | 1.9 | 4 | 0 | 1.2 | 0.7 | 0 |
| 105 | 315 | | | | | 2.1 | 3 | 0 | 0 | 2.1 | 0 |
| 115 | 345 | | | | | 2.3 | 5 | 0 | 1.6 | 0.7 | 0 |
| 125 | 375 | | | | | 2.5 | 4 | 0 | 0.4 | 2.1 | 0 |
| 135 | 405 | 2 | 1 | | | 2.7 | 3 | 0 | 0 | 0.7 | 2 |
| 145 | 435 | | | | | 2.9 | 5 | 0 | 0.8 | 2.1 | 0 |
| Maintenance Dose - 6 mg/kg/4 week | | | | | | | | | | | |
| 5 | 30 | | | | | 1 | 1 | 1 | 0 | 0 | 0 |
| 15 | 90 | | | | | 1.4 | 2 | 1 | 0.4 | 0 | 0 |
| 25 | 150 | 1 | 1 | | | 1 | 1 | 0 | 0 | 0 | 1 |
| 35 | 210 | | | | | 1.4 | 2 | 0 | 0 | 1.4 | 0 |
| 45 | 270 | 1 | 1 | | | 1.8 | 3 | 0 | 0.8 | 0 | 1 |
| 55 | 330 | 2 | 1 | | | 3 | 3 | 1 | 0 | 0 | 2 |
| 65 | 390 | 1 | 1 | | | 2.6 | 5 | 0 | 1.6 | 0 | 1 |
| 75 | 450 | 3 | 1 | | | 3 | 3 | 0 | 0 | 0 | 3 |
| 85 | 510 | 3 | 1 | | | 3.4 | 4 | 0 | 0.4 | 0 | 3 |
| 95 | 570 | 3 | 1 | | | 3.8 | 5 | 0 | 0.8 | 0 | 3 |
| 105 | 630 | 4 | 1 | | | 5 | 5 | 1 | 0 | 0 | 4 |
| 115 | 690 | 3 | 1 | | | 4.6 | 7 | 0 | 1.6 | 0 | 3 |
| 125 | 750 | 5 | 1 | | | 5 | 5 | 0 | 0 | 0 | 5 |
| 135 | 810 | 5 | 1 | | | 5.4 | 6 | 0 | 0.4 | 0 | 5 |
| 145 | 870 | 5 | 1 | | | 5.8 | 7 | 0 | 0.8 | 0 | 5 |

Table 4 (continued) shows additional columns - the weight column is repeated for ease of reading. In the table below, all abbreviations are as in Table 2.

| | | Inj. 1 | | Inj. 2 | | Inj. 3 | | | | Syr(n) | | Across M reg. | | | | | | |
|---|---|---|---|---|---|---|---|---|---|---|---|---|---|---|---|---|---|---|
| | | | | | | | | | | 1 | 2 | Least | Least | SB | P | T | B | |
| Wt | VCC | SyS | Instr. | SyS | Instr. | SyS | Instr. | NI | W4 | ml | ml | W | Inj. | mg | mg | mg | mg | TD |
| Maintenance Dose - 1.5 mg/kg/week | | | | | | | | | | | | | | | | | | |
| 5 | | 1 | 0.25 mL: SB; | | | | | 1 | 90 | 1 | 0 | | X | 7.5 | 0 | 0 | 0 | 7.5 |
| 15 | | 1 | 0.75 mL: SB; | | | | | 1 | 30 | 1 | 0 | | X | 22.5 | 0 | 0 | 0 | 22.5 |
| 25 | | 1 | 0.25 mL: P; | | | | | 1 | 90 | 1 | 0 | | X | 0 | 37.5 | 0 | 0 | 37.5 |
| 35 | | 1 | 0.35 mL: P; | | | | | 1 | 30 | 1 | 0 | | X | 0 | 52.5 | 0 | 0 | 52.5 |
| 45 | X | 1 | 0.25 mL: SB; | 1 | 0.4 mL: P; | | | 2 | 90 | 2 | 0 | | | 7.5 | 60 | 0 | 0 | 67.5 |
| 55 | X | 1 | 0.75 mL: SB; | 1 | 0.4 mL: P; | | | 2 | 30 | 2 | 0 | | | 22.5 | 60 | 0 | 0 | 82.5 |
| 65 | | 1 | 0.65 mL: T; | | | | | 1 | 30 | 1 | 0 | | X | 0 | 0 | 97.5 | 0 | 97.5 |
| 75 | | 1 | 0.4 mL: P; 0.35 mL: P; | | | | | 1 | 30 | 1 | 0 | | X | 0 | 112.5 | 0 | 0 | 112.5 |
| 85 | X | 1 | 0.75 mL: SB; | 1 | 0.7 mL: T; | | | 2 | 30 | 2 | 0 | | | 22.5 | 0 | 105 | 0 | 127.5 |
| 95 | | 1 | 0.95 mL: B; | | | | | 1 | 30 | 1 | 0 | | X | 0 | 0 | 0 | 142.5 | 142.5 |
| 105 | | 1 | 0.35 mL: P; | 1 | 0.7 mL: T; | | | 2 | 30 | 2 | 0 | | X | 0 | 52.5 | 105 | 0 | 157.5 |
| 115 | X | 1 | 0.75 mL: SB; | 1 | 1 mL: B; | | | 2 | 30 | 2 | 0 | | X | 22.5 | 0 | 0 | 150 | 172.5 |
| 125 | X | 1 | 0.75 mL: SB; | 2 | 0.4 mL: P; 0.7 mL: T; | | | 2 | 30 | 1 | 1 | | X | 22.5 | 60 | 105 | 0 | 187.5 |
| 135 | | 1 | 0.65 mL: T; | 1 | 0.7 mL: T; | | | 2 | 30 | 2 | 0 | | X | 0 | 0 | 202.5 | 0 | 202.5 |
| 145 | | 1 | 0.35 mL: P; 0.4 mL: P; | 1 | 0.7 mL: T; | | | 2 | 30 | 2 | 0 | | X | 0 | 112.5 | 105 | 0 | 217.5 |
| Maintenance Dose - 3 mg/kg/2 week | | | | | | | | | | | | | | | | | | |
| 5 | | 1 | 0.5 mL: SB; | | | | | 1 | 30 | 1 | 0 | | X | 15 | 0 | 0 | 0 | 15 |
| 15 | | 1 | 0.3 mL: P; | | | | | 1 | 30 | 1 | 0 | | X | 0 | 45 | 0 | 0 | 45 |

-continued

| | | | | | | | | | | | | | | | | |
|---|---|---|---|---|---|---|---|---|---|---|---|---|---|---|---|---|
| 25 | X | 1 | 0.5 mL: SB; | 1 | 0.4 mL: P; | 2 | 30 | 2 | 0 | | | 15 | 60 | 0 | 0 | 75 |
| 35 | | 1 | 0.7 mL: T; | | | 1 | 0 | 1 | 0 | X | X | 0 | 0 | 105 | 0 | 105 |
| 45 | X | 1 | 1 mL: SB; | 1 | 0.7 mL: T; | 2 | 0 | 2 | 0 | X | | 30 | 0 | 105 | 0 | 135 |
| 55 | | 2 | 0.4 mL: P; 0.7 mL: T; | | | 1 | 0 | 0 | 1 | X | X | 0 | 60 | 105 | 0 | 165 |
| 65 | X | 1 | 1 mL: SB; | 2 | 0.4 mL: P; 0.7 mL: T; | 2 | 0 | 1 | 1 | X | | 30 | 60 | 105 | 0 | 195 |
| 75 | | 2 | 0.4 mL: P; 0.4 mL: P; 0.7 mL: T; | | | 1 | 0 | 0 | 1 | X | X | 0 | 120 | 105 | 0 | 225 |
| 85 | | 2 | 0.7 mL: T; 1 mL: B; | | | 1 | 0 | 0 | 1 | X | X | 0 | 0 | 105 | 150 | 255 |
| 95 | | 2 | 0.4 mL: P; 0.4 mL: P; 0.4 mL: P; 0.7 mL: T; | | | 1 | 0 | 0 | 1 | X | X | 0 | 180 | 105 | 0 | 285 |
| 105 | | 2 | 0.7 mL: T; 0.7 mL: T; | 1 | 0.7 mL: T; | 2 | 0 | 1 | 1 | X | X | 0 | 0 | 315 | 0 | 315 |
| 115 | | 2 | 0.4 mL: P; 0.4 mL: P; 0.4 mL: P; 0.7 mL: T; | 1 | 0.4 mL: P; | 2 | 0 | 1 | 1 | X | X | 0 | 240 | 105 | 0 | 345 |
| 125 | | 2 | 0.4 mL: P; 0.7 mL: T; 0.7 mL: T; | 1 | 0.7 mL: T; | 2 | 0 | 1 | 1 | X | X | 0 | 60 | 315 | 0 | 375 |
| 135 | | 2 | 1 mL: B; 1 mL: B; | 1 | 0.7 mL: T; | 2 | 0 | 1 | 1 | X | X | 0 | 0 | 105 | 300 | 405 |
| 145 | | 2 | 0.4 mL: P; 0.7 mL: T; 0.7 mL: T; | 2 | 0.4 mL: P; 0.7 mL: T; | 2 | 0 | 0 | 2 | X | X | 0 | 120 | 315 | 0 | 435 |
| Maintenance Dose - 6 mg/kg/4 week | | | | | | | | | | | | | | | | |
| 5 | | 1 | 1 mL: SB; | | | 1 | 0 | 1 | 0 | X | X | 30 | 0 | 0 | 0 | 30 |
| 15 | X | 1 | 1 mL: SB; | 1 | 0.4 mL: P; | 2 | 0 | 2 | 0 | X | | 30 | 60 | 0 | 0 | 90 |
| 25 | | 1 | 1 mL: B; | | | 1 | 0 | 1 | 0 | X | X | 0 | 0 | 0 | 150 | 150 |
| 35 | | 2 | 0.7 mL: T; 0.7 mL: T; | | | 1 | 0 | 0 | 1 | X | X | 0 | 0 | 210 | 0 | 210 |
| 45 | | 2 | 0.4 mL: P; 0.4 mL: P; 1 mL: B; | | | 1 | 0 | 0 | 1 | X | X | 0 | 120 | 0 | 150 | 270 |
| 55 | X | 1 | 1 mL: SB; | 2 | 1 mL: B; 1 mL: B; | 2 | 0 | 1 | 1 | X | | 30 | 0 | 0 | 300 | 330 |
| 65 | | 2 | 0.4 mL: P; 0.4 mL: P; 1 mL: B; | 1 | 0.4 mL: P; 0.4 mL: P; | 2 | 0 | 1 | 1 | X | | 0 | 240 | 0 | 150 | 390 |
| 75 | | 2 | 1 mL: B; 1 mL: B; | 1 | 1 mL: B; | 2 | 0 | 1 | 1 | X | | 0 | 0 | 0 | 450 | 450 |
| 85 | | 2 | 1 mL: B; 1 mL: B; | 2 | 0.4 mL: P; 1 mL: B; | 2 | 0 | 0 | 2 | X | | 0 | 60 | 0 | 450 | 510 |
| 95 | | 2 | 1 mL: B; 1 mL: B; | 2 | 0.4 mL: P; 0.4 mL: P; 1 mL: B; | 2 | 0 | 0 | 2 | X | | 0 | 120 | 0 | 450 | 570 |
| 105 | X | 1 | 1 mL: SB; | 2 | 1 mL: B; 1 mL: B; | 2 | 1 mL: B; 1 mL: B; | 3 | 0 | 1 | 2 | X | 30 | 0 | 0 | 600 | 630 |
| 115 | | 2 | 1 mL: B; | 2 | 0.4 mL: P; 0.4 mL: P; 1 mL: B; | 1 | 0.4 mL: P; 0.4 mL: P; | 3 | 0 | 1 | 2 | X | 0 | 240 | 0 | 450 | 690 |
| 125 | | 2 | 1 mL: B; 1 mL: B; | 2 | 1 mL: B; 1 mL: B; | 1 | 1 mL: B; | 3 | 0 | 1 | 2 | X | 0 | 0 | 0 | 750 | 750 |
| 135 | | 2 | 1 mL: B; 1 mL: B; | 2 | 1 mL: B; 1 mL: B; | 2 | 0.4 mL: P; 1 mL: B; | 3 | 0 | 0 | 3 | X | 0 | 60 | 0 | 750 | 810 |
| 145 | | 2 | 1 mL: B; 1 mL: B; | 2 | 1 mL: B; 1 mL: B; | 2 | 0.4 mL: P; 0.4 mL: P; 1 mL: B; | 3 | 0 | 0 | 3 | X | 0 | 120 | 0 | 750 | 870 |

Table 5 shows a subset of data (45 out of 441 rows) in a "least injections—maintenance phase" recommendations table generated in the present exemplary embodiment. As mentioned above, the maintenance phase regimen includes three types of administration regimen (1.5 mg/kg/week, 3 mg/kg/2 weeks, 6 mg/kg/4 weeks) in this example. In the table below, all abbreviations are as in Table 2.

| | | 30 mg/1.0 mL (30 mg/mL) SB | | | | 60 mg/0.4 mL (150 mg/mL) P | | | | 105 mg/0.7 mL (150 mg/mL) T | | | |
|---|---|---|---|---|---|---|---|---|---|---|---|---|---|
| | | Full | | Part vial | | Full vial | | Part vial | | Full vial | | Part vial | |
| Wt | TD | # V | Vol. | # V | Vol. | # V | Vol | # V | Vol. | # V | Vol. | # V | Vol. |
| | | | | Maintenance Dose - 1.5 mg/kg/week | | | | | | | | | |
| 5 | 7.5 | | | 1 | 0.25 | | | | | | | | |
| 15 | 22.5 | | | 1 | 0.75 | | | | | | | | |
| 25 | 37.5 | | | | | | | 1 | 0.25 | | | | |
| 35 | 52.5 | | | | | | | 1 | 0.35 | | | | |
| 45 | 67.5 | | | | | | | | | | | 1 | 0.45 |
| 55 | 82.5 | | | | | | | | | | | 1 | 0.55 |
| 65 | 97.5 | | | | | | | | | | | 1 | 0.65 |
| 75 | 112.5 | | | | | | | | | | | | |
| 85 | 127.5 | | | | | | | | | | | | |
| 95 | 142.5 | | | | | | | | | | | | |
| 105 | 157.5 | | | | | | | 1 | 0.35 | 1 | 0.7 | | |
| 115 | 172.5 | | | 1 | 0.75 | | | | | | | | |
| 125 | 187.5 | | | | | | | | | 1 | 0.7 | 1 | 0.55 |
| 135 | 202.5 | | | | | | | | | 1 | 0.7 | 1 | 0.65 |
| 145 | 217.5 | | | | | | | | | | | 1 | 0.45 |
| | | | | Maintenance Dose - 3 mg/kg/2 week | | | | | | | | | |
| 5 | 15 | | | 1 | 0.5 | | | | | | | | |
| 15 | 45 | | | | | | | 1 | 0.3 | | | | |
| 25 | 75 | | | | | | | | | | | 1 | 0.5 |
| 35 | 105 | | | | | | | | | 1 | 0.7 | | |
| 45 | 135 | 1 | 1 | | | | | | | | | | |
| 55 | 165 | | | | | | | | | | | | |
| 65 | 195 | 1 | 1 | | | 1 | 0.4 | | | 1 | 0.7 | | |
| 75 | 225 | | | | | | | | | 1 | 0.7 | 1 | 0.6 |
| 85 | 255 | | | | | | | | | | | 1 | 0.5 |
| 95 | 285 | | | | | | | | | 1 | 0.7 | | |
| 105 | 315 | | | | | | | | | | | | |
| 115 | 345 | | | | | | | | | 3 | 0.7 | | |
| 125 | 375 | | | | | | | 1 | 0.3 | | | | |
| 135 | 405 | | | | | | | | | | | 1 | 0.5 |
| 145 | 435 | | | | | | | | | 1 | 0.7 | | |
| | | | | Maintenance Dose - 6 mg/kg/4 week | | | | | | | | | |
| 5 | 30 | 1 | 1 | | | | | | | | | | |
| 15 | 90 | | | | | | | | | | | 1 | 0.6 |
| 25 | 150 | | | | | | | | | | | | |
| 35 | 210 | | | | | | | | | 2 | 0.7 | | |
| 45 | 270 | | | | | | | | | | | | |
| 55 | 330 | | | | | | | | | | | | |
| 65 | 390 | 1 | 1 | | | | | | | | | | |
| 75 | 450 | | | | | | | | | | | 1 | 0.6 |
| 85 | 510 | | | | | | | | | | | | |
| 95 | 570 | | | | | 1 | 0.4 | | | | | | |
| 105 | 630 | | | | | | | | | | | | |
| 115 | 690 | 1 | 1 | | | | | | | | | | |
| 125 | 750 | | | | | | | | | | | 1 | 0.6 |
| 135 | 810 | | | | | | | | | | | | |
| 145 | 870 | | | | | 1 | 0.4 | | | | | | |

| | | 150 mg/1.0 mL (150 mg/mL) B | | | | | | | | | |
|---|---|---|---|---|---|---|---|---|---|---|---|
| | | Full | | Part | | | | | | | |
| Wt | TD | # V | Vol. | # V | Vol. | TV | VD | SB ml | P ml | T ml | B ml |
| | | | | Maintenance Dose - 1.5 mg/kg/week | | | | | | | |
| 5 | 7.5 | | | | | 0.25 | 1 | 0.25 | 0 | 0 | 0 |
| 15 | 22.5 | | | | | 0.75 | 1 | 0.75 | 0 | 0 | 0 |
| 25 | 37.5 | | | | | 0.25 | 1 | 0 | 0.25 | 0 | 0 |
| 35 | 52.5 | | | | | 0.35 | 1 | 0 | 0.35 | 0 | 0 |

-continued

| | | | | | | | | | | |
|---|---|---|---|---|---|---|---|---|---|---|
| 45 | 67.5 | | | | | 0.45 | 1 | 0 | 0 | 0.45 | 0 |
| 55 | 82.5 | | | | | 0.55 | 1 | 0 | 0 | 0.55 | 0 |
| 65 | 97.5 | | | | | 0.65 | 1 | 0 | 0 | 0.65 | 0 |
| 75 | 112.5 | | | 1 | 0.75 | 0.75 | 1 | 0 | 0 | 0 | 0.75 |
| 85 | 127.5 | | | 1 | 0.85 | 0.85 | 1 | 0 | 0 | 0 | 0.85 |
| 95 | 142.5 | | | 1 | 0.95 | 0.95 | 1 | 0 | 0 | 0 | 0.95 |
| 105 | 157.5 | | | | | 1.05 | 2 | 0 | 0.35 | 0.7 | 0 |
| 115 | 172.5 | 1 | 1 | | | 1.75 | 2 | 0.75 | 0 | 0 | 1 |
| 125 | 187.5 | | | | | 1.25 | 2 | 0 | 0 | 1.25 | 0 |
| 135 | 202.5 | | | | | 1.35 | 2 | 0 | 0 | 1.35 | 0 |
| 145 | 217.5 | 1 | 1 | | | 1.45 | 2 | 0 | 0 | 0.45 | 1 |
| Maintenance Dose - 3 mg/kg/2 week | | | | | | | | | | | |
| 5 | 15 | | | | | 0.5 | 1 | 0.5 | 0 | 0 | 0 |
| 15 | 45 | | | | | 0.3 | 1 | 0 | 0.3 | 0 | 0 |
| 25 | 75 | | | | | 0.5 | 1 | 0 | 0 | 0.5 | 0 |
| 35 | 105 | | | | | 0.7 | 1 | 0 | 0 | 0.7 | 0 |
| 45 | 135 | | | 1 | 0.9 | 0.9 | 1 | 0 | 0 | 0 | 0.9 |
| 55 | 165 | | | 1 | 0.92 | 0.92 | 1 | 0 | 0 | 0 | 0.92 |
| 65 | 195 | | | | | 1.1 | 2 | 0 | 0.4 | 0.7 | 0 |
| 75 | 225 | | | | | 1.3 | 2 | 0 | 0 | 1.3 | 0 |
| 85 | 255 | 1 | 1 | | | 1.5 | 2 | 0 | 0 | 0.5 | 1 |
| 95 | 285 | 1 | 1 | | | 1.7 | 2 | 0 | 0 | 0.7 | 1 |
| 105 | 315 | 1 | 1 | 1 | 0.9 | 1.9 | 2 | 0 | 0 | 0 | 1.9 |
| 115 | 345 | | | | | 2.1 | 3 | 0 | 0 | 2.1 | 0 |
| 125 | 375 | 2 | 1 | | | 2.3 | 3 | 0 | 0.3 | 0 | 2 |
| 135 | 405 | 2 | 1 | | | 2.5 | 3 | 0 | 0 | 0.5 | 2 |
| 145 | 435 | 2 | 1 | | | 2.7 | 3 | 0 | 0 | 0.7 | 2 |
| Maintenance Dose - 6 mg/kg/4 week | | | | | | | | | | | |
| 5 | 30 | | | | | 1 | 1 | 1 | 0 | 0 | 0 |
| 15 | 90 | | | | | 0.6 | 1 | 0 | 0 | 0.6 | 0 |
| 25 | 150 | 1 | 1 | | | 1 | 1 | 0 | 0 | 0 | 1 |
| 35 | 210 | | | | | 1.4 | 2 | 0 | 0 | 1.4 | 0 |
| 45 | 270 | 1 | 1 | 1 | 0.8 | 1.8 | 2 | 0 | 0 | 0 | 1.8 |
| 55 | 330 | 1 | 1 | 1 | 0.84 | 1.84 | 2 | 0 | 0 | 0 | 1.84 |
| 65 | 390 | 2 | 1 | | | 3 | 3 | 1 | 0 | 0 | 2 |
| 75 | 450 | 2 | 1 | | | 2.6 | 3 | 0 | 0 | 0.6 | 2 |
| 85 | 510 | 3 | 1 | | | 3 | 3 | 0 | 0 | 0 | 3 |
| 95 | 570 | 3 | 1 | | | 3.4 | 4 | 0 | 0.4 | 0 | 3 |
| 105 | 630 | 3 | 1 | 1 | 0.8 | 3.8 | 4 | 0 | 0 | 0 | 3.8 |
| 115 | 690 | 4 | 1 | | | 5 | 5 | 1 | 0 | 0 | 4 |
| 125 | 750 | 4 | 1 | | | 4.6 | 5 | 0 | 0 | 0.6 | 4 |
| 135 | 810 | 5 | 1 | | | 5 | 5 | 0 | 0 | 0 | 5 |
| 145 | 870 | 5 | 1 | | | 5.4 | 6 | 0 | 0.4 | 0 | 5 |

Table 5 (continued) shows additional columns - the weight column is repeated for ease of reading. In the table below, all abbreviations are as in Table 2.

| | | Inj. 1 | | Inj. 2 | | Inj. 3 | | | |
|---|---|---|---|---|---|---|---|---|---|
| Wt | VCC | SyS | Instr. | SyS | Instr. | SyS | Instr. | NI | W4 |
| Maintenance Dose - 1.5 mg/kg/week | | | | | | | | | |
| 5 | | 1 | 0.25 mL: SB; | | | | | 1 | 90 |
| 15 | | 1 | 0.75 mL: SB; | | | | | 1 | 30 |
| 25 | | 1 | 0.25 mL: P; | | | | | 1 | 90 |
| 35 | | 1 | 0.35 mL: P; | | | | | 1 | 30 |
| 45 | | 1 | 0.45 mL: T; | | | | | 1 | 150 |
| 55 | | 1 | 0.55 mL: T; | | | | | 1 | 90 |
| 65 | | 1 | 0.65 mL: T; | | | | | 1 | 30 |
| 75 | | 1 | 0.75 mL: B; | | | | | 1 | 150 |
| 85 | | 1 | 0.85 mL: B; | | | | | 1 | 90 |
| 95 | | 1 | 0.95 mL: B; | | | | | 1 | 30 |
| 105 | | 1 | 0.35 mL: P; | 1 | 0.7 mL: T; | | | 2 | 30 |
| 115 | X | 1 | 0.75 mL: SB; | 1 | 1 mL: B; | | | 2 | 30 |
| 125 | | 1 | 0.55 mL: T; | 1 | 0.7 mL: T; | | | 2 | 90 |
| 135 | | 1 | 0.65 mL: T; | 1 | 0.7 mL: T; | | | 2 | 30 |
| 145 | | 1 | 0.45 mL: T; | 1 | 1 mL: B; | | | 2 | 150 |
| Maintenance Dose - 3 mg/kg/2 week | | | | | | | | | |
| 5 | | 1 | 0.5 mL: SB; | | | | | 1 | 30 |
| 15 | | 1 | 0.3 mL: P; | | | | | 1 | 30 |
| 25 | | 1 | 0.5 mL: T; | | | | | 1 | 60 |
| 35 | | 1 | 0.7 mL: T; | | | | | 1 | 0 |
| 45 | | 1 | 0.9 mL: B; | | | | | 1 | 30 |
| 55 | | 1 | 0.92 mL: B; | | | | | 1 | 24 |

| | | | | | | | | |
|---|---|---|---|---|---|---|---|---|
| 65 | | 2 | 0.4 mL: P;<br>0.7 mL: T; | | | | 1 | 0 |
| 75 | | 2 | 0.7 mL: T;<br>0.6 mL: T; | | | | 1 | 30 |
| 85 | | 2 | 0.5 mL: T;<br>1 mL: B; | | | | 1 | 60 |
| 95 | | 2 | 0.7 mL: T;<br>1 mL: B; | | | | 1 | 0 |
| 105 | | 2 | 1 mL: B;<br>0.9 mL: B; | | | | 1 | 30 |
| 115 | | 2 | 0.7 mL: T;<br>0.7 mL: T; | 1 | 0.7 mL: T; | | 2 | 0 |
| 125 | | 2 | 1 mL: B;<br>1 mL: B; | 1 | 0.3 mL: P; | | 2 | 30 |
| 135 | | 2 | 1 mL: B;<br>1 mL: B; | 1 | 0.5 mL: T; | | 2 | 60 |
| 145 | | 2 | 1 mL: B;<br>1 mL: B; | 1 | 0.7 mL: T; | | 2 | 0 |
| Maintenance Dose - 6 mg/kg/4 week | | | | | | | | |
| 5 | | 1 | 1 mL: SB; | | | | 1 | 0 |
| 15 | | 1 | 0.6 mL: T; | | | | 1 | 15 |
| 25 | | 1 | 1 mL: B; | | | | 1 | 0 |
| 35 | | 2 | 0.7 mL: T;<br>0.7 mL: T; | | | | 1 | 0 |
| 45 | | 2 | 1 mL: B;<br>0.8 mL: B; | | | | 1 | 30 |
| 55 | | 1 | 0.84 mL: B; | 1 | 1 mL: B; | | 2 | 24 |
| 65 | X | 1 | 1 mL: SB; | 2 | 1 mL: B;<br>1 mL: B; | | 2 | 0 |
| 75 | | 2 | 1 mL: B;<br>1 mL: B; | 1 | 0.6 mL: T; | | 2 | 15 |
| 85 | | 2 | 1 mL: B;<br>1 mL: B; | 1 | 1 mL: B; | | 2 | 0 |
| 95 | | 2 | 1 mL: B;<br>1 mL: B; | 2 | 0.4 mL: P;<br>1 mL: B; | | 2 | 0 |
| 105 | | 2 | 1 mL: B;<br>1 mL: B; | 2 | 1 mL: B;<br>0.8 mL: B; | | 2 | 30 |
| 115 | X | 1 | 1 mL: SB; | 2 | 1 mL: B;<br>1 mL: B; | 2 | 1 mL: B;<br>1 mL: B; | 3 | 0 |
| 125 | | 2 | 1 mL: B;<br>1 mL: B; | 2 | 1 mL: B;<br>1 mL: B; | 1 | 0.6 mL: T; | 3 | 15 |
| 135 | | 2 | 1 mL: B;<br>1 mL: B; | 2 | 1 mL: B;<br>1 mL: B; | 1 | 1 mL: B; | 3 | 0 |
| 145 | | 2 | 1 mL: B;<br>1 mL: B; | 2 | 1 mL: B;<br>1 mL: B; | 2 | 0.4 mL: P;<br>1 mL: B; | 3 | 0 |

| | | Syr (n) | | Across M reg. | | | | | | |
|---|---|---|---|---|---|---|---|---|---|---|
| Wt | VCC | 1 ml | 2 ml | Least W | Least Inj- | SB mg | P mg | T mg | B mg | TD |
| Maintenance Dose - 1.5 mg/kg/week | | | | | | | | | | |
| 5 | | 1 | 0 | | X | 0.25 | 0 | 0 | 0 | 7.5 |
| 15 | | 1 | 0 | | X | 0.75 | 0 | 0 | 0 | 22.5 |
| 25 | | 1 | 0 | | X | 0 | 0.25 | 0 | 0 | 37.5 |
| 35 | | 1 | 0 | | X | 0 | 0.35 | 0 | 0 | 52.5 |
| 45 | | 1 | 0 | | X | 0 | 0 | 0.45 | 0 | 67.5 |
| 55 | | 1 | 0 | | X | 0 | 0 | 0.55 | 0 | 82.5 |
| 65 | | 1 | 0 | | X | 0 | 0 | 0.65 | 0 | 97.5 |
| 75 | | 1 | 0 | | X | 0 | 0 | 0 | 0.75 | 112.5 |
| 85 | | 1 | 0 | | X | 0 | 0 | 0 | 0.85 | 127.5 |
| 95 | | 1 | 0 | X | X | 0 | 0 | 0 | 0.95 | 142.5 |
| 105 | | 2 | 0 | | X | 0 | 0.35 | 0.7 | 0 | 157.5 |
| 115 | X | 2 | 0 | | X | 0.75 | 0 | 0 | 1 | 172.5 |
| 125 | | 2 | 0 | | X | 0 | 1.25 | 0 | 0 | 187.5 |
| 135 | | 2 | 0 | | X | 0 | 0 | 1.35 | 0 | 202.5 |
| 145 | | 2 | 0 | | X | 0 | 0 | 0.45 | 1 | 217.5 |
| Maintenance Dose - 3 mg/kg/2 week | | | | | | | | | | |
| 5 | | 1 | 0 | | X | 0.5 | 0 | 0 | 0 | 15 |
| 15 | | 1 | 0 | | X | 0 | 0.3 | 0 | 0 | 45 |
| 25 | | 1 | 0 | | X | 0 | 0 | 0.5 | 0 | 75 |
| 35 | | 1 | 0 | X | X | 0 | 0 | 0.7 | 0 | 105 |
| 45 | | 1 | 0 | X | X | 0 | 0 | 0 | 0.9 | 135 |
| 55 | | 1 | 0 | X | X | 0 | 0 | 0 | 0.92 | 138 |
| 65 | | 0 | 1 | X | X | 0 | 0.4 | 0.7 | 0 | 165 |

-continued

| | | | | | | | | | |
|---|---|---|---|---|---|---|---|---|---|
| 75 | | 0 | 1 | | X | 0 | 0 | 1.3 | 0 | 195 |
| 85 | | 0 | 1 | | X | 0 | 0 | 0.5 | 1 | 225 |
| 95 | | 0 | 1 | X | X | 0 | 0 | 0.7 | 1 | 255 |
| 105 | | 0 | 1 | X | X | 0 | 0 | 0 | 1.9 | 285 |
| 115 | | 1 | 1 | X | | 0 | 0 | 2.1 | 0 | 315 |
| 125 | | 1 | 1 | | X | 0 | 0.3 | 0 | 2 | 345 |
| 135 | | 1 | 1 | | X | 0 | 0 | 0.5 | 2 | 375 |
| 145 | | 1 | 1 | X | X | 0 | 0 | 0.7 | 2 | 405 |
| Maintenance Dose - 6 mg/kg/4 week | | | | | | | | | | |
| 5 | | 1 | 0 | X | X | 1 | 0 | 0 | 0 | 30 |
| 15 | | 1 | 0 | X | X | 0 | 0 | 0.6 | 0 | 90 |
| 25 | | 1 | 0 | X | X | 0 | 0 | 0 | 1 | 150 |
| 35 | | 0 | 1 | X | X | 0 | 0 | 1.4 | 0 | 210 |
| 45 | | 0 | 1 | X | X | 0 | 0 | 0 | 1.8 | 270 |
| 55 | | 2 | 0 | X | | 0 | 0 | 0 | 1.84 | 276 |
| 65 | X | 1 | 1 | X | | 1 | 0 | 0 | 2 | 330 |
| 75 | | 1 | 1 | X | | 0 | 0 | 0.6 | 2 | 390 |
| 85 | | 1 | 1 | X | | 0 | 0 | 0 | 3 | 450 |
| 95 | | 0 | 2 | X | | 0 | 0.4 | 0 | 3 | 510 |
| 105 | | 0 | 2 | X | | 0 | 0 | 0 | 3.8 | 570 |
| 115 | X | 1 | 2 | X | | 1 | 0 | 0 | 4 | 630 |
| 125 | | 1 | 2 | X | | 0 | 0 | 0 | 750 | 690 |
| 135 | | 1 | 2 | X | | 0 | 60 | 0 | 750 | 750 |
| 145 | | 0 | 3 | X | | 0 | 120 | 0 | 750 | 810 |

All computations were conducted using Excel macros in Visual Basic (Microsoft®). It will be appreciated that additionally or alternatively, other programming languages and software may be employed for analysis.

An exemplary implementation of a user interface to the method of determining an administration regimen of a drug to a subject described above will now be described. The tables above, once computed by a processor, can for example be stored in a memory and used to provide recommendations to a user, via a user interface. Alternatively, the user interface can be used to send a request causing the processor to perform the computations described above and generate the recommendations on-the-fly (i.e. live, upon receipt of a request from a user). For example, a processor may, upon receipt of an input weight through the user interface, and optionally a selection of a criterion based on which the recommendations should be selected, implement steps 1 to 3 described above for a single weight, using parameters stored in memory. In this example, the parameters stored in memory can include any of: parameters of the dosage forms available, maximum syringe volumes available, types of dosage regimen (e.g. dose per kg per elemental period of time, allowable multiples of the elemental period of time, etc.).

Figure 3:
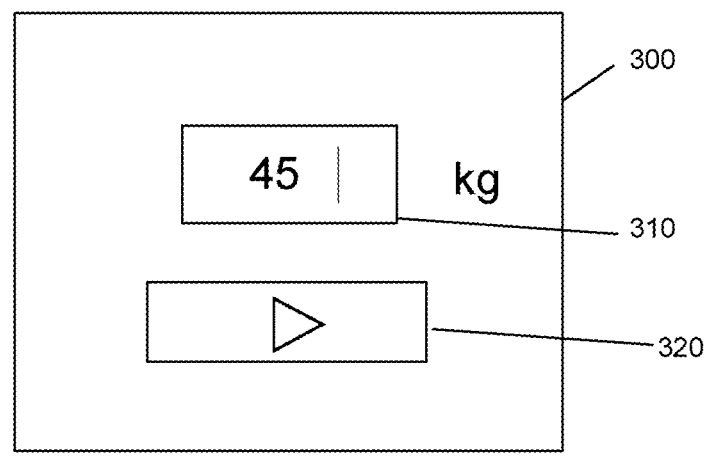
FIG. 3 shows the home screen of an exemplary implementation of a user interface for a method of determining an administration regimen of a drug to a subject.
Figure 4:
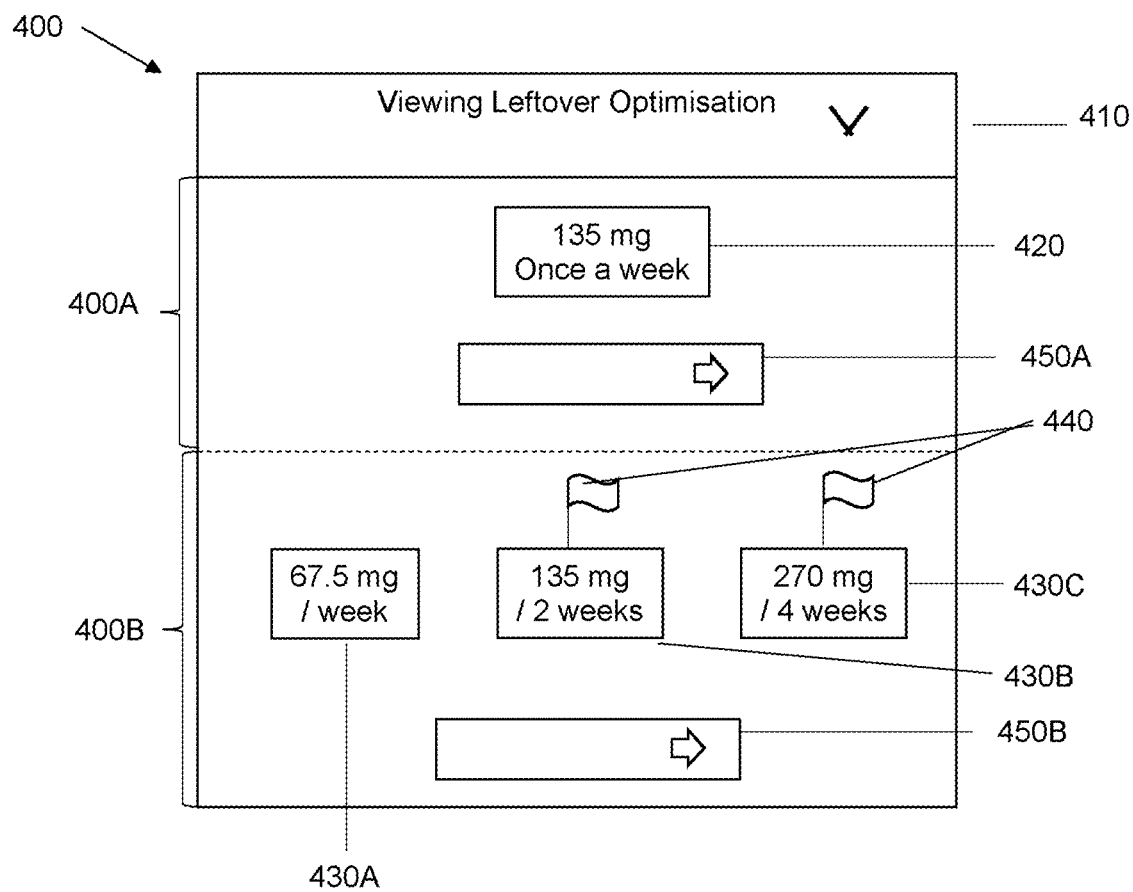
FIG. 4 shows the results screen of an exemplary implementation of a user interface for a method of determining an administration regimen of a drug to a subject.

FIG. 3 shows a home screen on an exemplary user interface through which the methods of the present invention can be accessed. The home screen 300 includes a weight input box 310, and a launch button 320. Entering a weight in the box 310 and selecting the launch button 320 will cause a request to be sent to a processor (either locally or on a server), which will either compute recommended dosage regimen based on the weight information, or retrieve the appropriate pre-computed dosage regimen stored in memory. The processor then provides information necessary for the user device to display a results screen 400. An example of a results screen is shown on FIG. 4. The processor may instead return an error message if the weight entered is outside of a pre-set range. The results screen 400 shown on FIG. 4 is separated in two parts, a loading dose part 400A and a maintenance dose part 400B. The loading dose part 400A includes a single dose recommendation 420, in line with clinical guidelines as discussed above. This can be obtained from the column "TD" in tables 2 and 3 above. The maintenance dose part 400B includes three dose recommendations 430A, 430B, 430C, reflecting the three different administration intervals in line with clinical guidelines as discussed above. These can be obtained from the column "TD" in Tables 4 and 5 above. The results screen 400 further includes a criteria selection drop down menu 410. In the example shown, the selected criterion is "leftover optimisation" (i.e. least wastage) by default, although alternative configurations are possible. Through this drop down menu 410, the user may be able to select a different criterion to prioritise in selecting recommended dosage regimen, where the choice of a criterion to be prioritised will result in the choice of one of two different hierarchies of criterion as explained above. A new selection through the drop down menu may cause the results screen 400 to refresh to show the corresponding recommended dosage regimens. In the example shown, the results page displayed is produced by outputting information from Tables 2 and 4 above, respectively for the loading dose part 400A and the maintenance dose part 400B. Should the "least injection" option be selected in the drop down menu 410, the page would be refreshed to include data selected from Tables 3 and 5, respectively. The dose recommendations 430B, 430C that optimise the criteria across all types of dose regimen are flagged 440. This information can be extracted from the column "Across M. Reg/least W" in Table 4. Each part further includes a "details" button 450A, 450B, which lead to detail screens as shown on FIG. 5.

Figure 5:
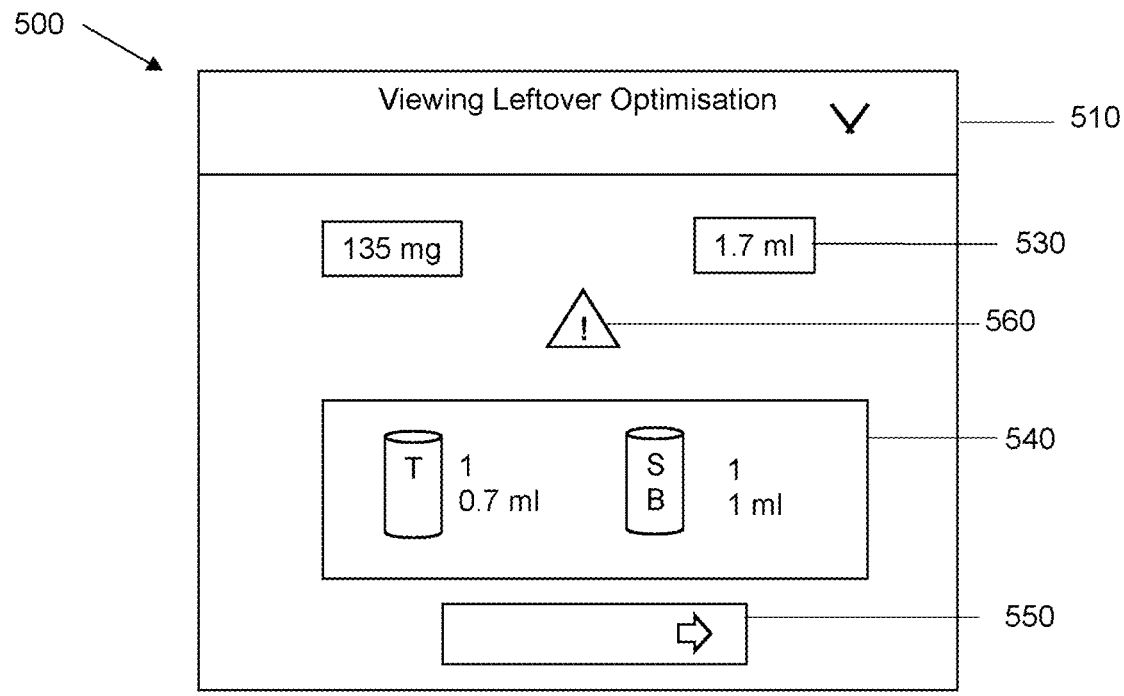
FIG. 5 shows a dose details interface of an exemplary implementation of a user interface for a method of determining an administration regimen of a drug to a subject.
Figure 6:
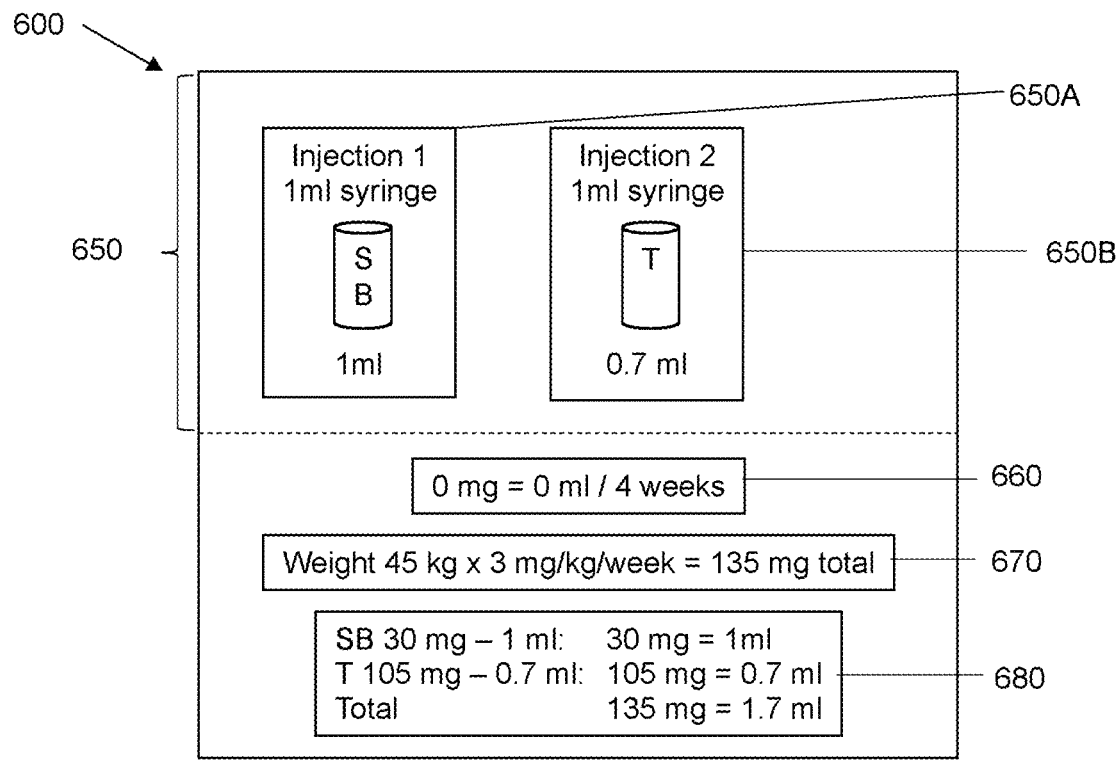
FIG. 6 shows an injection details interface of an exemplary implementation of a user interface for a method of determining an administration regimen of a drug to a subject.

FIG. 5 shows a loading dose details interface 500 that can be used to output a recommended loading dose regimen to a user. A similar interface (not shown) is produced for the maintenance dose using the details button 450B. The maintenance dose details interface (not shown) includes three panels, one for each type of dose regimen (weekly, biweekly, four-weekly) in this embodiment. In other embodiments, the maintenance dose details interface may include a single dose regimen which has been determined to be optimal across all types of dose regimen. The loading dose details interface 500 comprises an optimisation criteria drop down menu 510, and details about the recommended loading dose, based on the currently selected optimisation criterion. The details include the total dose 520, extracted from the column "TD" in Tables 2 to 5 (where Table 2 is used in this case), the total volume 530, extracted from the column "TV" in Tables 2 to 5 (where Table 2 is used in this case), a warning 560 that vials with two different concentrations are used, extracted from the column "VCC" in Tables 2 to 5 (where Table 2 is used in this case), and vial information 540 (which vials should be used, what amount should be used from the vials, and how many of the vials should be used—extracted from the columns "#V" and "#Vol." for each dosage form in in Tables 2 to 5). The interface 500 further includes an "Injection Details" button 550. The button 550 causes the processor to provide information necessary for the display of an injection details screen 600, and example of which is shown on FIG. 6A. The "Injection Detail" screen 600 contains an injection details panel 650 which provides the details of each administration 650A, 650B, extracted from the columns "Inj." in Tables 2 to 5. The screen 600 further includes a leftover calculation 660 (extracted from the column "W4" in Tables 2 to 5), a total dose detailed calculation 670 (extracted from columns "Wt" and "TD" in Tables 2 to 5), and a total volume calculation 680 (extracted from columns "#V", "#Vol." and "mg" for each dosage form in in Tables 2 to 5).

The terms "computer system" includes the hardware, software and data storage devices for embodying a system or carrying out a method according to the above described embodiments. For example, a computer system may comprise a central processing unit (CPU), input means, output means and data storage, which may be embodied as one or more connected computing devices. Preferably the computer system has a display or comprises a computing device that has a display to provide a visual output display (for example in the design of the business process). The data storage may comprise RAM, disk drives or other computer readable media. The computer system may include a plurality of computing devices connected by a network and able to communicate with each other over that network.

The methods of the above embodiments may be provided as computer programs or as computer program products or computer readable media carrying a computer program which is arranged, when run on a computer, to perform the method(s) described above.

The term "computer readable media" includes, without limitation, any non-transitory medium or media which can be read and accessed directly by a computer or computer system. The media can include, but are not limited to, magnetic storage media such as floppy discs, hard disc storage media and magnetic tape; optical storage media such as optical discs or CD-ROMs; electrical storage media such as memory, including RAM, ROM and flash memory; and hybrids and combinations of the above such as magnetic/optical storage media.

Unless context dictates otherwise, the descriptions and definitions of the features set out above are not limited to any particular aspect or embodiment of the invention and apply equally to all aspects and embodiments which are described.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

Other aspects and embodiments of the invention provide the aspects and embodiments described above with the term "comprising" replaced by the term "consisting of" or "consisting essentially of", unless the context dictates otherwise.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

All documents mentioned in this specification are incorporated herein by reference in their entirety.

The invention claimed is:

1. A method of treating a subject with a drug comprising:
(i) determining an administration regimen of the drug to a subject, by a processor:
receiving the value of at least one parameter associated with the subject;
determining the amount of drug ($A_t$) to be administered to the subject per elemental period of time (t) based at least in part on the value of the at least one parameter associated with the subject, wherein the drug is available in at least two different dosage forms (D1, D2) that differ by the total amount of drug and/or the drug concentration in a dose of the dosage form, wherein a dosage form is a pharmaceutical formulation of the drug associated with a total amount of the drug and a concentration of the drug in a dose, and wherein at least one of the dosage forms is a single use dosage form;
computing all minimal combinations ($A_t$ [D1,D2, D1D2]) of the at least two different dosage forms that can be used to achieve the amount of drug ($A_t$) to be administered to the subject, wherein a minimal combination is a combination that reaches or exceeds the amount of drug ($A_t$) to be administered to the subject by using the minimum number of doses of each dosage form in a combination of dosage forms (D1, D2, D1D2);

selecting a subset of the combinations ($A_t$ [D1,D2, D1D2]) that satisfy at least a first criterion and a second criterion, wherein the first and second criteria are selected from:

a criterion that applies to the value of the total wastage associated with the combinations, wherein the wastage associated with a combination of dosage forms ($W_t$ [D1,D2, D1D2]; $W_{n1t}$ [D1,D2, D1D2]; $W_{n2t}$ [D1,D2, D1D2]) is the difference between the total amount of drug in the combination of dosage forms and the amount of drug ($A_t$, $A_{n1t}$, $A_{n2t}$) to be administered to the subject, a criterion applies to the value of the total number of physical administrations steps associated with the combinations, and a criterion that applies to the total number of physical preparative steps associated with the combinations; and outputting at a user interface the selected subset of combinations as the optimal administration regimen(s) for the subject; and (ii) treating the subject with one of said optimal administration regimen(s).

2. The method of claim 1, wherein:
selecting a subset of the combinations ($A_t$ [D1,D2, D1D2]) that satisfy at least a first criterion and a second criterion comprises:
selecting a first subset of the combinations ($A_t$ [D1,D2, D1D2]) according to a first criterion and
selecting a second subset of the combinations from the first subset according to a second criterion different from the first criterion; and optionally selecting a third subset of the combinations from the second subset according to a third criterion; and
outputting the selected subset of combinations as the optimal administration regimen(s) for the subject comprises outputting the last selected subset of combinations as the optimal administration regimen(s) for the subject.

3. The method of claim 1, wherein the determining an administration regimen of the drug to the subject further comprises:
calculating, for one or more multiples (n) of the elemental period of time (t), the amount of drug ($A_{n1t}$, $A_{n2t}$) to be administered to the subject; and
computing all minimal combinations of the at least two different dosage forms that can be used to achieve the amounts of drug ($A_{n1t}$, $A_{n2t}$) to be administered to the subject for each of the multiples (n) of the elemental period of time (t).

4. The method of claim 3, wherein the determining an administration regimen of the drug to the subject comprises:
selecting the subsets of the combinations ($A_t$ [D1,D2, D1D2]; $A_{n1t}$ [D1,D2, D1D2]; $A_{n2t}$ [D1,D2, D1D2]) separately for the elemental period of time (t) and each of the multiples (n) of the elemental period of time (t); and
outputting the selected subset of combinations for the elemental period and each of the multiples (n) of the elemental period of time (t).

5. The method of claim 3, wherein the method comprises:
selecting the subsets of the combinations ($A_t$ [D1,D2, D1D2]; $A_{n1t}$ [D1,D2, D1D2]; $A_{n2t}$ [D1,D2, D1D2];) jointly for the elemental period of time (t) and all of the multiples (n) of the elemental period of time (t).

6. The method of claim 3, wherein the multiples (n) are integer multiples.

7. The method of claim 6, wherein the elemental period of time (t) is selected from: a day, a week and a month.

8. The method of claim 1, wherein the method comprises receiving the value of one or more further parameters associated with the subject, the one or more further parameters comprising: a selection of a criterion to be used as the first criterion, a selection of a criterion to be used as the second criterion, or both, optionally wherein the selection is from a predetermined set of criteria.

9. The method of claim 1, wherein determining an administration regimen of the drug to the subject further comprises computing the wastage associated with a combination of dosage forms ($W_t$ [D1,D2, D1D2]; $W_{n1t}$ [D1,D2, D1D2]; $W_{n2t}$ [D1,D2, D1D2]) as the difference between the total amount of drug in the combination of dosage forms and the amount of drug ($A_t$, $A_{n1t}$, $A_{n2t}$) to be administered to the subject, and the total wastage as the wastage per period of time, optionally wherein one of the criteria applies to the value of the total wastage associated with each selected combination.

10. The method of claim 1, wherein determining an administration regimen of the drug to the subject further comprises computing the total number of physical administration steps required to administer a combination.

11. The method of claim 1, wherein determining an administration regimen of the drug to the subject further comprises computing the total number of physical preparative steps required to administer a combination.

12. The method of claim 1, wherein the determining an administration regimen of the drug to the subject is implemented by a computing device comprising a user interface, receiving the value of at least one parameter associated with the subject comprises the computing device receiving information input by a user via the user interface, and outputting one or more optimal administration regimen(s) comprises the computing device providing information that identifies the one or more optimal administration regimen(s) to a user via the user interface.

13. The method of claim 1, wherein the determining an administration regimen of the drug to the subject is implemented by a computing device configured to communicate with a second computing device, receiving the value of at least one parameter associated with a subject comprises the computing device receiving information from the second computing device, and outputting one or more optimal administration regimen(s) comprises the computing device communicating information that identifies the one or more optimal administration regimen(s) to the second computing device.

14. The method of claim 1, wherein:
the drug is available in three dosage forms (D1,D2, D3), the drug is available in four dosage forms (D1,D2, D3, D4), the drug is available in five dosage forms (D1,D2, D3, D4, D5), or the drug is available in six dosage forms (D1,D2, D3, D4, D5, D6); and
at least two of the dosage forms differ from each other by the drug concentration in a dose of the dosage form.

* * * * *